(12) United States Patent
Blanco et al.

(10) Patent No.: US 9,670,247 B2
(45) Date of Patent: Jun. 6, 2017

(54) CONTRACEPTIVE AGENTS

(71) Applicants: Gustavo Blanco, Overland Park, KS (US); Gunda I. Georg, St. Paul, MN (US); Shameem Sultana Syeda, St. Paul, MN (US)

(72) Inventors: Gustavo Blanco, Overland Park, KS (US); Gunda I. Georg, St. Paul, MN (US); Shameem Sultana Syeda, St. Paul, MN (US)

(73) Assignees: The University of Kansas, Lawrence, KS (US); Regents of The University of Minnesota, St. Paul, MN (US)

( * ) Notice: Subject to any disclaimer, the term of this patent is extended or adjusted under 35 U.S.C. 154(b) by 274 days.

(21) Appl. No.: 13/932,778

(22) Filed: Jul. 1, 2013

(65) Prior Publication Data

US 2014/0005132 A1 Jan. 2, 2014

Related U.S. Application Data

(60) Provisional application No. 61/667,240, filed on Jul. 2, 2012.

(51) Int. Cl.
| | |
|---|---|
| *A61K 31/58* | (2006.01) |
| *C07J 43/00* | (2006.01) |
| *C07J 71/00* | (2006.01) |
| *C07J 19/00* | (2006.01) |
| *C07J 17/00* | (2006.01) |
| *C07C 281/18* | (2006.01) |
| *C07C 247/14* | (2006.01) |
| *C07C 49/653* | (2006.01) |
| *C07C 49/757* | (2006.01) |
| *C07D 249/04* | (2006.01) |
| *C07D 249/06* | (2006.01) |
| *C07J 1/00* | (2006.01) |
| *C07J 7/00* | (2006.01) |
| *C07J 41/00* | (2006.01) |
| *C07J 51/00* | (2006.01) |

(52) U.S. Cl.
CPC ........... *C07J 43/003* (2013.01); *C07C 49/653* (2013.01); *C07C 49/757* (2013.01); *C07C 247/14* (2013.01); *C07C 281/18* (2013.01); *C07D 249/04* (2013.01); *C07D 249/06* (2013.01); *C07J 17/005* (2013.01); *C07J 19/00* (2013.01); *C07J 19/005* (2013.01); *C07J 71/0026* (2013.01); *C07J 1/0011* (2013.01); *C07J 7/00* (2013.01); *C07J 7/002* (2013.01); *C07J 41/0005* (2013.01); *C07J 41/005* (2013.01); *C07J 41/0027* (2013.01); *C07J 51/00* (2013.01)

(58) Field of Classification Search
CPC ........ C07J 43/003; C07J 17/00; C07J 17/005; C07J 19/00; C07J 19/005; C07J 71/0026; A61K 31/58

USPC ...................... 540/61, 96; 514/172, 174, 176
See application file for complete search history.

(56) References Cited

PUBLICATIONS

Templeton et al., "Pregnane and 21-norpregnane derivatives of ouabain that bind to the digitalis receptor." European Journal of Medicinal Chemistry, vol. 29(10), pp. 799-804. Abstract attached.*
Becker et al., "Steroids. XXIX. Ouabagenin (II)", Justus Liebigs Annalen der Chemie, vol. 608, pp. 54-70, 1957. English Abstract only.*
Chen et al., "Synthetic derivatives of strophanthidin", J. Pharmacol., vol. 76, pp. 81-88, 1942 (Abstract attached).*

* cited by examiner

*Primary Examiner* — Barbara P Badio
(74) *Attorney, Agent, or Firm* — Maschoff Brennan

(57) ABSTRACT

The invention provides compounds of formula I, II, III, or IV:

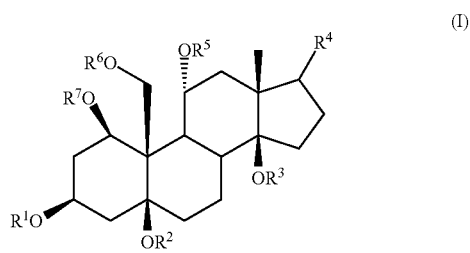

(I)

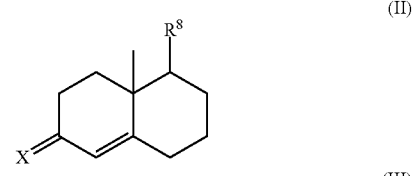

(II)

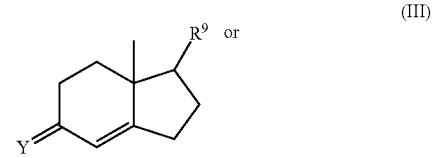

(III)

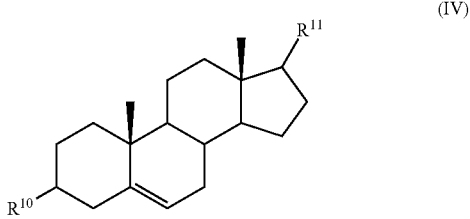

(IV)

wherein $R^1$ to $R^{11}$, X, and Y have any of the values defined in the specification. The compounds inhibit Na, K-ATPase α4 and are useful as contraceptive agents.

20 Claims, 5 Drawing Sheets

CONTRACEPTIVE AGENTS

CROSS-REFERENCE TO RELATED APPLICATIONS

This patent application claims the benefit of U.S. Provisional Application No. 61/667,240 filed Jul. 2, 2012, which application is incorporated herein by specific reference in its entirety.

GOVERNMENT FUNDING

This invention was made with government support under 1U54-HD055763 awarded by the National Institutes of Health. The government has certain rights in the invention.

BACKGROUND

The rapidly growing world population and the high rate of unintended pregnancies make contraception a need and a priority of any public health program. Although several contraceptive methods for women are currently available, it is clear that a more comprehensive approach requires extending contraception to males. However, at present, a safe, effective and reversible contraceptive for men is still unavailable.

The Na,K-ATPase is a protein complex of the cell plasma membrane that uses the free energy from the hydrolysis of ATP to transport $Na^+$ out of the cell in exchange for $K^+$. The transmembrane gradients of $Na^+$ and $K^+$ that the Na,K-ATPase generates are basic for cell survival and are involved in numerous essential cell processes, including cell osmotic balance and volume, cell pH and cell resting membrane potential. The Na,K-ATPase is an heterodimer composed of different molecular forms or isoforms of two main polypeptides, the α and β subunits. The α polypeptide constitutes the catalytic subunit of the Na,K-ATPase, directly involved in coupling ATP hydrolysis to the transport of ions. The β subunit acts as a chaperone protein, controlling the proper folding and trafficking of the α subunit to the plasma membrane. While the presence of an active $Na^+$ and $K^+$ transport system in spermatozoa has been known for some time, it was not until recently, that a novel isoform of Na,K-ATPase, the α4 polypeptide, was discovered in spermatozoa. The α4 isoform is only found in the testis, where it is exclusively expressed in male germ cells after meiosis. The α4 isoform has functional characteristics which are different from the α1 and other Na,K-ATPases, including a remarkably high affinity for ouabain, which is 10,000 fold higher than that of the ubiquitous α1 isoform. Activity of α4 is important for maintaining sperm intracellular $Na^+$ concentration, pH and membrane potential and it is necessary for sperm motility. In addition, recent studies using mouse models have shown that α4 is essential for male fertility.

Currently there is a need for effective and reversible contraceptive agents for men.

SUMMARY

Figure 1B:
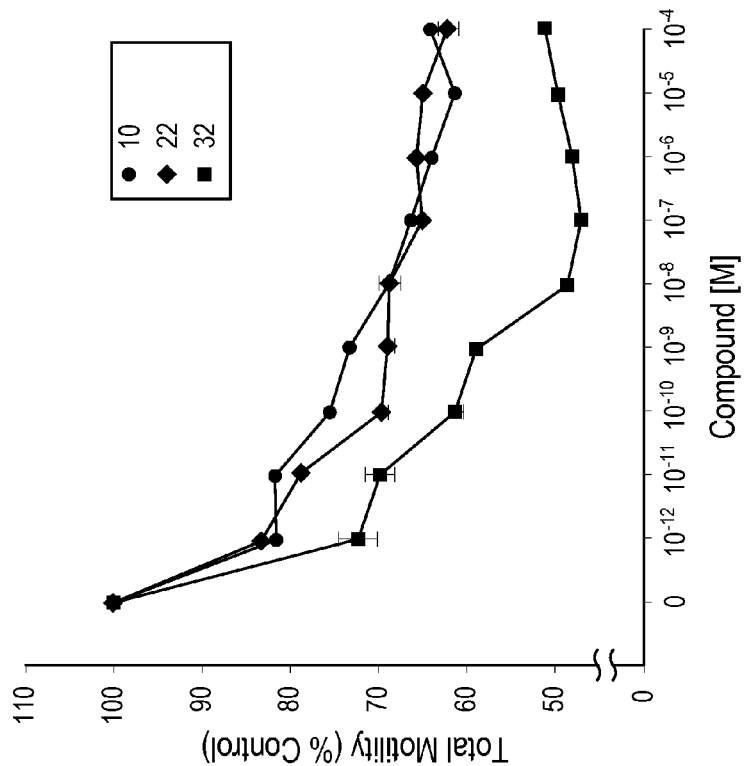
FIGS. 1A-1B includes graphs that illustrate dose and time response for the effect of compounds 8, 10, and 13 on sperm motility in Test B below.

The invention provides compounds which are useful as male contraceptives. Accordingly, in one embodiment the invention provides a compound of the invention which is a compound of formula I, II, III, or IV:

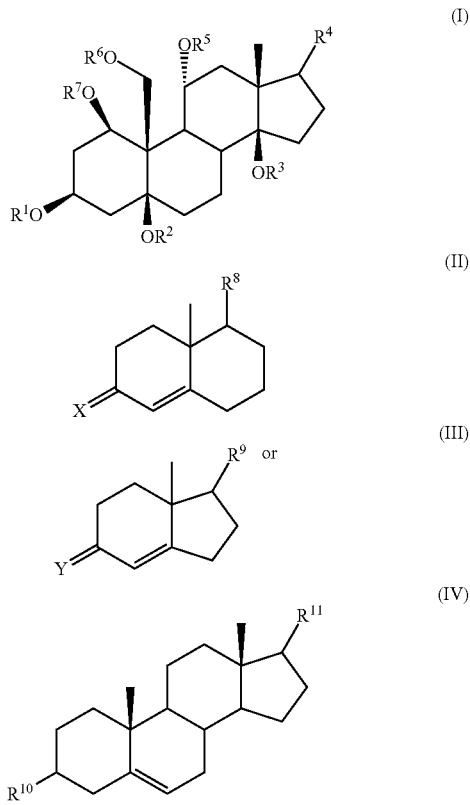

wherein:

$R^1$ is H, $(C_1-C_6)$alkyl, or $R_c$, wherein the $(C_1-C_6)$alkyl is optionally substituted with one or more halo or $(C_1-C_6)$alkoxy;

$R^2$ is H or $(C_1-C_6)$alkyl, wherein the $(C_1-C_6)$alkyl is optionally substituted with one or more halo or $(C_1-C_6)$alkoxy;

$R^3$ is H or $(C_1-C_6)$alkyl, wherein the $(C_1-C_6)$alkyl is optionally substituted with one or more halo or $(C_1-C_6)$alkoxy;

$R^4$ is $R_a$, cyano, carboxy, hydroximinomethyl, $(C_1-C_4)$alkyl, $(C_2-C_4)$alkenyl, $(C_2-C_4)$alkynyl, aryl, heteroaryl, or ($C_1$-$C_4$)alkanoyl, wherein the ($C_1$-$C_4$)alkyl, ($C_2$-$C_4$)alkenyl, ($C_2$-$C_4$)alkynyl, and ($C_1$-$C_4$)alkanoyl is optionally substituted with one or more groups selected from hydroxy, halo, aryl, and heteroaryl; wherein any aryl and heteroaryl of $R^4$ is optionally substituted with one or more $R_b$;

$R^5$ is H or ($C_1$-$C_6$)alkyl, wherein the ($C_1$-$C_6$)alkyl is optionally substituted with one or more halo or ($C_1$-$C_6$)alkoxy;

$R^6$ is H or ($C_1$-$C_6$)alkyl, wherein the ($C_1$-$C_6$)alkyl is optionally substituted with one or more halo or ($C_1$-$C_6$)alkoxy; and $R^7$ is H or ($C_1$-$C_6$)alkyl, wherein the ($C_1$-$C_6$)alkyl is optionally substituted with one or more halo or ($C_1$-$C_6$)alkoxy; or $R^6$ and $R^7$ taken together form a ($C_1$-$C_6$)alkylene;

$R^8$ is —CH=N—N=C($NH_2$)$_2$ or heteroaryl, which heteroaryl is optionally substituted with one or more $R_g$;

$R^9$ is —CH=N—N=C($NH_2$)$_2$ or heteroaryl, which heteroaryl is optionally substituted with one or more $R_h$;

X is O, or =N—N=C($NH_2$)$_2$;

Y is O, or =N—N=C($NH_2$)$_2$;

$R^{10}$ is —OH, morpholino, or —O—C(=O)CH($NH_2$)$R_k$, $R^{11}$ is $R_m$, aryl, or heteroaryl, wherein the aryl and heteroaryl of $R^{11}$ is optionally substituted with one or more $R_n$;

$R_a$, is a 4, 5, or 6 membered saturated or partially unsaturated heterocyclic ring comprising at least one carbon atom and at least one heteroatom selected from O, S, or NH in the ring, which ring is optionally substituted with one or more oxo (=O);

$R_b$, is aryl or aryl($C_1$-$C_6$)alkyl, wherein the aryl or aryl($C_1$-$C_6$)alkyl is optionally substituted with one or more ($C_1$-$C_6$)alkoxy or halo;

$R_c$, is a C-linked amino acid, a C-linked dipeptide, —C(=O)$CH_2CH_2$COOH, —P(=O)(OH)$_2$, or:

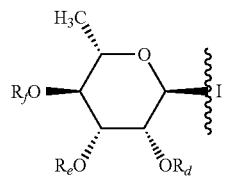

$R_d$ is H, ($C_1$-$C_6$)alkanoyl, or ($C_1$-$C_6$)alkyl, wherein the ($C_1$-$C_6$)alkanoyl and the ($C_1$-$C_6$)alkyl are each optionally substituted with one or more halo or ($C_1$-$C_6$)alkoxy; and $R_e$ is H, ($C_1$-$C_6$)alkanoyl, or ($C_1$-$C_6$)alkyl, wherein the ($C_1$-$C_6$)alkanoyl and the ($C_1$-$C_6$)alkyl are each optionally substituted with one or more halo or ($C_1$-$C_6$)alkoxy; or $R_d$ and $R_e$ taken together form a ($C_1$-$C_6$)alkylene; and $R_f$ is H, ($C_1$-$C_6$)alkanoyl, or ($C_1$-$C_6$)alkyl, wherein the ($C_1$-$C_6$)alkanoyl and the ($C_1$-$C_6$)alkyl are each optionally substituted with one or more halo or ($C_1$-$C_6$)alkoxy;

each $R_g$, is independently aryl or aryl($C_1$-$C_6$)alkyl, wherein the aryl or aryl($C_1$-$C_6$)alkyl is optionally substituted with one or more halo;

each $R_h$, is independently aryl or aryl($C_1$-$C_6$)alkyl, wherein the aryl or aryl($C_1$-$C_6$)alkyl is optionally substituted with one or more halo;

$R_k$ is H or ($C_1$-$C_6$)alkyl, wherein the ($C_1$-$C_6$)alkyl is optionally substituted with one or more halo, ($C_1$-$C_6$)alkoxy, benzyl, or amino;

$R_m$, is a 4, 5, or 6 membered saturated or partially unsaturated heterocyclic ring comprising at least one carbon atom and at least one heteroatom selected from O, S, or NH in the ring, which ring is optionally substituted with one or more oxo (=O); and $R_n$, is ($C_1$-$C_6$)alkyl, aryl, or aryl($C_1$-$C_6$)alkyl, wherein the ($C_1$-$C_6$)alkyl is optionally substituted with one or more halo, ($C_1$-$C_6$)alkoxycarbonyl, or ($C_1$-$C_6$)alkoxy; and wherein the aryl or aryl($C_1$-$C_6$)alkyl is optionally substituted with one or more halo;

or a salt thereof.

Accordingly, the term "a compound of the invention" as used herein includes compounds of formula I, II, III, and IV.

The invention also provides pharmaceutical composition comprising a compound of the invention or a pharmaceutically acceptable salt thereof and a pharmaceutically acceptable diluent or carrier.

The invention also provides a method for decreasing sperm motility in a mammal comprising administering a compound of the invention or a pharmaceutically acceptable salt thereof to the mammal.

The invention also provides a compound of the invention or a pharmaceutically acceptable salt thereof for use in medical therapy.

The invention also provides a compound of the invention or a pharmaceutically acceptable salt thereof for reducing sperm motility.

The invention also provides the use of a compound of the invention or a pharmaceutically acceptable salt thereof to prepare a medicament for reducing sperm motility in an mammal (e.g. a human).

The invention also provides processes and intermediates disclosed herein that are useful for preparing a compound of the invention, or a salt thereof.

DETAILED DESCRIPTION

The following definitions are used, unless otherwise described: halo is fluoro, chloro, bromo, or iodo. Alkyl, alkylene, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl). A C-linked amino acid is linked through the carbonyl group of the carboxylic acid.

The term "dipeptide" describes a sequence of 2 amino acids as defined hereinabove. A C-linked dipeptide is linked through the carbonyl group of the carboxylic acid. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butyryl, 3-butyryl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

As used herein, "$(C_1-C_6)$alkylene" is a divalent straight or branched hydrocarbon chain comprising 1, 2, 3, 4, 5, or 6 carbons.

In one embodiment the invention provides a compound of the invention which is a compound of formula I:

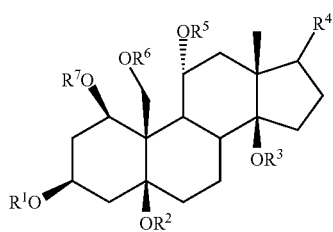

(I)

wherein:
$R^1$ is H, $(C_1-C_6)$alkyl, or $R_c$, wherein the $(C_1-C_6)$alkyl is optionally substituted with one or more halo or $(C_1-C_6)$alkoxy $R^2$ is H or $(C_1-C_6)$alkyl, wherein the $(C_1-C_6)$alkyl is optionally substituted with one or more halo or $(C_1-C_6)$alkoxy;

$R^3$ is H or $(C_1-C_6)$alkyl, wherein the $(C_1-C_6)$alkyl is optionally substituted with one or more halo or $(C_1-C_6)$alkoxy;

$R^4$ is $R_a$, cyano, $(C_1-C_3)$alkyl, $(C_2-C_4)$alkenyl, $(C_3-C_4)$alkynyl, aryl, heteroaryl, or $(C_1-C_3)$alkanoyl, wherein the $(C_1-C_3)$alkyl, $(C_2-C_4)$alkenyl, $(C_3-C_4)$alkynyl, and $(C_1-C_3)$alkanoyl is optionally substituted with one or more groups selected from hydroxy, halo, aryl, and heteroaryl; wherein any aryl and heteroaryl of $R^4$ is optionally substituted with one or more $R_b$;

$R^5$ is H or $(C_1-C_6)$alkyl, wherein the $(C_1-C_6)$alkyl is optionally substituted with one or more halo or $(C_1-C_6)$alkoxy; and $R^6$ is H or $(C_1-C_6)$alkyl, wherein the $(C_1-C_6)$alkyl is optionally substituted with one or more halo or $(C_1-C_6)$alkoxy; and $R^7$ is H or $(C_1-C_6)$alkyl, wherein the $(C_1-C_6)$alkyl is optionally substituted with one or more halo or $(C_1-C_6)$alkoxy; or $R^6$ and $R^7$ taken together form a $(C_1-C_6)$alkylene;

$R_a$, is a 4, 5, or 6 membered saturated or partially unsaturated heterocyclic ring comprising at least one carbon atom and at least one heteroatom selected from O, S, or NH in the ring, which ring is optionally substituted with one or more oxo (=O);

$R_b$, is aryl or aryl$(C_1-C_6)$alkyl, wherein the aryl or aryl $(C_1-C_6)$alkyl is optionally substituted with one or more halo; and $R_c$, is a C-linked amino acid, a C-linked dipeptide, —C(=O)CH$_2$CH$_2$COOH, —P(=O)(OH)$_2$, or:

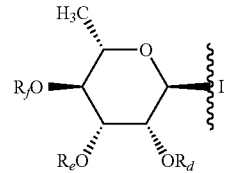

$R_d$ is H or $(C_1-C_6)$alkyl, wherein the $(C_1-C_6)$alkyl is optionally substituted with one or more halo or $(C_1-C_6)$alkoxy; and $R_e$ is H or $(C_1-C_6)$alkyl, wherein the $(C_1-C_6)$alkyl is optionally substituted with one or more halo or $(C_1-C_6)$alkoxy; or $R_d$ and $R_e$ taken together form a $(C_1-C_6)$alkylene; and $R_f$ is H or $(C_1-C_6)$alkyl, wherein the $(C_1-C_6)$alkyl is optionally substituted with one or more halo or $(C_1-C_6)$alkoxy;

or a salt thereof.

In one embodiment the invention provides a compound of the invention which is a compound of formula II or III:

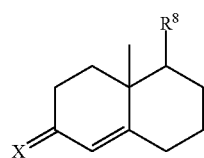

(II)

-continued

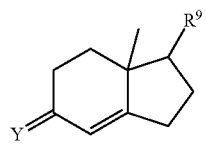

(III)

wherein:
R⁸ is —CH=N—N=C(NH₂)₂ or heteroaryl, which heteroaryl is optionally substituted with one or more $R_g$;
R⁹ is —CH=N—N=C(NH₂)₂ or heteroaryl, which heteroaryl is optionally substituted with one or more $R_h$;
X is O, or =N—N=C(NH₂)₂;
Y is O, or =N—N=C(NH₂)₂;
each $R_g$, is independently aryl or aryl(C₁-C₆)alkyl, wherein the aryl or aryl(C₁-C₆)alkyl is optionally substituted with one or more halo; and
each $R_h$, is independently aryl or aryl(C₁-C₆)alkyl, wherein the aryl or aryl(C₁-C₆)alkyl is optionally substituted with one or more halo;
or a salt thereof.

In one embodiment the invention provides a compound of the invention which is a compound of formula IV:

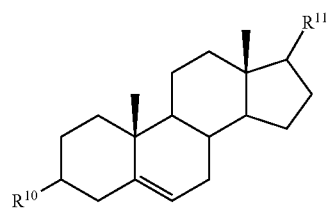

(IV)

wherein:
R¹⁰ is —OH, morpholino, or —O—C(=O)CH(NH₂)$R_k$,
R¹¹ is $R_m$, aryl, or heteroaryl, wherein the aryl and heteroaryl of R⁴ is optionally substituted with one or more $R_n$;
$R_k$ is H or (C₁-C₆)alkyl, wherein the (C₁-C₆)alkyl is optionally substituted with one or more halo, (C₁-C₆)alkoxy, benzyl, or amino;
$R_m$, is a 4, 5, or 6 membered saturated or partially unsaturated heterocyclic ring comprising at least one carbon atom and at least one heteroatom selected from O, S, or NH in the ring, which ring is optionally substituted with one or more oxo (=O); and
$R_n$, is (C₁-C₆)alkyl, aryl, or aryl(C₁-C₆)alkyl, wherein the (C₁-C₆)alkyl is optionally substituted with one or more halo, (C₁-C₆)alkoxycarbonyl, or (C₁-C₆)alkoxy; and wherein the aryl or aryl(C₁-C₆)alkyl is optionally substituted with one or more halo;
or a salt thereof.

A specific value for R¹ is H, methoxymethyl,

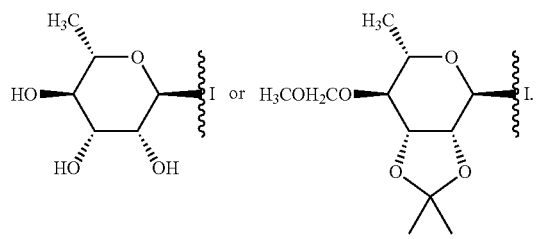

A specific value for R² is H.

A specific value for R³ is H or methoxymethyl.

A specific value for R⁴ is 1,2-dihydroxyethyl, formyl, cyano, hydroxymethyl, ethynyl, carboxy, 2,2,2-trifluoro-1-hydroxyethyl, hydroximinomethyl,

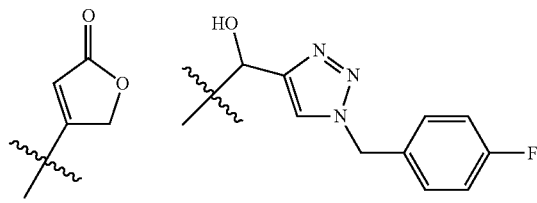

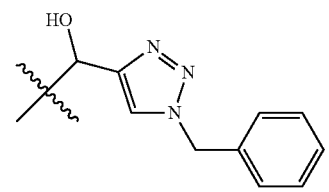

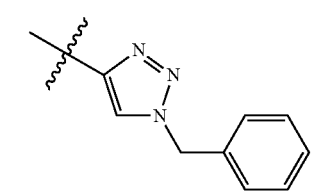

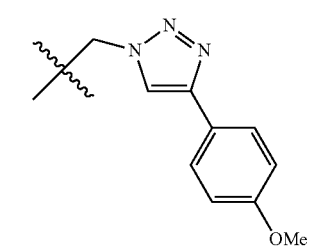

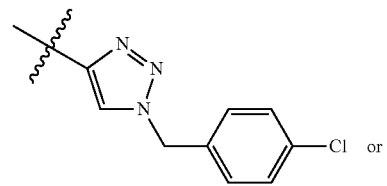 or

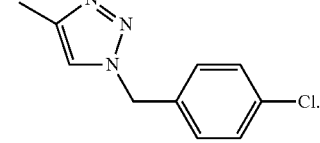

A specific value for R⁵ is H or methoxymethyl.

A specific value for R⁶ is H.

A specific value for R⁷ is H.

A specific value for R⁶ and R⁷ taken together form —C(CH₃)₂—.

A specific value for $R^8$ is —CH=N—N=C(NH$_2$)$_2$ or

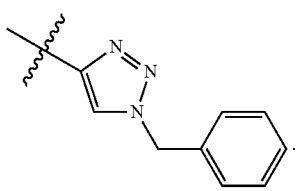 [SMILES: *c1cn(Cc2ccccc2)nn1 ; "."]

A specific value for $R^9$ is —CH=N—N=C(NH$_2$)$_2$,

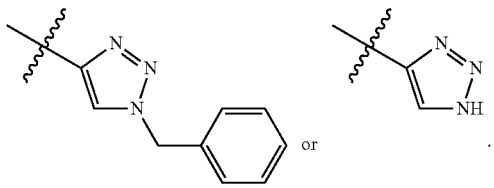 [SMILES: *c1cn(Cc2ccccc2)nn1 ; "or" ; *c1c[nH]nn1 ; "."]

A specific value for X is O.
A specific value for X is =N—N=C(NH$_2$)$_2$.
A specific value for Y is O.
A specific value for Y is =N—N=C(NH$_2$)$_2$.
A specific value for $R^{10}$ is —OH, morpholino, or —O—C(=O)CH(NH$_2$)$R_k$; and $R_k$ is 1-methylethyl or 4-aminobutyl.
A specific value for $R^{11}$ is

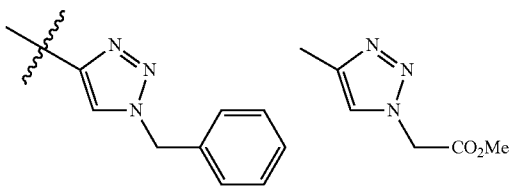

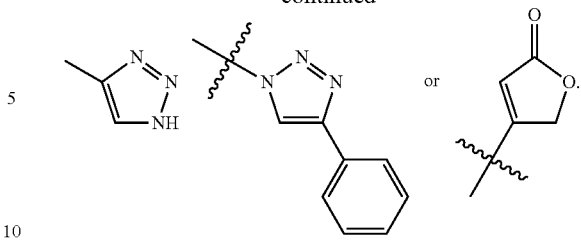

In one embodiment of the invention the compound is not Compound 54, 12, 1 or 1a (see Sevillano et al., *J. Med. Chem.* 2002, 45, 127-136 and *Bioorg. Med. Chem.* 1999, 7, 2991-3001; Sneeden et al., *J. Am. Chem. Soc.,* 1953, 75, 3510-3513; Hong et al., *Tetrahedron Lett.* 2006, 47, 2711-2715; and Hatakeyama et al., *J. Am. Chem. Soc.,* 2006, 128, 2518-2519, which are incorporated herein by specific reference in their entirety).

Processes for preparing compounds of the invention and salts thereof are provided as further embodiments of the invention and are illustrated by the following procedures in which the meanings of the generic radicals are as given above unless otherwise qualified.

The following schemes describe the general synthetic routes for the preparation of formula I, II, III and IV compounds in the present invention. The other representative compounds, stereoisomers, enantiomers, diastereomers and racemic mixtures can be prepared from intermediates synthesized in accordance to the general schemes.

Scheme A

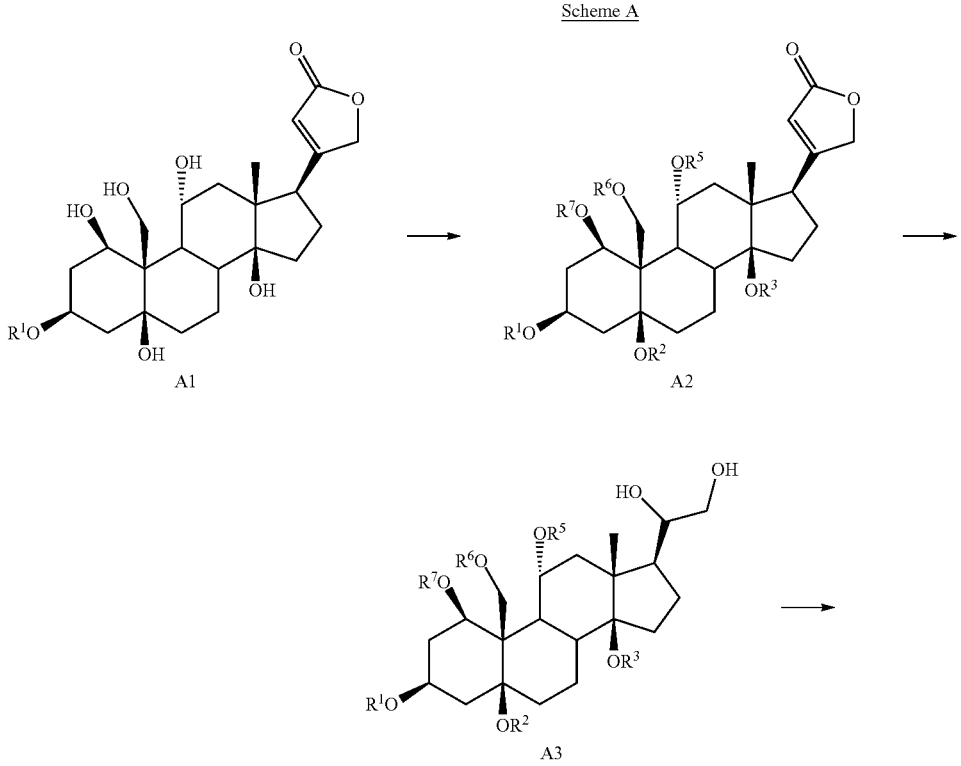

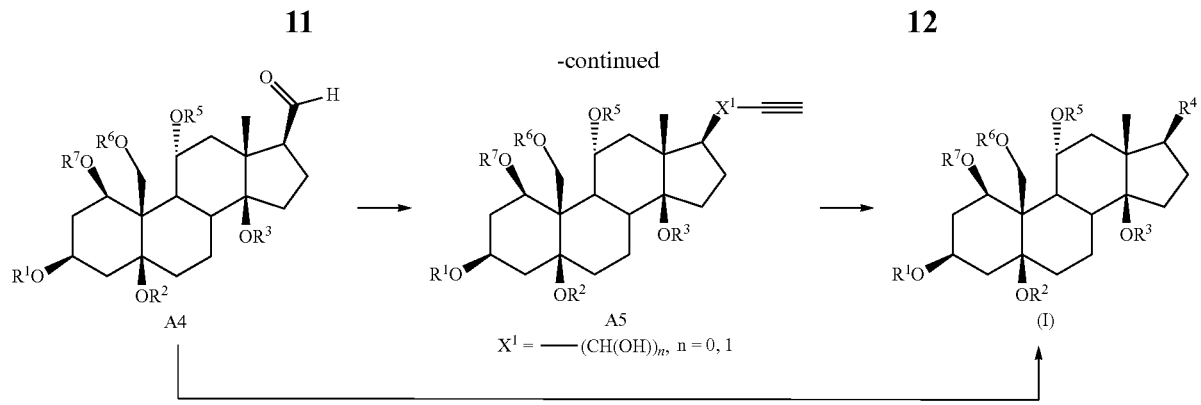

Scheme A illustrates the general method for the synthesis of formula I compounds in the present invention. Compound A1, where $R^1$ is previously defined, is commercially available or can be prepared using known literature procedure (Sneeden et al., *J. Am. Chem. Soc.*, 1953, 75, 3510-3513.). Compound A1 can be converted to A2 by protecting of hydroxyl groups, where $R^2$, $R^3$, $R^4$, $R^5$, $R^6$ are previously defined. Ozolalysis of A2 followed by reduction with sodium borohydride provides compound A3. Compound A3 may undergo oxidative cleavage with sodium periodate to get A4. Compound A4 can be converted to the formula I compounds by oxime formation or oxime-dehydration or oxidation or reduction or reduction-tosylation-azidation-click chemistry. In another method A4 may also converted to A5 with Bestmann reagent or ethynylmagnesium bromide, which would then, transformed into formula I compounds by click chemistry with various azides.

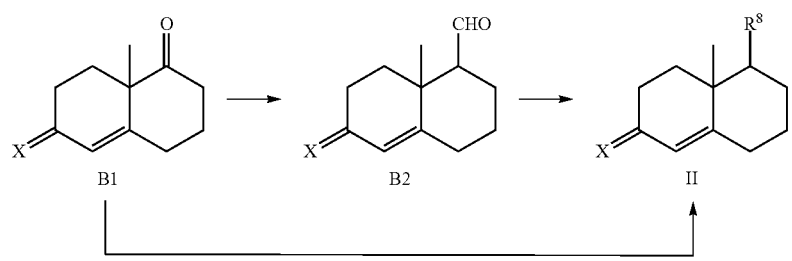

Scheme B represents the general synthetic route for the formula II compounds in the present invention. Compound B1, (where X is previously defined) may be converted to B2 using reported procedure (Paquett e et al., *J. Am. Chem. Soc.*, 1994, 116, 3367-3374, which is incorporated herein by specific reference in its entirety). Formula II compounds can be prepared from B1 by treatment with Bestmann reagent and click chemistry with various azides or hydrazone formation. Formula II compounds can also be synthesized from B1 by the sequence involved reduction, Mitsnobu azidation and click chemistry with alkynes.

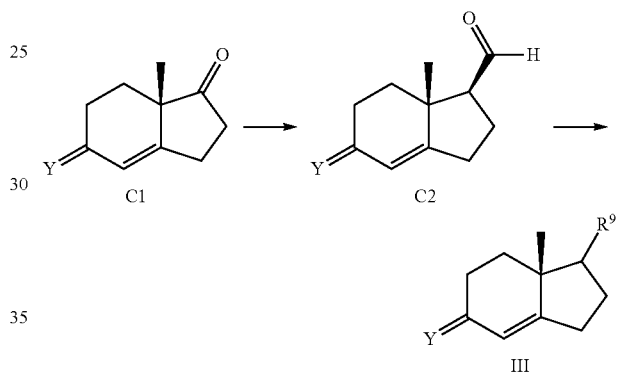

As describe in scheme C, formula III compounds may be synthesized from commercially available C1 (where Y is previously defined). Compound C2 may be prepared from C1 using reported method (Sevillano et al., *J. Med. Chem.* 2002, 45, 127-136 and *Bioorg. Med. Chem.* 1999, 7, 2991-3001, which is incorporated herein by specific reference in its entirety). The formula III compounds can be derived from C2 by alkyne introduction and click chemistry or bis hydrazone formation.

Scheme D

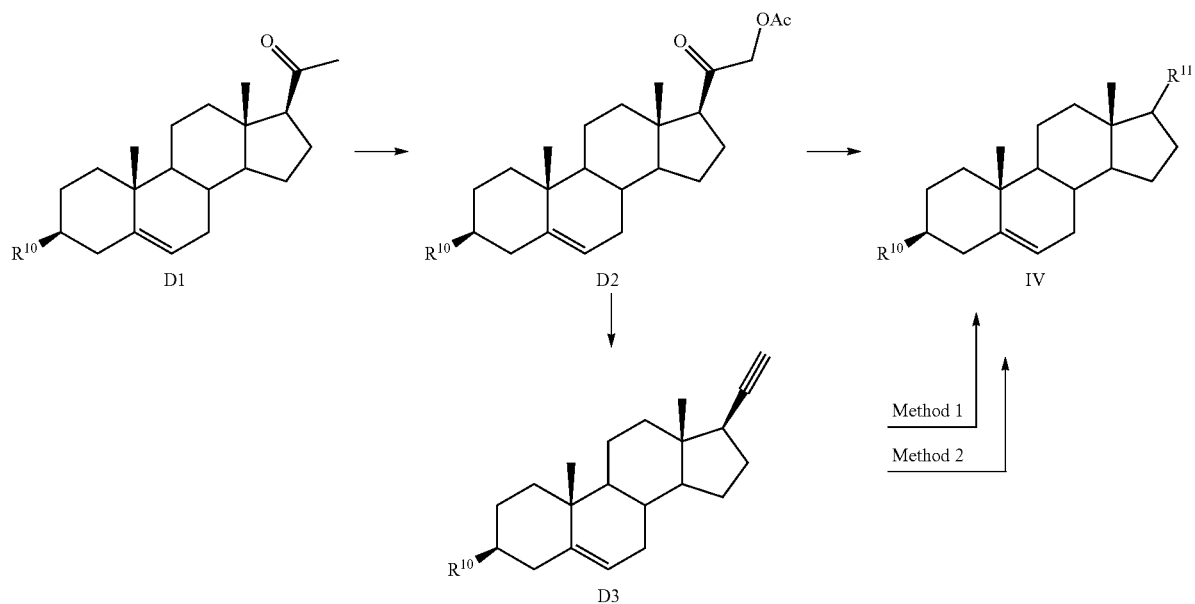

As depicted in scheme D, formula IV compounds can be prepared from commercially available compound D1 (where, R¹⁰ was previously defined). Compound D1 can be converted to D2 using reported method (*J. Med. Chem.* 1990, 33, 1572-1581, which is incorporated herein by specific reference in its entirety). Formula IV compounds in this present invention can be prepared from D2 by reaction with ketene. In another method compound D2 may be converted to D3 by a sequence involved reduction, oxidative cleavage and Corey-Fuchs reaction. Compound D3 can be derived to formula IV compounds using click chemistry with azides (method 1). In another method (method 2) compound D3 is converted to the corresponding amino esters with various amino acids and then subjected to click chemistry to get formula IV compounds.

Scheme E

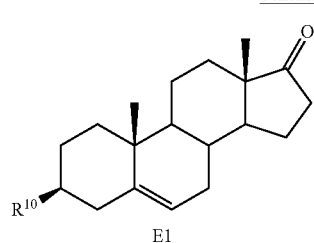

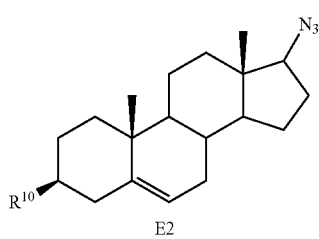

-continued

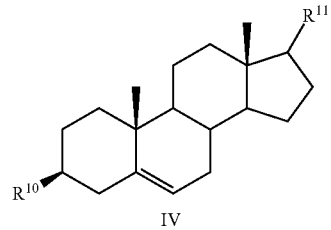

Scheme E shows the synthetic route for another set of formula IV compounds. Commercially available compound E1 (where, R¹⁰ was previously defined) may be converted to E2 by reduction and Mitsnobu azidation or reduction, Mitsnobu inversion and Mitsnobu azidation, which can be subjected to click chemistry with alkynes to get formula IV compounds.

General Schemes I-IV below also illustrate general methods that can be used to prepare compounds of the invention.

General Scheme I

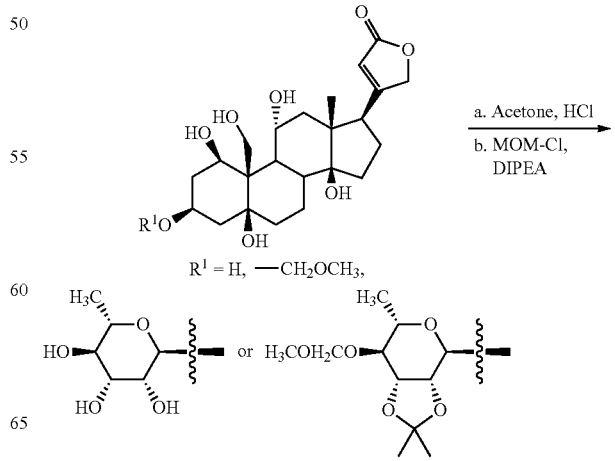

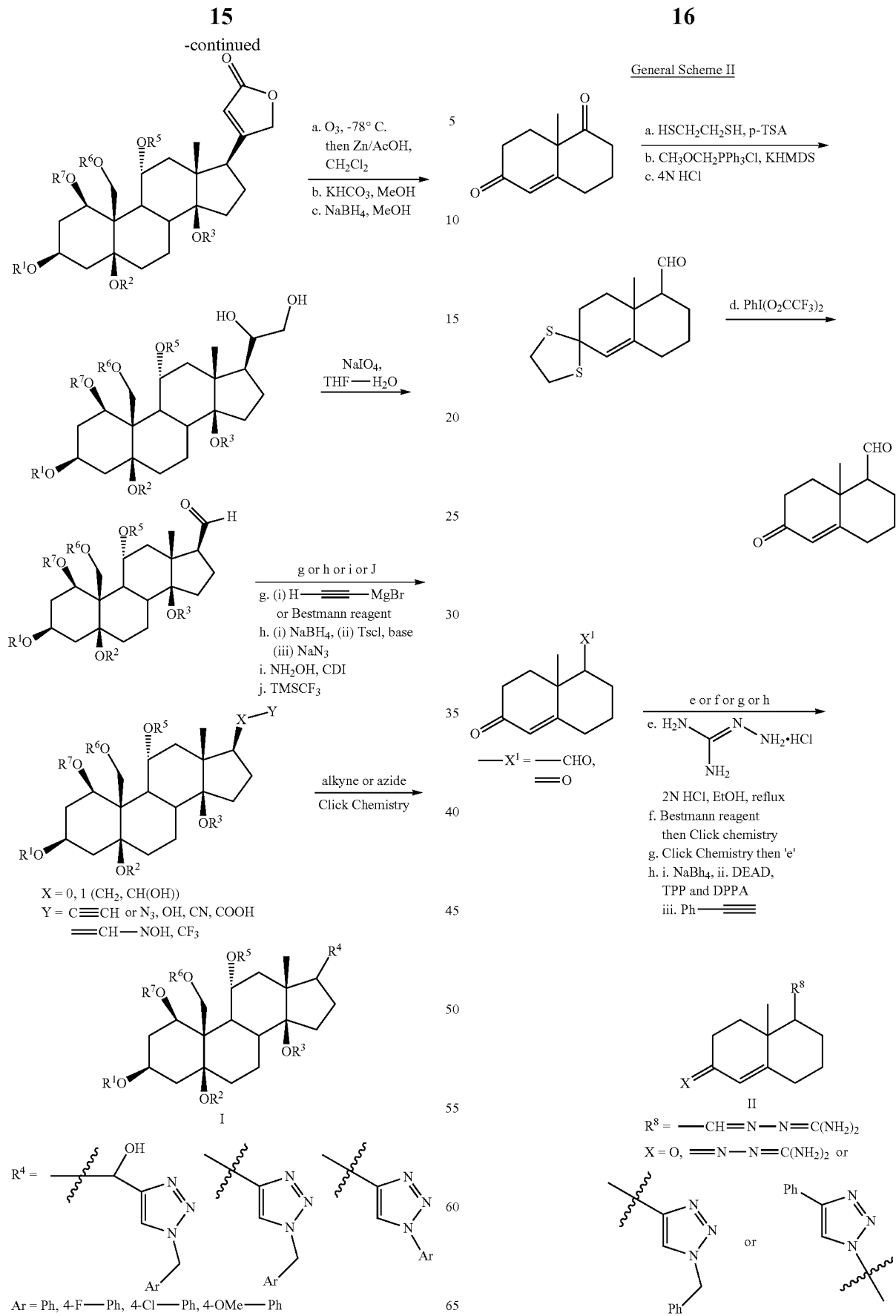

General Scheme III
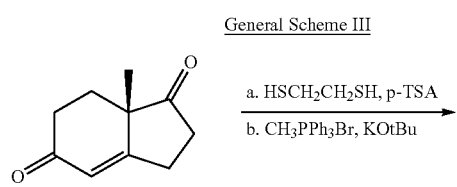
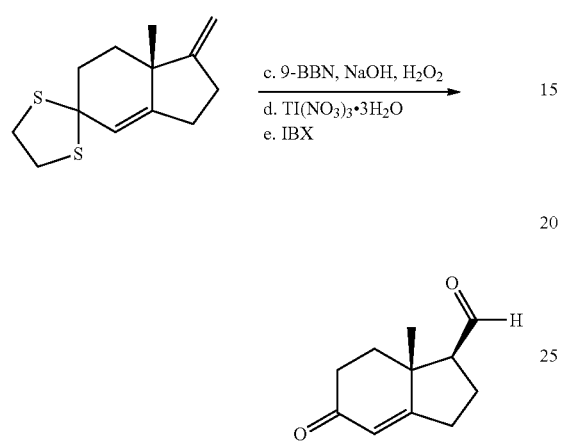
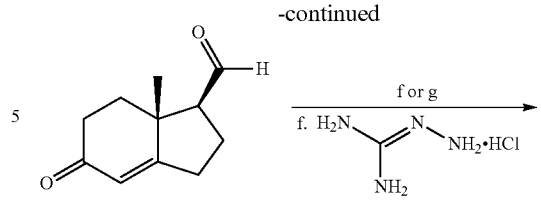
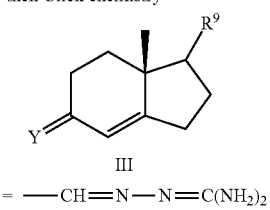
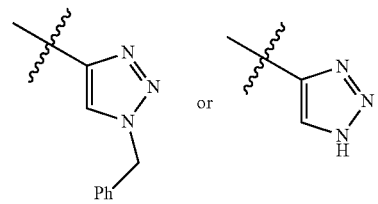
Scheme IVA
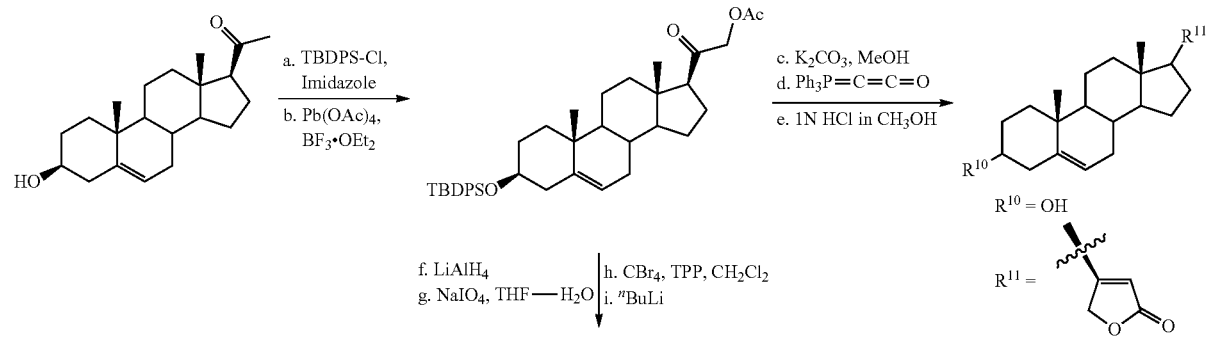
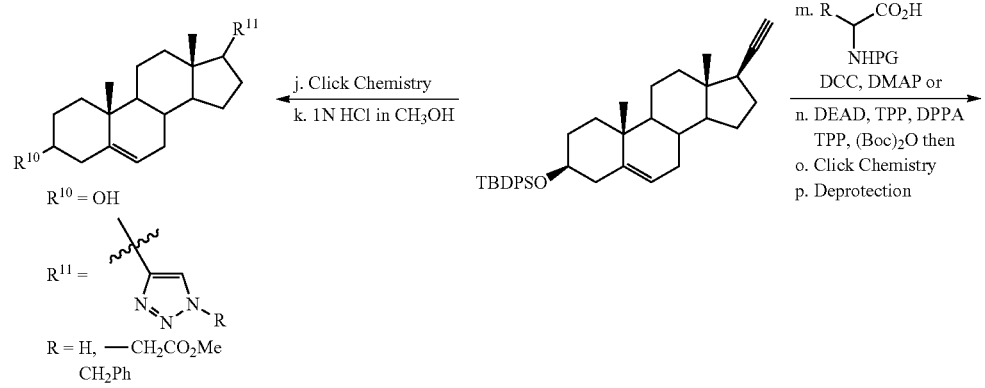

-continued

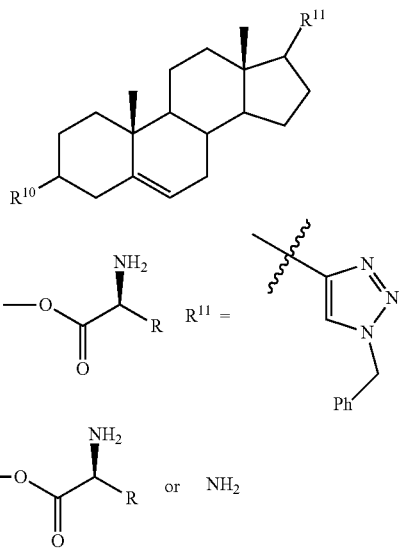

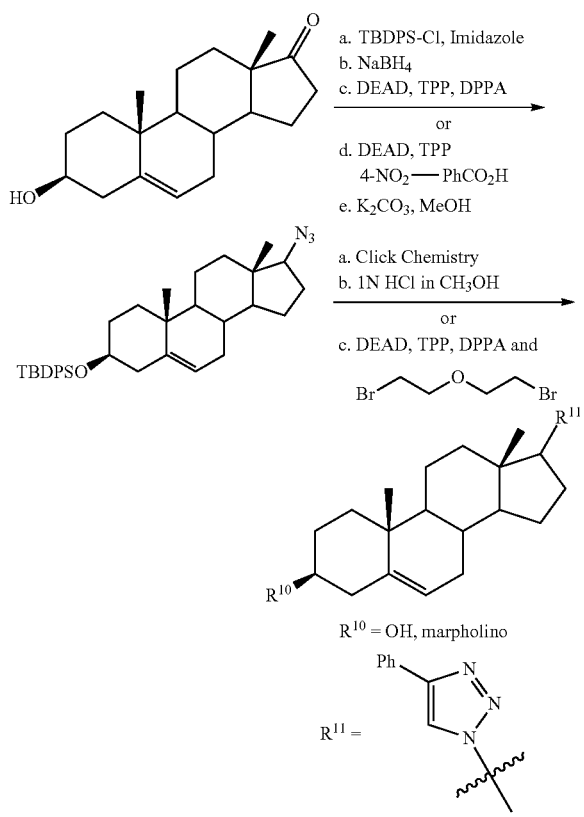

Scheme IVB

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), which are incorporated herein by specific reference in their entirety.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is incorporated herein by specific reference in its entirety.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to modulate Na,K-ATPase activity may be determined using pharmacological models which are well known to the art, or using Test A described below.

Test A. Na,K-ATPase Assays

The effect of synthetic compounds is determined on the Na,K-ATPase activity of insect cells (Sf9 cells) expressing the Na,K-ATPase α4 isoform. Homogenates from these cells are used and the initial rate of release of $^{32}P_i$ from $\gamma[^{32}P]$-ATP is tested. Na,K-ATPase was assayed in a final volume of 0.25 ml in medium containing 120 mM NaCl, 30 mM KCl, 3 mM $MgCl_2$, 0.2 mM EGTA, 30 mM Tris-HCl (pH 7.4), 3 mM ATP with 0.2 μCi $\gamma[^{32}P]$-ATP in the presence and absence of different concentrations of each compound (0, $10^{-10}$, $10^{-9}$, $10^{-8}$, $10^{-7}$, $10^{-6}$, $10^{-5}$, $10^{-4}$ M). Samples are incubated for 30 min at 37° C., reaction is stopped with 5% trichloroacetic acid and released $^{32}$Pi-Pi is converted to phosphomolybdate with ammonium molibdate. The $^{32}$Pi-Pi is extracted with isobutanol and radioactivity of 170 μl of the organic phase is measured by liquid scintillation counting. Specific overall Na,K-ATPase activity is determined as the difference in ATP hydrolysis in the absence and presence of 1 mM ouabain, which is known to completely block Na,K-ATPase activity. Curve fitting of the experimental data and calculation of IC50 values is performed using a Marquardt least-squares non-linear regression computing program (Sigma Plot, Jandel Scientific, San Rafael, Calif.).

Results for the effect of representative compounds of the invention on Na,K-ATPase activity are provided in Table 1.

TABLE 1

| Compound | Structure | Ki (M) |
| --- | --- | --- |
| 12 | 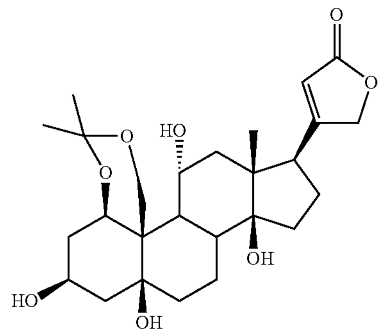 | *N.T |
| 1a | 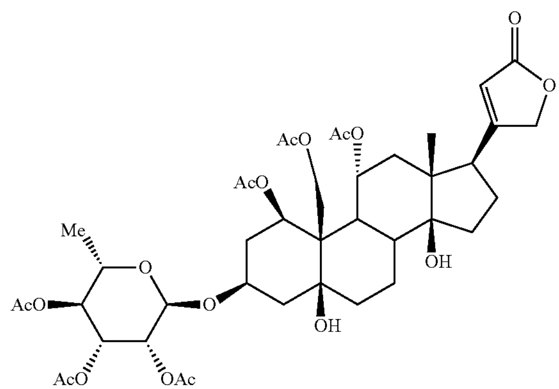 [SMILES: CC(=O)OC[C@@]12C3C(CC[C@]1(O)C[C@@H](O[C@@H]1O[C@@H](C)[C@H](OC(C)=O)[C@@H](OC(C)=O)[C@H]1OC(C)=O)C[C@H]2OC(C)=O)[C@@]1(O)CC[C@H](C2=CC(=O)OC2)[C@@]1(C)C[C@H]3OC(C)=O] | *N.T |
| 1 | 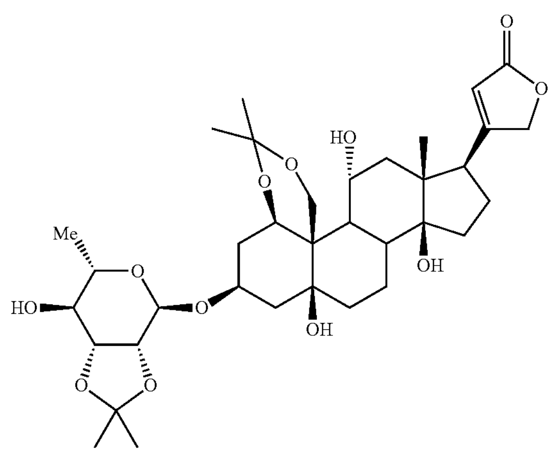 [SMILES: C[C@@H]1O[C@@H](O[C@H]2C[C@H]3OC(C)(C)OC[C@]34C3C(CC[C@]4(O)C2)[C@@]2(O)CC[C@H](C4=CC(=O)OC4)[C@@]2(C)C[C@H]3O)[C@@H]2OC(C)(C)O[C@@H]2[C@H]1O] | 8.6 ± 5.5 × 10$^{-9}$ M |
| 3 | 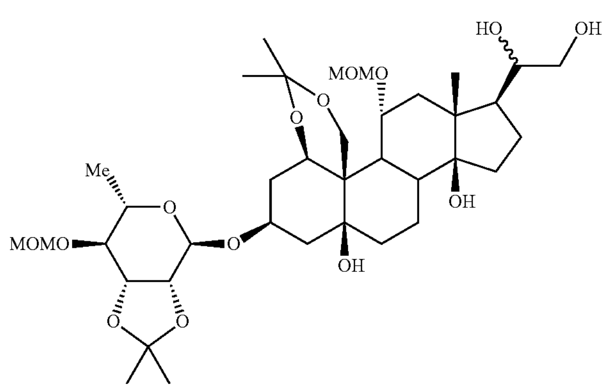 | 1.1 ± 1.0 × 10$^{-5}$ M |

TABLE 1-continued

| Compound | Structure | Ki (M) |
|---|---|---|
| 4 | 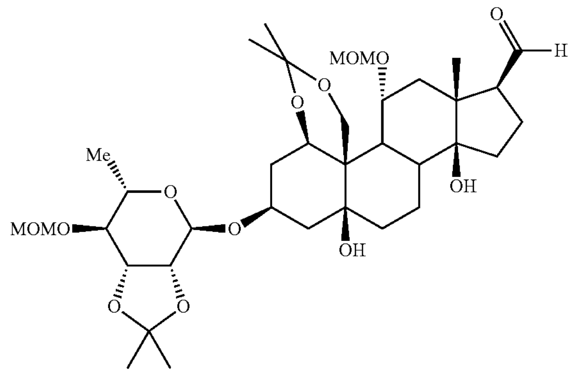 | $1.9 \pm 5.2 \times 10^{-9}$ M |
| 11 | 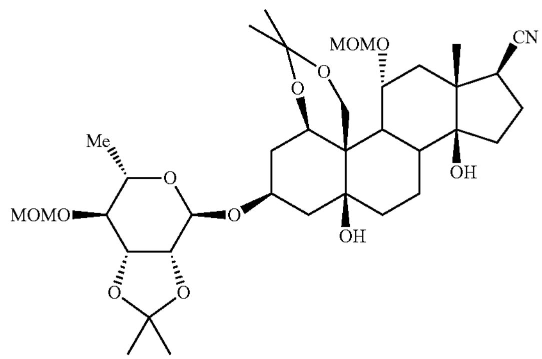 | $4.5 \pm 3.6 \times 10^{-8}$ M |
| 6 | 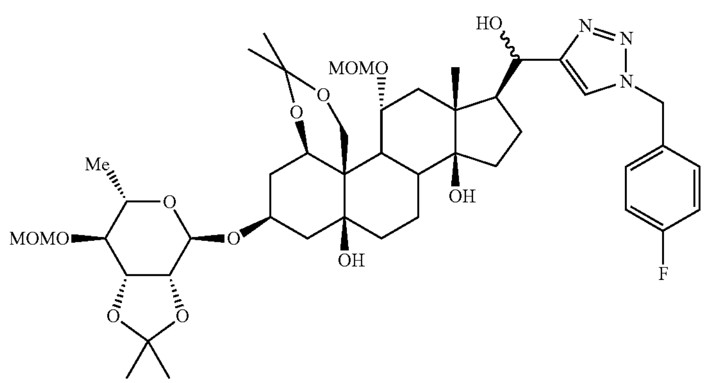 | $5.4 \pm 7.2 \times 10^{-9}$ M |
| 10 | 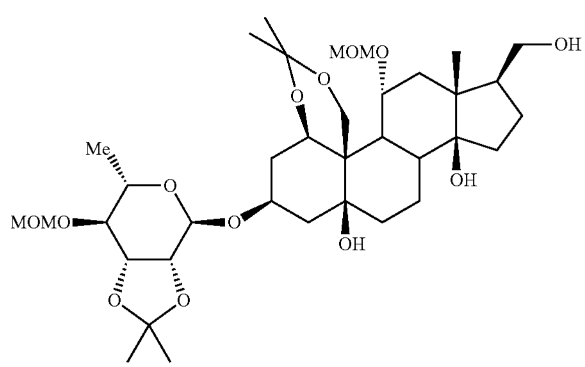 | $1.2 \pm 2.0 \times 10^{-9}$ M |

TABLE 1-continued

| Compound | Structure | Ki (M) |
|---|---|---|
| 28 | 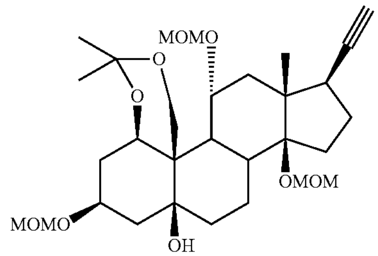 | *N.T |
| 22 | 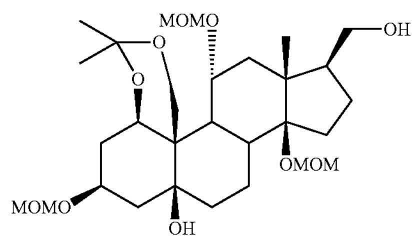 | 2.4 ± 3.7 × 10$^{-10}$ M |
| 17 | 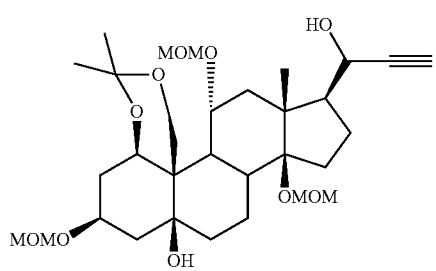 | 1.1 ± 0.5 × 10$^{-7}$ M |
| 9 | 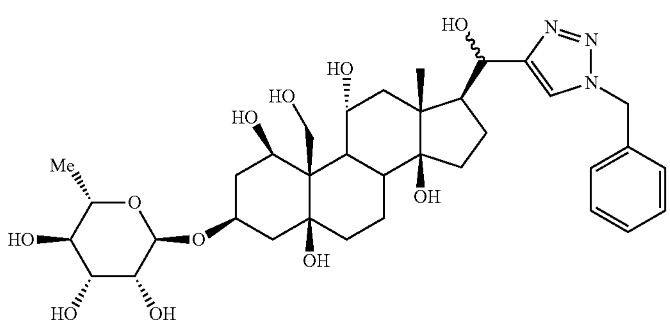 [SMILES: C[C@@H]1O[C@@H](O[C@H]2C[C@@H](O)[C@]3(CO)C4C(CC[C@]3(O)C2)[C@@]2(O)CC[C@H](C(O)c3cn(Cc5ccccc5)nn3)[C@@]2(C)C[C@H]4O)[C@H](O)[C@H](O)[C@H]1O] | 1.1 ± 0.7 × 10$^{-6}$ M |
| 32 | 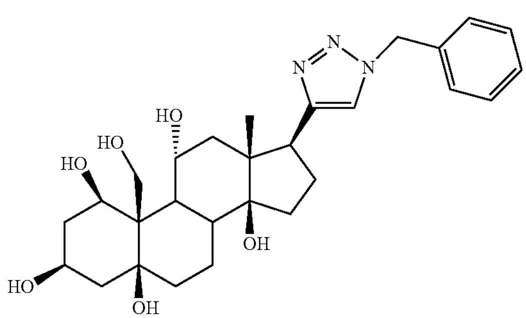 [SMILES: C[C@]12C[C@@H](O)C3C(CC[C@]4(O)C[C@@H](O)C[C@@H](O)[C@]34CO)[C@@]1(O)CC[C@@H]2c1cn(Cc2ccccc2)nn1] | 5.3 ± 5.1 × 10$^{-12}$ M |

TABLE 1-continued

| Compound | Structure | Ki (M) |
|---|---|---|
| 8 | 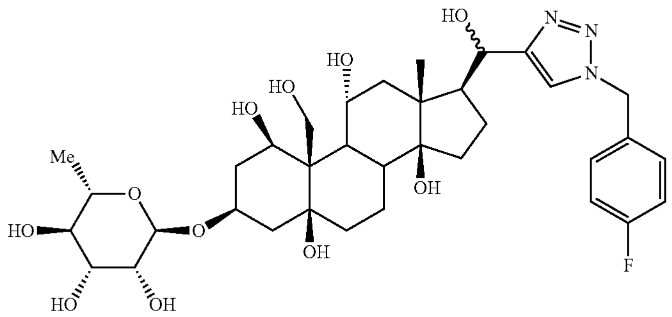 [SMILES: C[C@@H]1O[C@@H](O[C@H]2C[C@@H](O)[C@]3(CO)C4C(CC[C@]3(O)C2)[C@@]2(O)CC[C@H](C(O)c3cn(Cc5ccc(F)cc5)nn3)[C@@]2(C)C[C@H]4O)[C@H](O)[C@H](O)[C@H]1O] | $3.7 \pm 0.9 \times 10^{-8}$ M |
| 26 | 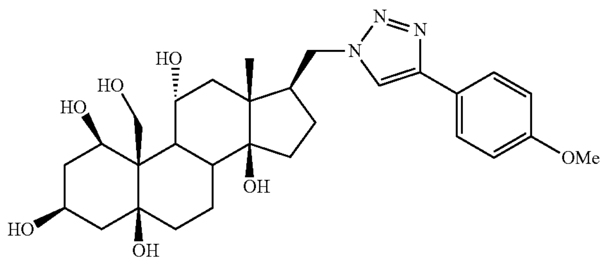 [SMILES: COc1ccc(-c2cn(C[C@H]3CC[C@]4(O)C5CC[C@]6(O)C[C@@H](O)C[C@@H](O)[C@]6(CO)C5[C@H](O)C[C@]34C)nn2)cc1] | $2.7 \pm 10.1 \times 10^{-3}$ M |
| 38 | 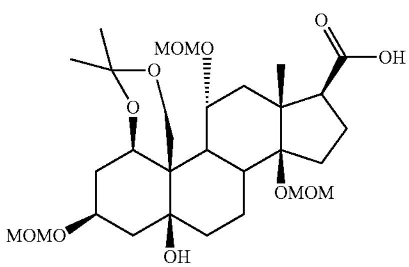 | $8.4 \pm 5.9 \times 10^{-8}$ M |
| 36 | 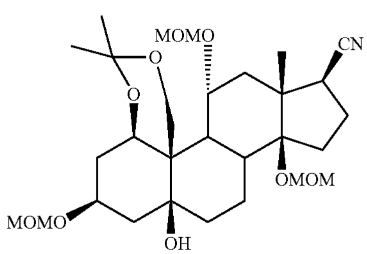 | $5.5 \pm 1.7 \times 10^{-4}$ M |
| 37 | 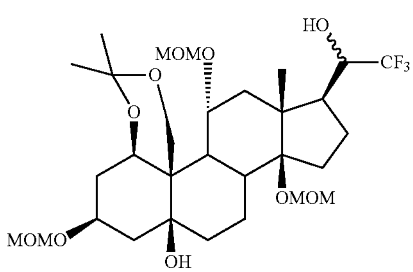 | $6.2 \pm 6.0 \times 10^{-6}$ M |

TABLE 1-continued

| Compound | Structure | Ki (M) |
|---|---|---|
| 35 | 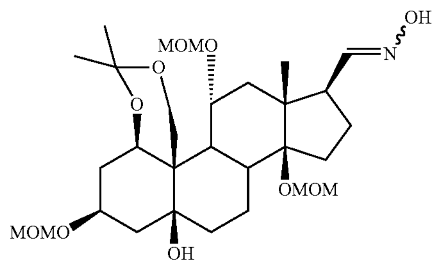 | $2.4 \pm 3.4 \times 10^{-9}$ M |
| 42 | (+/−) | $8.7 \pm 5.9 \times 10^{-8}$ M |
| 54 | 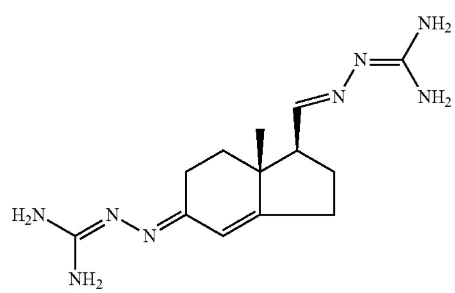 [SMILES: C[C@]12CC/C(=N\N=C(N)N)C=C1CC[C@@H]2/C=N/N=C(N)N] | $1.1 \pm 0.9 \times 10^{-6}$ M |
| 56 | 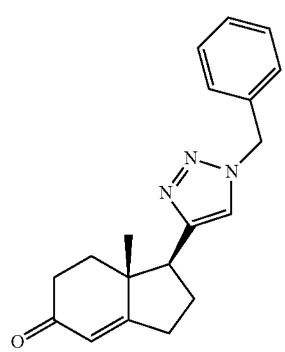 [SMILES: C[C@]12CCC(=O)C=C1CC[C@@H]2c1cn(Cc2ccccc2)nn1] | $1.0 \pm 0.2 \times 10^{-8}$ M |
| 58 | 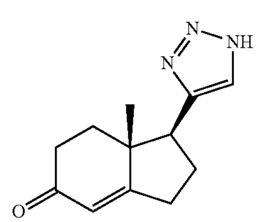 [SMILES: C[C@]12CCC(=O)C=C1CC[C@@H]2c1c[nH]nn1] | $6.9 \pm 4.9 \times 10^{-9}$ M |

TABLE 1-continued

| Compound | Structure | Ki (M) |
|---|---|---|
| 29 | 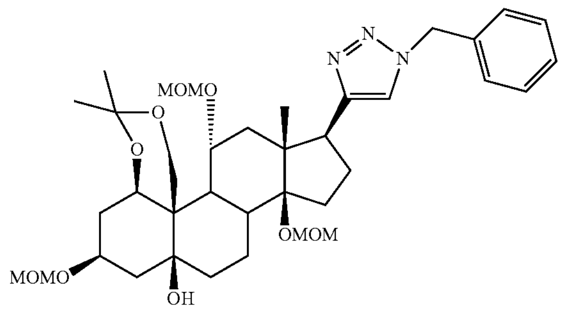 | $8.5 \pm 7.7 \times 10^{-9}$ M |
| 44 | (+/-) | *N.T |
| 33 | 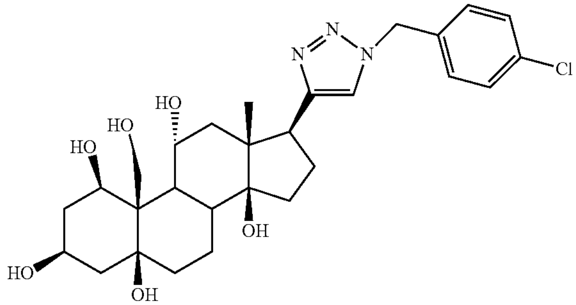 [SMILES: C[C@]12C[C@@H](O)C3C(CC[C@]4(O)C[C@@H](O)C[C@@H](O)[C@]34CO)[C@@]1(O)CC[C@@H]2c1cn(Cc2ccc(Cl)cc2)nn1] | $1.9 \pm 1.4 \times 10^{-8}$ M |
| 34 | 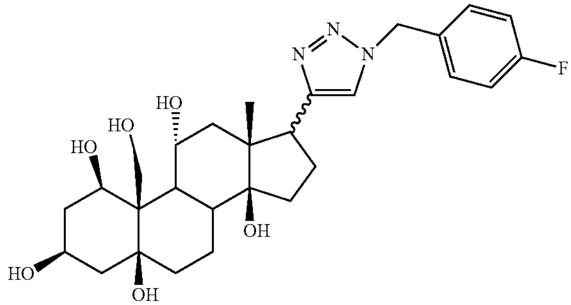 [SMILES: C[C@]12C[C@@H](O)C3C(CC[C@]4(O)C[C@@H](O)C[C@@H](O)[C@]34CO)[C@@]1(O)CCC2c1cn(Cc2ccc(F)cc2)nn1] | $2.7 \pm 1.4 \times 10^{-8}$ M |
| 66 | 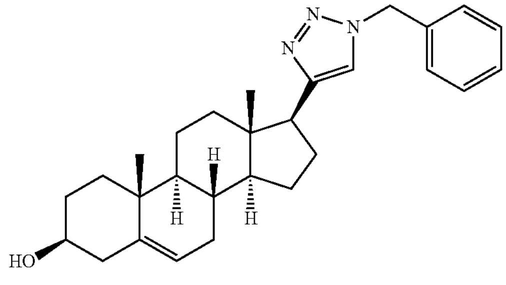 | $1.9 \pm 8.2 \times 10^{-12}$ M |

TABLE 1-continued
| Compound | Structure | Ki (M) |
|---|---|---|
| 67 | 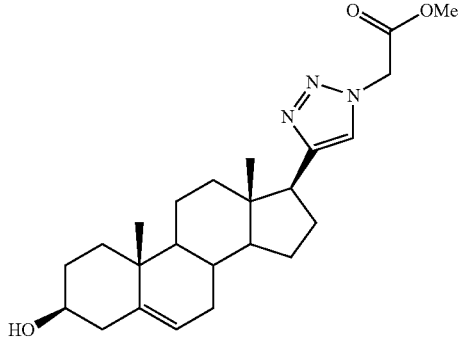 [SMILES: COC(=O)Cn1cc([C@H]2CCC3C4CC=C5C[C@@H](O)CC[C@]5(C)C4CC[C@@]32C)nn1] | *N.T |
| 68 | 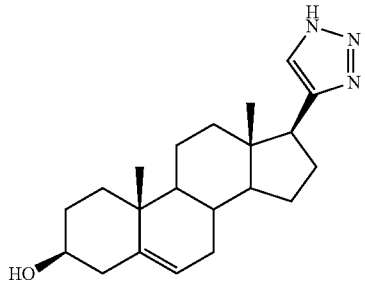 [SMILES: C[C@]12CC[C@H](O)CC1=CCC1C2CC[C@@]2(C)C1CC[C@@H]2c1c[nH]nn1] | *N.T |
| 48 | 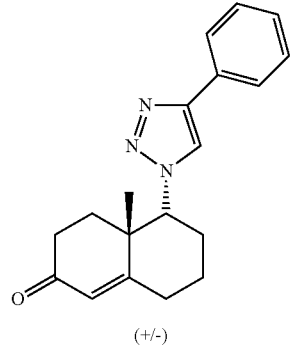 (+/-) | 2.7 ± 7.9 × 10⁻⁹ |
| 45 | 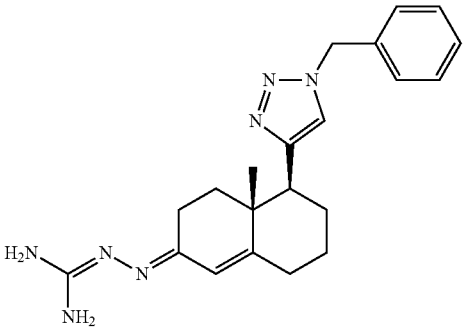 [SMILES: C[C@]12CC/C(=N\N=C(N)N)C=C1CCC[C@@H]2c1cn(Cc2ccccc2)nn1] | 5.6 ± 4.7 × 10⁻⁹ M |

TABLE 1-continued

| Compound | Structure | Ki (M) |
|---|---|---|
| 73 | 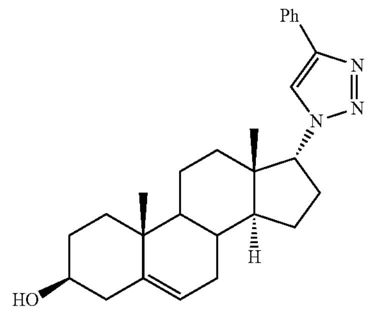 [SMILES: C[C@]12CCC3C(CC=C4C[C@@H](O)CC[C@@]43C)[C@@H]1CC[C@H]2n1cc(-c2ccccc2)nn1] | *N.T |
| 79 | 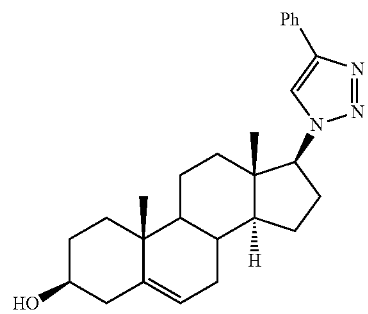 [SMILES: C[C@]12CCC3C(CC=C4C[C@@H](O)CC[C@@]43C)[C@@H]1CC[C@@H]2n1cc(-c2ccccc2)nn1] | *N.T |
| 75 | 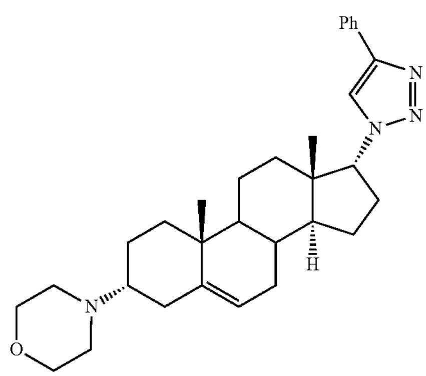 [SMILES: C[C@]12CCC3C(CC=C4C[C@H](N5CCOCC5)CC[C@@]43C)[C@@H]1CC[C@H]2n1cc(-c2ccccc2)nn1] | *N.T |
| 91 | 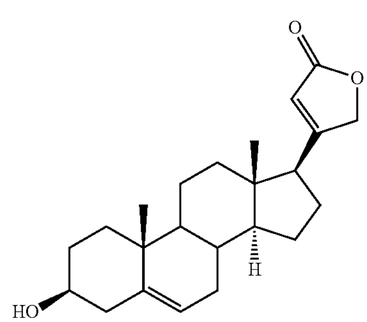 [SMILES: C[C@]12CCC3C(CC=C4C[C@@H](O)CC[C@@]43C)[C@@H]1CC[C@@H]2C1=CC(=O)OC1] | *N.T |

TABLE 1-continued

| Compound | Structure | Ki (M) |
|---|---|---|
| 82 | 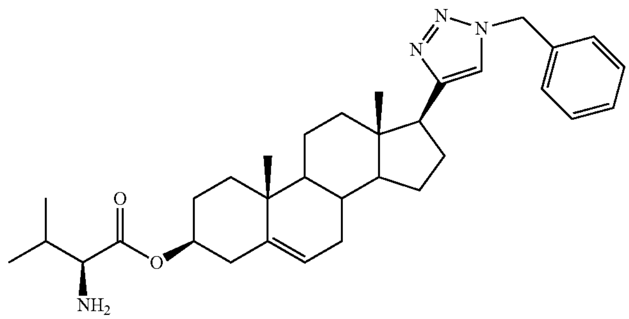 [SMILES: CC(C)[C@H](N)C(=O)O[C@H]1CC[C@@]2(C)C(=CCC3C2CC[C@@]2(C)C3CC[C@@H]2c2cn(Cc3ccccc3)nn2)C1] | *N.T |
| 85 | 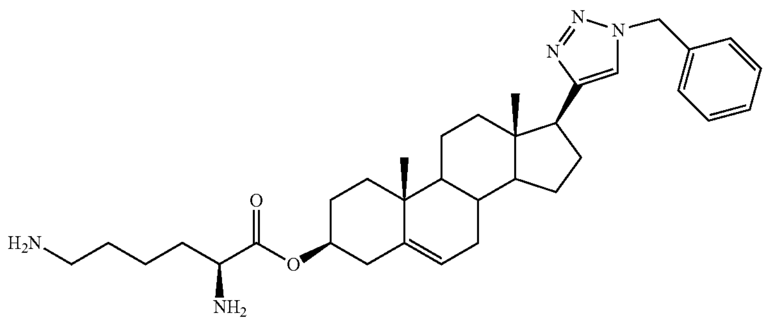 [SMILES: C[C@]12CC[C@H](OC(=O)[C@@H](N)CCCCN)CC1=CCC1C2CC[C@@]2(C)C1CC[C@@H]2c1cn(Cc2ccccc2)nn1] | *N.T |

*N.T: Not tested because of solubility issues.

The ability of a compound of the invention to inhibit sperm motility may be determined using pharmacological models which are well known to the art, or using Test B described below.

Test B. Sperm Motility Assays

Figure 1A:
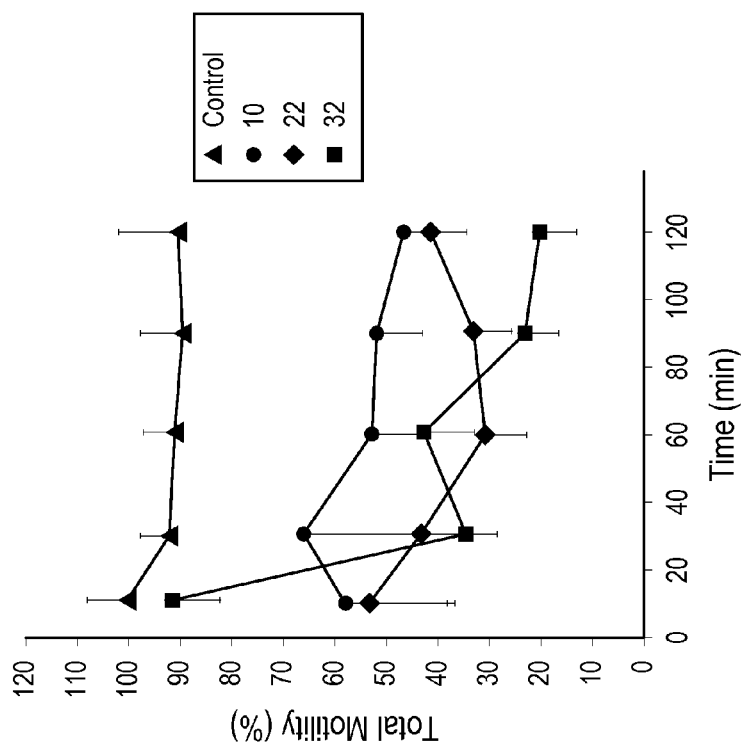

The effect of compounds from this invention is also tested on the motility of rat sperm. For this, rta spermatozoa were obtained from the caudal portion of the rat epididymus and resuspended in 300 µl of modified Tyrode's medium, containing: 100 mM NaCl, 4.7 mM KCl, 1.2 mM $KH_2PO_4$, 1.2 mM $MgSO_4$, 5.5 mM glucose, 0.8 mM pyruvic acid, 4.8 mM lactic acid and 20 mM Hepes (pH 7.4) and supplemented with 1.7 mM $CaCl_2$, which is required for sperm motility. Cells are incubated at 37° C. for different times with the compounds and are labeled with 2 µl of a 75 µM stock of the fluorescent nucleic acid stain SITO 21, which helps tracking cell movement. After 2 min incubation with the dye, 7 µl aliquots from each sample are taken and placed into a 20 µm depth glass cell chamber (Leja Products B.V., The Netherlands). Chambers are viewed on an Olympus BX51 microscope through a 20× phase objective and maintained at 37° C. on a heated platform. Viewing areas on each chamber are captured using a CCD camera. Sample movement is analyzed by computer assisted sperm analysis (CASA), using the Minitube SpermVision Digital Semen Evaluation system (version 3.5, Penetrating Innovations, Verona, Wis.). Different sperm motility parameters are analyzed, including total motility, progressive motility, curvilinear, average path and straight line velocities, and amplitude of lateral head displacement. The analytical setup parameters consider a cell identification or cell size area between 5 and 900 µm², a cutoff velocity corresponding to a minimum average orientation change of the head of 6 degrees, and a progressive motility threshold corresponding to a straight line distance of more than 5 µm. Linearity is calculated from the ratio between Straight Line Velocity and Curvilinear Velocity during the measurement period. Amplitude of Lateral Head Displacement is obtained as the maximum distance of the sperm head from the average trajectory of the sperm during the analysis period. An average of 80 cells/field are captured, at a rate of 30 frames per field, and a total of 10 fields in each sample are analyzed. Each field is taken randomly, scanning the slide following a pre-established path to ensure consistency in the method. Results for the effect of representative compounds of the invention on motility of rat sperm are shown in FIG. 1.

All chemicals, reagents and solvents were purchased from commercial sources and used directly without further purification. Reaction progress was monitored thin layer chromatography using silica gel plates (silica gel 60 $F_{254}$) and eluted TLC plates were visualized with UV light (254 nm) or developing the plate with phosphomolybdic acid/Ce $(SO_4)_2$ stains. The products were isolated and purified by flash chromatography. NMR experiments were performed on a 400/100 MHz instrument. NMR spectra were processed with the MestReNova program. Chemical shifts were reported as ppm relative to $CDCl_3$ (7.26 ppm for $^1H$, 77.0 ppm for $^{13}C$), DMSO-$d_6$ (2-50 ppm for $^1H$, 39.5 ppm for $^{13}C$) and $CD_3OD$ (4.87 ppm for $^1H$, 49.1 ppm for $^{13}C$). $^1H$ NMR coupling constants (J) are expressed in Hz, and multiplicity is described as follows: s=singlet; d=doublet; t=triplet; q=quartet; br=broad; m=multiplet; dd=doublet of doublets; dt=doublet of triplets; td=triplet of doublets; ddd=doublet of doublet of doublets. Specific rotations were obtained using a polarimeter at 23.0° C. High-resolution mass spectra and electrospray (ESI) experiments were recorded with electron-spray ionization. Melting points were determined with Electrothermal Digital Mel-Temp 3.0 melting point apparatus and are uncorrected.

The invention will now be illustrated by the following non-limiting Examples.

Example 1

4-((3R,3aR,5R,5bR,9aR,11S,12aS,14bS)-5,12a,14b-trihydroxy-11-(((3aR,4R,6S,7S,7aR)-7-hydroxy-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxin-3-yl)furan-2(5H)-one (1)

Synthesis of formula I compounds of the present invention started from commercially available ouabain. Compound 1 was prepared from ouabain according to the reported procedure from Hong et al., *Tetrahedron Lett.* 2006, 47, 2711-2715.

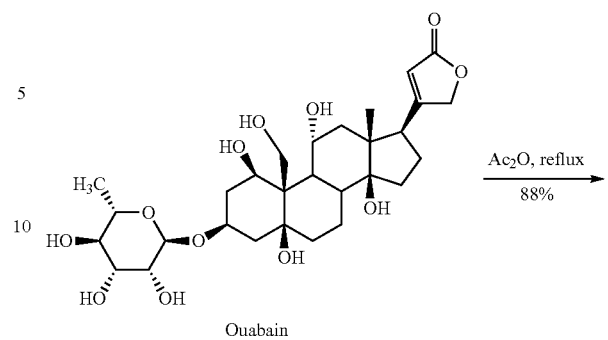

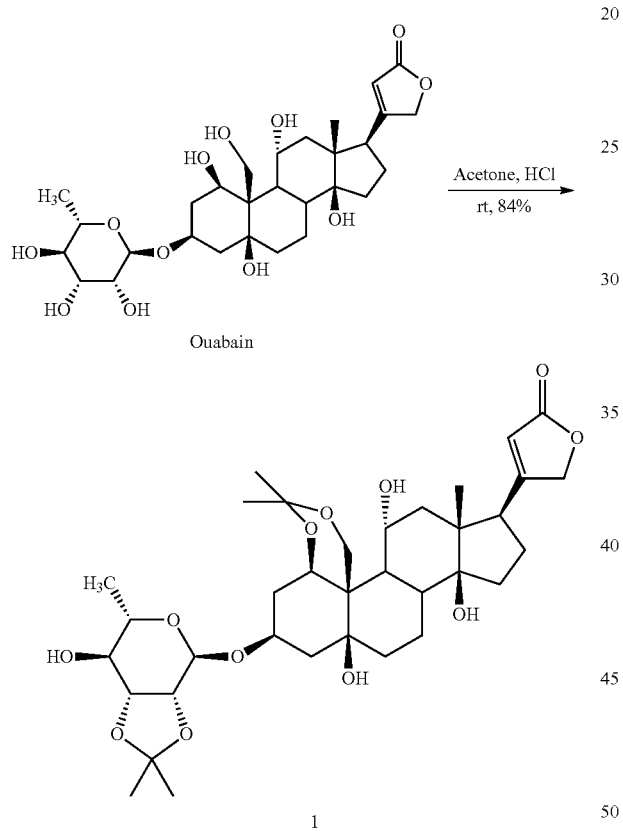

Example 1a (2R,3R,4R,5S,6S)-2-(((1R,3S,5S,10R,11R,13R,14S,17R)-1,11-diacetoxy-10-(acetoxymethyl)-5,14-dihydroxy-13-methyl-17-(5-oxo-2,5-dihydrofuran-3-yl)hexadecahydro-1H-cyclopenta[a]phenanthren-3-yl)oxy)-6-methyltetrahydro-2H-pyran-3,4,5-triyl triacetate (1a)

Compound 1 was prepared from ouabain according to the reported procedure from Hatakeyama et al., *J. Am. Chem. Soc.*, 2006, 128, 2518-2519.

Example 2

4-((3R,3aR,5R,5bR,9aR,11S,12aS,14bS)-12a,14b-dihydroxy-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxin-3-yl)furan-2(5H)-one (2)

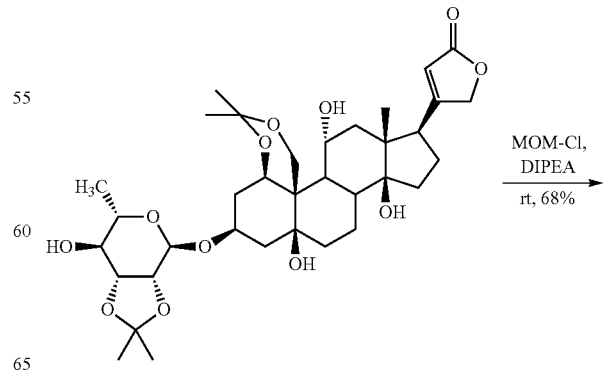

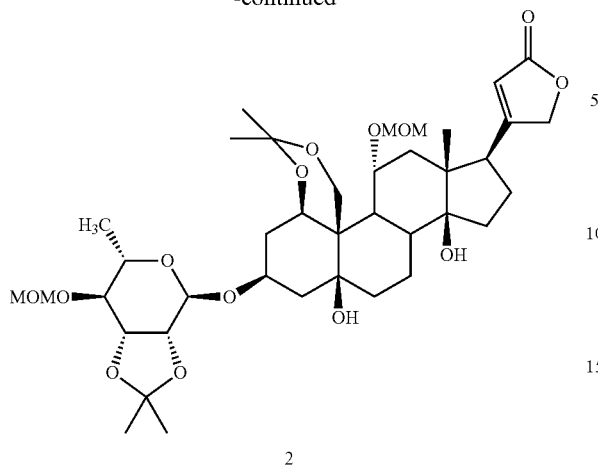

2

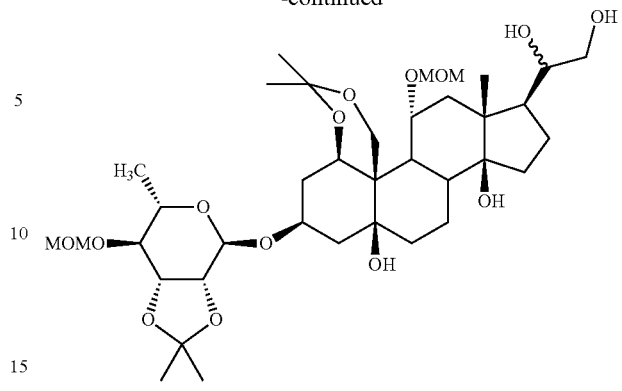

3

To a solution of diacetonide 1 (2.70 g, 4.06 mmol) and diisopropylethylamine (5.67 mL, 32.53 mmol) in (CH$_2$Cl$_2$ 75 mL) was added chloromethyl methyl ether (MOM-Cl) (1.22 mL, 16.25 mmol) at 0° C. The reaction mixture was stirred at room temperature for 12 h, diluted with water (75 mL), organic phase was separated and extracted with an additional CH$_2$Cl$_2$ (3×50 mL). The extracts were washed with saturated aqueous NH$_4$Cl (50 mL) solution and brine (50 mL), dried over Na$_2$SO$_4$. Volatiles were removed under reduced pressure, and the crude product was purified by column chromatography (silica gel, hexanes/ethyl acetate, 3:7) to give 2 (2.07 g, 68%) as a yellow foam: $^1$H NMR (400 MHz, CDCl$_3$) δ 5.89 (s, 1H), 5.11 (s, 1H), 4.96 (d, J=6.4 Hz, 1H), 4.91-4.76 (m, 2H), 4.72 (q, J=6.5 Hz, 3H), 4.66 (d, J=6.4 Hz, 1H), 4.58 (s, 1H), 4.46 (d, J=12.3 Hz, 1H), 4.13 (dd, J=13.6, 8.0 Hz, 2H), 4.07 (d, J=5.5 Hz, 1H), 4.04-3.90 (m, 2H), 3.62 (t, J=15.5 Hz, 1H), 3.40 (dd, J=15.5, 8.7 Hz, 7H), 3.00 (t, J=7.6 Hz, 1H), 2.17-1.94 (m, 5H), 1.93-1.76 (m, 4H), 1.72-1.45 (m, 7H), 1.42-1.27 (m, 10H), 1.27-1.19 (m, 5H), 1.11 (m, 1H), 0.88 (s, 3H); $^{13}$C NMR (100 MHz, CDCl$_3$) δ 174.0, 172.4, 117.7, 109.1, 100.9, 97.0, 96.8, 96.3, 83.6, 78.3, 78.1, 76.5, 75.8, 73.3, 73.0, 72.9, 66.6, 64.7, 60.5, 56.1, 55.8, 49.5, 48.3, 47.5, 45.3, 44.1, 40.8, 35.8, 34.5, 33.9, 30.4, 27.9, 26.6, 26.5, 24.8, 23.0, 22.7, 17.7, 17.5; HRMS (ESI) calcd for C$_{39}$H$_{61}$O$_{14}$ (M+H)$^+$ 753.4061. found 753.4054.

Example 3

(3S,3aR,5R,5bR,9aR,11S,12aS,14bS)-3-(1,2-dihydroxyethyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (3)

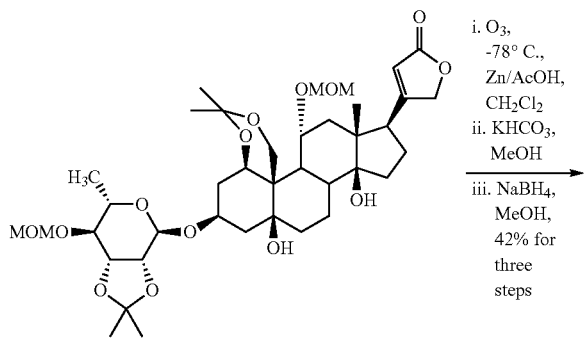

i. O$_3$, -78° C., Zn/AcOH, CH$_2$Cl$_2$
ii. KHCO$_3$, MeOH
iii. NaBH$_4$, MeOH, 42% for three steps

2

Ozone was bubbled through a solution of 2 (2.50 g, 3.32 mmol) in CH$_2$Cl$_2$ (60 mL) at −78° C. for 1 h and then stirred at −78° C. for 2 h. The solution was degassed with nitrogen and then Zn (11.88 g, 182 mmol) and AcOH (12.35 mL, 216 mmol) were added and stirred for an additional 2 h at room temperature. Filtered and then the volatiles were removed in vacuo to get the hydroxymethyl ester (2.20 g), which was used for the next step without further purification.

To a solution of the above residue (2.20 g) in methanol (30 mL) was added KHCO$_3$ (0.83 g, 8.38 mmol) in 5 mL of H$_2$O. After being stirred for 3 h at room temperature, the reaction solution was diluted with water (50 mL) and then extracted with ethyl acetate (3×50 mL). The combined organic layers were dried over Na$_2$SO$_4$, filtered and the solvent removed in vacuo to give the unstable hydroxyl ketone (1.25 g), which was immediately subjected to the next step.

The above crude hydroxy ketone (1.25 g) was dissolved in methanol (30 mL) and cooled to 0° C. Sodium borohydride (0.46 g, 12.36 mmol) was added and stirred for 30 min. To the reaction was added saturated aqueous NH$_4$Cl (30 mL) and extracted with ethyl acetate (3×30 mL). The organic layers were combined, dried over Na$_2$SO$_4$, filtered and the solvent was removed in vacuo. The resultant residue was purified by chromatography (silica gel, hexanes/ethyl acetate, 1:9) to afford the diastereomeric mixture of diol 3 (1.01 g, 42% for three steps) as a white solid: mp 119-121° C. $^1$H NMR (400 MHz, CDCl$_3$) δ 5.11 (s, 1H), 4.96 (d, J=6.4 Hz, 1H), 4.91 (s, 1H), 4.82 (d, J=6.5 Hz, 1H), 4.76 (d, J=6.1 Hz, 1H), 4.70-4.63 (m, 2H), 4.52-4.40 (m, 2H), 4.19-4.02 (m, 3H), 4.01-3.59 (m, 5H), 3.47-3.44 (m, 1H), 3.43-3.34 (m, 6H), 2.24-1.17 (m, 32H), 1.09 (d, J=3.8 Hz, 4H); HRMS (ESI) calcd for C$_{37}$H$_{63}$O$_{14}$ (M+H)$^+$ 731.4218. found 731.4238.

Example 4

(3S,3aR,5R,5bR,9aR,11S,12aS,14bS)-12a,14b-dihydroxy-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-3-carbaldehyde (4)

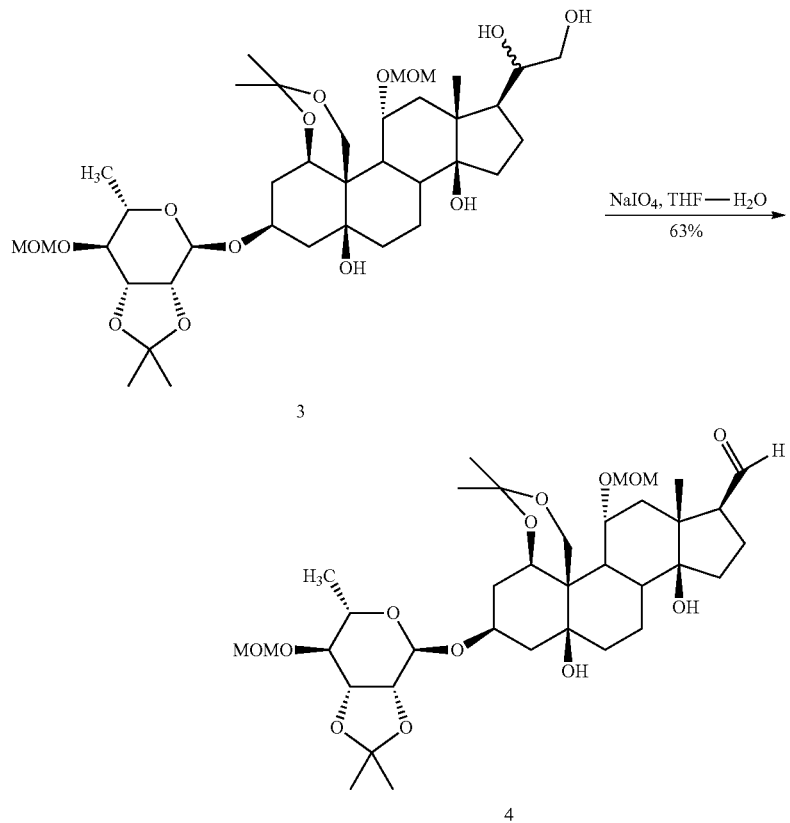

To a stirred solution of diol 3 (2.50 g, 3.42 mmol) in THF:H$_2$O (8:2, 20 mL) was added sodium periodate (2.18 g, 10.27 mmol). After being stirred for 1 h, the reaction was diluted with EtOAc (50 mL). Insoluble materials were filtered off and the filtrate was washed with water, brine, dried over Na$_2$SO$_4$ the solvent was then removed in vacuo. The residue was purified by column chromatography (silica gel, hexanes/ethyl acetate, 3:7) to afford and desired aldehyde 4 (1.50 g, 63%) as foam: $^1$H NMR (400 MHz, CDCl$_3$) δ 9.72 (s, 1H), 5.12 (s, 1H), 4.98 (d, J=6.4 Hz, 1H), 4.91-4.79 (m, 2H), 4.71-4.63 (m, 3H), 4.46 (d, J=12.3 Hz, 1H), 4.20-4.10 (m, 2H), 4.08 (d, J=5.5 Hz, 1H), 4.02-3.83 (m, 2H), 3.72 (d, J=12.3 Hz, 1H), 3.49-3.30 (m, 7H), 2.46 (dt, J=9.0, 3.2 Hz, 1H), 2.28-1.76 (m, 9H), 1.74-1.22 (m, 23H), 1.11 (s, 3H); $^{13}$C NMR (100 MHz, CDCl$_3$) δ 205.8, 109.1, 100.9, 97.5, 96.7, 96.3, 83.1, 78.3, 78.2, 76.5, 75.8, 73.1, 72.9, 66.8, 64.6, 61.1, 60.5, 56.0, 55.8, 49.9, 47.8, 45.6, 44.9, 40.0, 36.2, 34.8, 33.2, 30.2, 27.9, 26.5, 24.8, 23.10, 23.06, 20.0, 17.5, 15.9; HRMS (ESI) calcd for C$_{36}$H$_{59}$O$_{13}$ (M+H)$^+$ 699.3956. found 699.3977.

Example 5

(3S,3aR,5R,5bR,9aR,11S,12aS,14bS)-3-(1-hydroxyprop-2-yn-1-yl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (5)

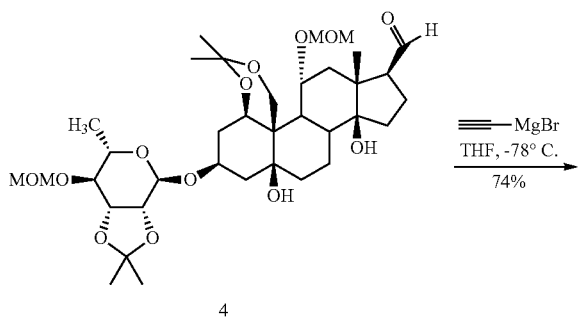

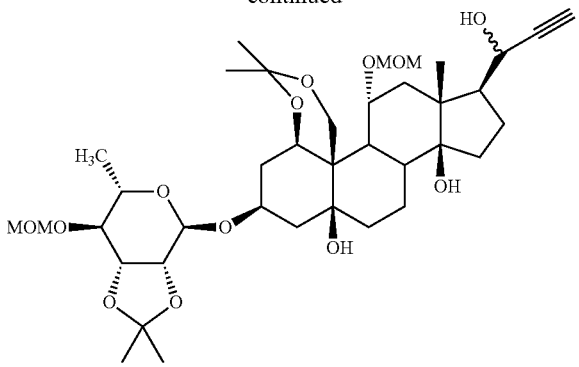

5

To a solution of aldehyde 4 (1.00 g, 1.43 mmol) in THF (30 mL) at −78° C. was added ethynylmagnesium bromide (0.5 M solution in THF, 14.65 mL, 7.15 mmol). After being stirred for 1 h, the reaction mixture was quenched with saturated aqueous NH$_4$Cl (30 mL). The organic phase was separated and the mixture was extracted with EtOAc (2×30 mL) and the organic layers were dried over Na$_2$SO$_4$ and concentrated in vacuo. The residue was purified by flash column chromatography (silica gel, hexanes/ethyl acetate, 6:4) to yield alkynol 5 (0.76 g, 74%) as white foam: $^1$H NMR (400 MHz, CDCl$_3$) δ 5.10 (s, 1H), 5.07 (d, J=23.1 Hz, 1H), 4.96 (d, J=6.4 Hz, 1H), 4.91 (s, 1H), 4.83 (d, J=6.5 Hz, 1H), 4.66 (dd, J=6.3, 3.5 Hz, 3H), 4.54 (s, 1H), 4.44 (d, J=12.3 Hz, 1H), 4.11 (dd, J=13.5, 6.3 Hz, 2H), 4.07 (d, J=5.5 Hz, 1H), 3.94 (dd, J=9.9, 6.2 Hz, 1H), 3.85-3.57 (m, 3H), 3.47-3.23 (m, 7H), 2.40 (d, J=2.0 Hz, 1H), 1.96-1.75 (m, 10H), 1.69-1.19 (m, 22H), 1.08 (d, J=11.8 Hz, 3H).

Example 6

(3S,3aR,5R,5bR,9aR,11S,12aS,14bS)-3-((1-(4-fluorobenzyl)-1H-1,2,3-triazol-4-yl)(hydroxy)methyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (6)

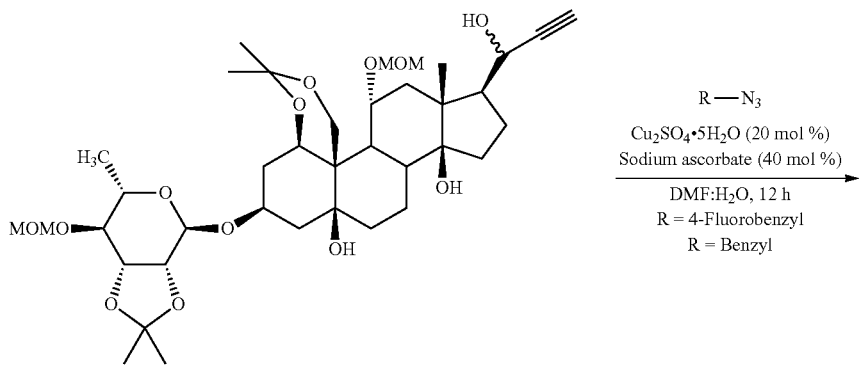

5

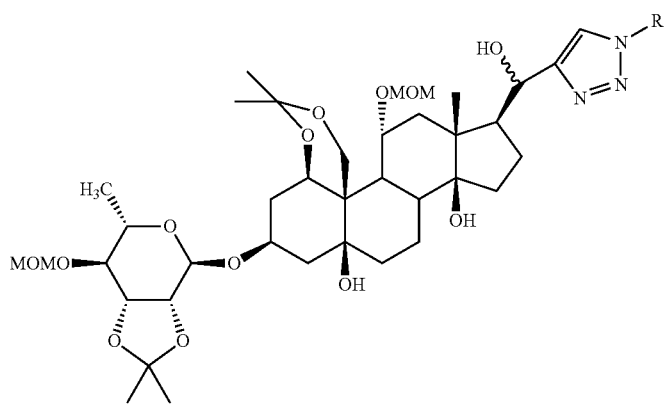

6 R = 4-Fluorobenzyl, Yield = 40%
7 R = Benzyl, Yield = 64%

To a solution of 4-fluorobenzyl azide (14 mg. 0.096 mmol) and alkynol 5 (70 mg, 0.096 mmol) in DMF (3 mL) was added sodium ascorbate (8 mg, 0.038 mmol) in 1 mL water and the reaction mixture was stirred for 2 minutes. To the resultant mixture, CuSO$_{4\cdot 5H_2}$O (5 mg, 0.019 mmol) in 1 mL water was added. The mixture was stirred at room temperature for 12 h, added water )4 mL), and extracted with EtOAc (3x5 mL). Evaporation of combined organic extracts afforded a green solid, which was purified by flash chromatography (silica gel, hexanes/ethyl acetate, 2:8) to give compound 6 (25 mg, 42%) as foam: $^1$H NMR (400 MHz, CDCl$_3$) δ 7.37 (s, 1H) 7.23 (dd, J=5.9, 2.7 Hz, 2H), 7.09-7.01 (m, 2H), 5.50-5.41 (m, 2H), 5.08 (d, J=9.6 Hz, 2H), 4.96 (d, J=6.5 Hz, 1H), 4.91 (s, 1H), 4.82 (d, J=6.5 Hz, 1H), 3.83 (td, J=10.9, 5.1 Hz, 1H), 3.78-3.66 (m, 1H), 3.44-3.35 (m, 4H), 3.34 (s, 3H), 2.37-2.26 (m, 1H), 2.14-1.66 (m, 8H), 1.67-1.42 (m, 9H), 1.41-1.15 (m, 18H), 1.08-0.99 (m, 1H); $^{13}$C NMR (100 MHz, CDCl$_3$) δ 161.6, 130.5, 129.9, 129.8, 120.8, 116.2, 116.0, 109.1, 100.8, 97.7, 96.7, 96.3, 83.3, 78.3, 78.2, 76.5, 73.1, 72.9, 66.9, 66.1, 64.3, 60.5, 56.0, 55.8, 54.8, 53.4, 47.8, 47.6, 46.7, 45.4, 40.2, 36.2, 34.9, 32.5, 30.2, 27.9, 26.5, 24.8, 23.1, 18.5, 18.4, 17.5, 15.6; HRMS (ESI) calcd for C$_{45}$H$_{67}$N$_3$O$_{13}$F (M+H)$^+$ 876.4658. found 876.4686.

Example 7

(3S,3aR,5R,5bR,9aR,11S,12aS,14bS)-3-((1-benzyl-1H-1,2,3-triazol-4-yl)(hydroxy)methyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (7)

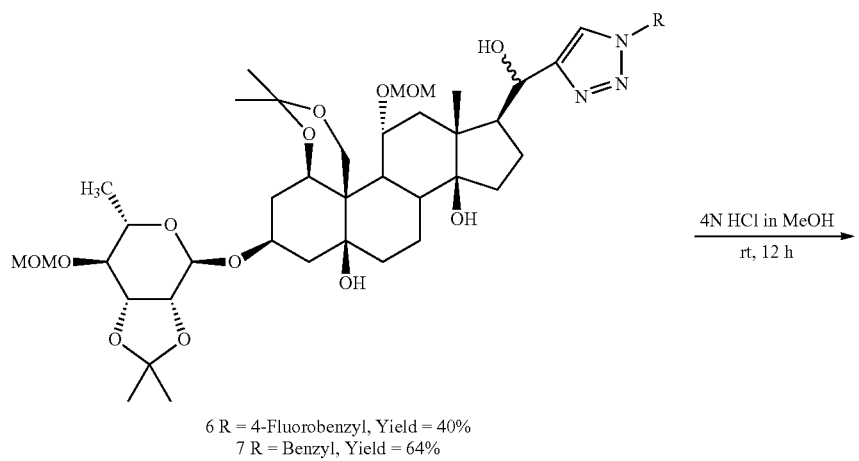

6 R = 4-Fluorobenzyl, Yield = 40%
7 R = Benzyl, Yield = 64%

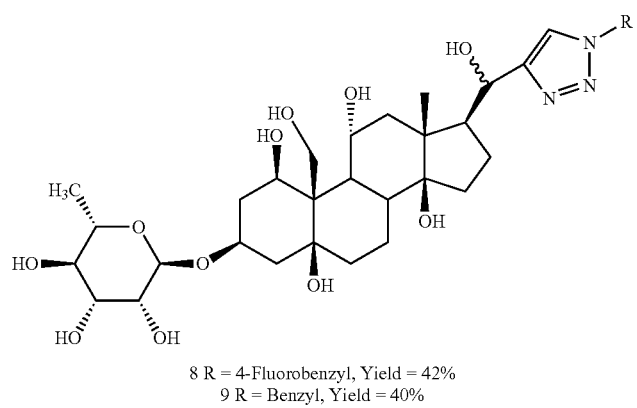

8 R = 4-Fluorobenzyl, Yield = 42%
9 R = Benzyl, Yield = 40%

Followed the procedure described for 6 to get the 7 (75 mg, 64%) as white foam.

Example 8

(1R,3S,5S,10R,11R,13R,14S,17S)-17-((1-(4-fluorobenzyl)-1H-1,2,3-triazol-4-yl)(hydroxy)methyl)-10-(hydroxymethyl)-13-methyl-3-(((2R,3R,4R,5R,6S)-3,4,5-trihydroxy-6-methyltetrahydro-2H-pyran-2-yl)oxy)hexadecahydro-1H-cyclopenta[a]phenanthrene-1,5,11,14-tetraol (8)

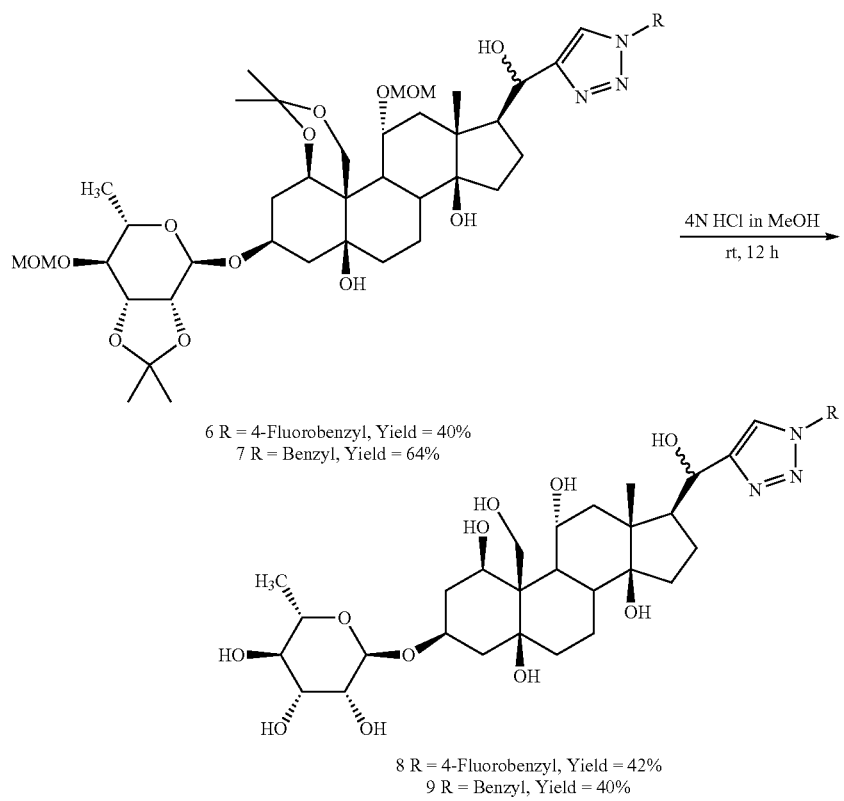

6 R = 4-Fluorobenzyl, Yield = 40%
7 R = Benzyl, Yield = 64%

8 R = 4-Fluorobenzyl, Yield = 42%
9 R = Benzyl, Yield = 40%

The compound 6 (35 mg, 0.04 mmol) was dissolved in 4N HCl in MeOH (5 ml) and the solution was stirred at room temperature for 12 h. After completion of the reaction (monitored by TLC), the solvent was removed in vacuo. The residue was purified by column chromatography (silica gel, EtOAc/MeOH, 8:2 with 2% H$_2$O) to give 8 (12 g, 42%) as foam: $^1$H NMR (400 MHz, CD$_3$OD) δ 7.95 (s, 1H), 7.39 (dd, J=8.6, 5.3 Hz, 2H), 7.22-6.97 (m, 2H), 5.61 (d, J=8.4 Hz, 2H), 5.01 (s, 1H), 4.25 (m, 4H), 3.83-3.61 (m, 3H), 3.45-3.27 (m, 3H), 2.30-1.88 (m, 7H), 1.87-1.16 (m, 17H).

Example 9

(1R,3S,5S,10R,11R,13R,14S,17S)-17-((1-benzyl-1H-1,2,3-triazol-4-yl)(hydroxy)methyl)-10-(hydroxymethyl)-13-methyl-3-(((2R,3R,4R,5R,6S)-3,4,5-trihydroxy-6-methyltetrahydro-2H-pyran-2-yl)oxy)hexadecahydro-1H-cyclopenta[a]phenanthrene-1,5,11,14-tetraol (9)

Followed the procedure described for 8 to get the 9 (16 mg, 40%) as white foam: $^1$H NMR (400 MHz, CDCl$_3$) δ 8.06 (s, 1H), 7.38 (t, J=9.5 Hz, 5H), 5.66 (d, J=10.3 Hz, 2H), 5.03 (s, 1H), 4.25 (m, 4H), 3.84-3.62 (m, 3H), 3.41-3.33 (m, 3H), 2.28-1.86 (m, 7H), 1.85-1.17 (m, 17H).

Example 10

(3S,3aR,5R,5bR,9aR,11S,12aS,14bS)-3-(hydroxymethyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (10)

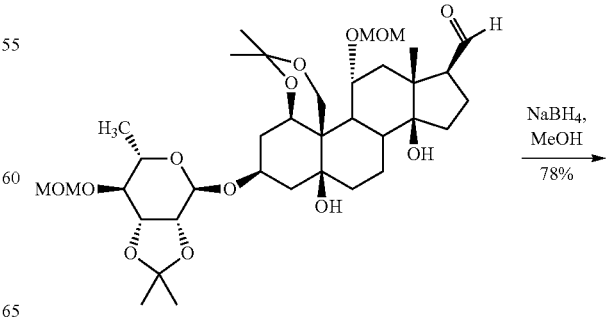

4

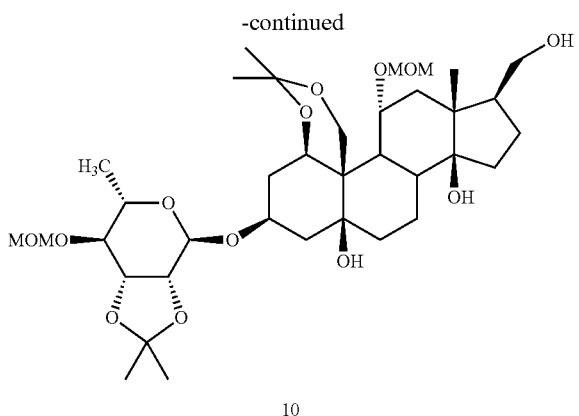

10

The aldehyde 4 (0.50 g, 0.71 mmol) was dissolved in methanol (10 mL) and cooled to 0° C. Sodium borohydride (0.08 g, 2.14 mmol) was added and stirred for 30 min. The reaction was quenched with saturated aqueous NH$_4$Cl (15 mL) solution and extracted with ethyl acetate (3×15 mL). The organic layers were combined, dried over Na$_2$SO$_4$, filtered and the solvent was removed in vacuo. The resultant residue was purified by column chromatography (silica gel, hexanes/ethyl acetate, 2:8) to afford the corresponding alcohol 10 (0.39 g, 78%) as white a solid: mp 126-129° C.; $[\alpha]_D^{26}$ −4.12 (c=1.55, CHCl$_3$); $^1$H NMR (400 MHz, CDCl$_3$) δ 5.11 (s, 1H), 4.96 (d, J=6.4 Hz, 1H), 4.92 (t, J=3.2 Hz, 1H), 4.82 (d, J=6.5 Hz, 1H), 4.69-4.62 (m, 3H), 4.44 (d, J=12.3 Hz, 1H), 4.17-4.08 (m, 2H), 4.07 (d, J=5.5 Hz, 1H), 3.95 (dq, J=12.5, 6.2 Hz, 1H), 3.89-3.70 (m, 3H), 3.51 (dd, J=10.8, 2.9 Hz, 1H), 3.44-3.36 (m, 4H), 3.35 (s, 3H), 2.11-1.88 (m, 7H), 1.87-1.73 (m, 3H), 1.65-1.20 (m, 23H), 1.16-0.98 (m, 4H); $^{13}$C NMR (100 MHz, CDCl$_3$) δ 109.1, 100.8, 97.5, 96.76, 96.3, 82.1, 78.3, 78.2, 76.5, 73.2, 73.0, 66.9, 64.6, 62.2, 60.6, 55.9, 55.8, 50.7, 47.8, 47.2, 46.7, 45.3, 40.1, 36.3, 34.9, 32.8, 30.3, 27.9, 26.5, 24.9, 23.1, 21.6, 17.5, 15.5; HRMS (ESI) calcd for C$_{36}$H$_{61}$O$_{13}$ (M+H)$^+$ 701.4112. found 701.4091.

Example 11

(3S,3aR,5R,5bR,9aR,11S,12aS,14bS)-12a,14b-dihydroxy-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-3-carbonitrile (11)

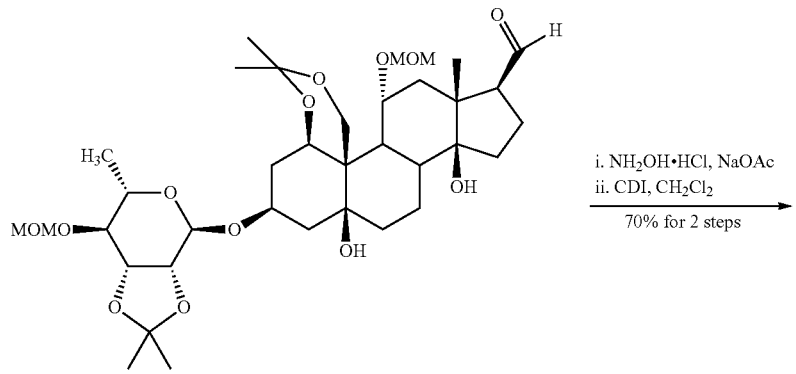

4

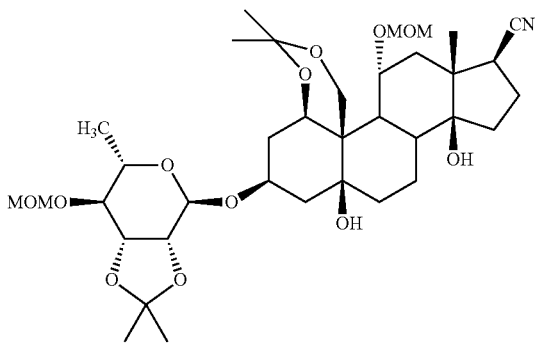

11

To a solution of aldehyde 4 (0.25 g, 0.35 mmol) in EtOH (10 mL) at room temperature were added NH$_2$OH.HCl (0.09 g, 1.43 mmol), NaOAc (0.13 g, 1.60 mmol). After being stirred for 1 h, the reaction mixture was diluted with water (10 mL) and extracted with EtOAc (3×10 mL). The combined organic layers were dried over Na$_2$SO$_4$ and concentrated in vacuo to give oxime (0.24 g) as colorless foam.

To a stirred solution of oxime (0.24 g, 0.33 mmol) in CH$_2$Cl$_2$ (20 mL) and 1,1'-carbonyldiimidazole (0.19 g, 1.17 mmol) was added at room temperature. After being stirred for 12 h, saturated aqueous NH$_4$Cl (10 mL) was added to the reaction mixture, and the mixture was extracted with CH$_2$Cl$_2$ (3×15 mL). The combined organic layers were dried over Na$_2$SO$_4$ and concentrated to a residue, that was purified by flash chromatography (silica gel, hexanes/ethyl acetate, 7:3) to furnish nitrile 11 (0.17 g, 70%) as a white solid: mp 97-99° C.; $^1$H NMR (400 MHz, CDCl$_3$) δ 5.07 (s, 1H), 4.96 (d, J=6.3 Hz, 1H), 4.81-4.55 (m, 5H), 4.46 (d, J=12.2 Hz, 1H), 4.19-4.02 (m, 4H), 3.95 (dd, J=14.0, 7.5 Hz, 2H), 3.65 (d, J=12.3 Hz, 1H), 3.47-3.26 (m, 7H), 2.84 (t, J=7.1 Hz, 1H), 2.24-1.65 (m, 10H), 1.50-1.43 (m, 4H), 1.42-1.17 (m, 16H), 1.12-0.91 (m, 4H); $^{13}$C NMR (100 MHz, CDCl$_3$) δ 121.7, 109.1, 100.9, 97.1, 96.8, 96.3, 83.1, 78.3, 78.1, 76.5, 75.6, 72.9, 66.6, 64.6, 60.5, 56.1, 55.8, 47.54, 47.45, 45.3, 41.8, 40.4, 39.4, 35.8, 34.7, 33.2, 30.3, 27.9, 26.4, 25.6, 24.8, 23.0, 22.6, 19.1, 18.0, 17.5; HRMS (ESI) calcd for C$_{36}$H$_{58}$O$_{12}$(M+H)$^+$ 696.3959. found 696.3949.

Example 12

4-((3R,3aR,5R,5bR,9aR,11S,12aS,14bS)-5,11,12a,14b-tetrahydroxy-3a,8,8-trimethylhexadecahydro-1H-cyclopenta[7,8]phenanthro[4,4a-d][1,3]dioxin-3-yl)furan-2(5H)-one (12)

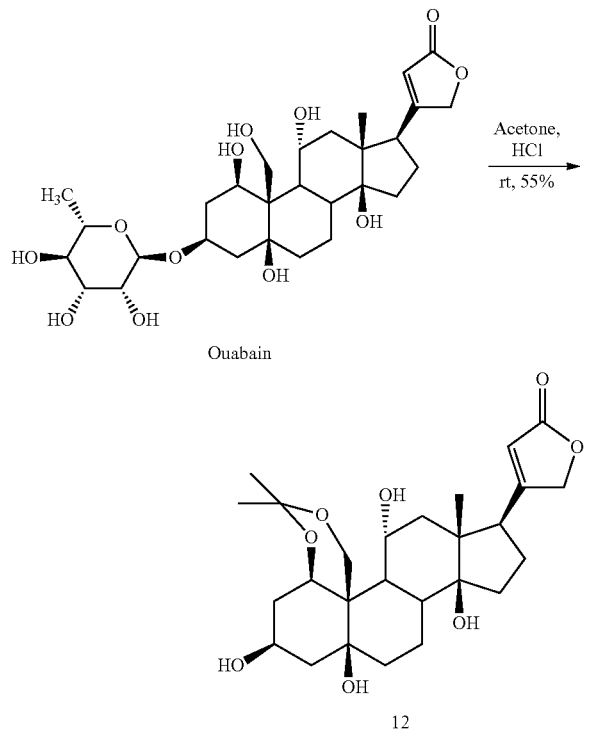

Compound 12 was readily prepared from ouabain using the literature procedure from Sneeden et al., *J. Am. Chem. Soc.*, 1953, 75, 3510-3513.

Example 13

4-((3R,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxin-3-yl)furan-2(5H)-one (13)

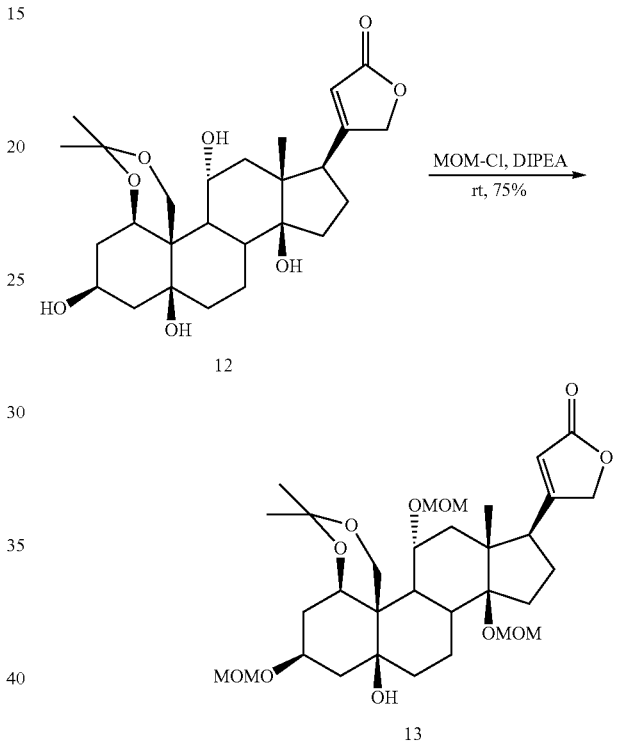

To a suspension of ouabagenine monoacetonide 12 (0.99 g, 2.07 mmol) in dichloromethane (30 mL) was added diisopropylethylamine (3.61 mL, 20.71 mmol) at room temperature. After stirring for 5 min the reaction mixture was cooled to 0° C. and chloromethyl methyl ether (MOM-Cl) (0.93 mL, 12.42 mmol) was added. The mixture was warmed to room temperature and stirred for 72 h, the reaction mixture was diluted with water (30 mL), the organic phase was separated and aqueous phase extracted with an additional CH$_2$Cl$_2$ (2×30 mL). The combined organic layers were dried over Na$_2$SO$_4$ and concentrated in vacuo. The residue was purified by flash column chromatography (silica gel, hexanes/ethyl acetate 1:9) to give 13 (0.98 g, 75%) as yellow foam: $^1$H NMR (400 MHz, CDCl$_3$) δ 5.86 (d, J=1.2 Hz, 1H), 4.92-4.47 (m, 10H), 4.35 (d, J=12.9 Hz, 2H), 4.12 (s, 1H), 3.58 (d, J=12.2 Hz, 1H), 3.49-3.28 (m, 10H), 2.20-1.23 (m, 21H), 1.21-1.05 (m, 1H), 0.75 (s, 3H); $^{13}$C NMR (100 MHz, CDCl$_3$) δ 173.9, 170.9, 116.8, 101.2, 95.8, 94.7, 92.7, 90.6, 74.7, 73.5, 72.5, 70.8, 66.4, 60.8, 56.3, 56.1, 55.6, 48.3, 47.3, 46.6, 43.7, 40.6, 38.6, 34.9, 34.5, 30.2, 29.6, 27.9, 25.2, 23.1, 21.9, 20.9; HRMS (ESI) calcd for C$_{32}$H$_{50}$O$_{11}$Na (M+Na)$^+$ 633.3251. found 633.3261.

Example 14

2-hydroxy-1-((3S,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxin-3-yl)ethanone (14)

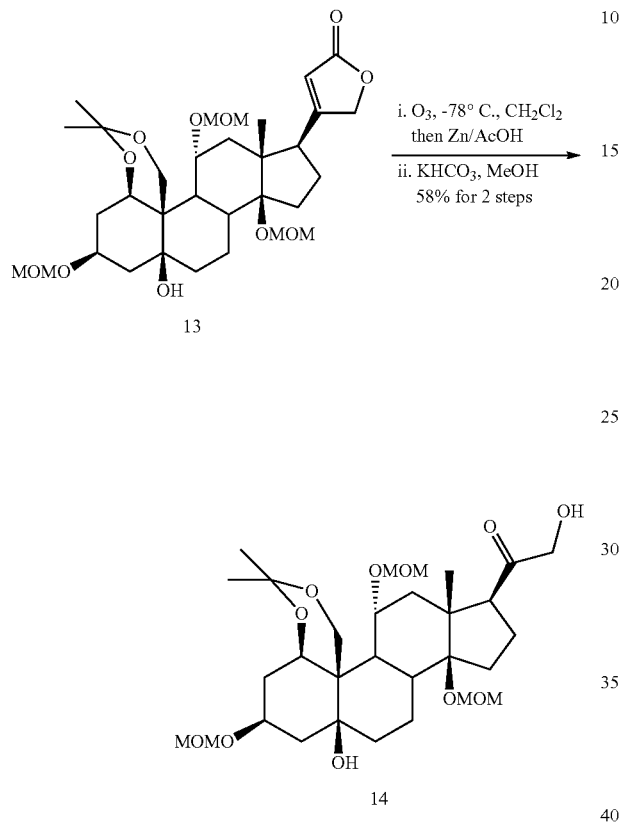

Example 15

1-((3S,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxin-3-yl)ethane-1,2-diol (15)

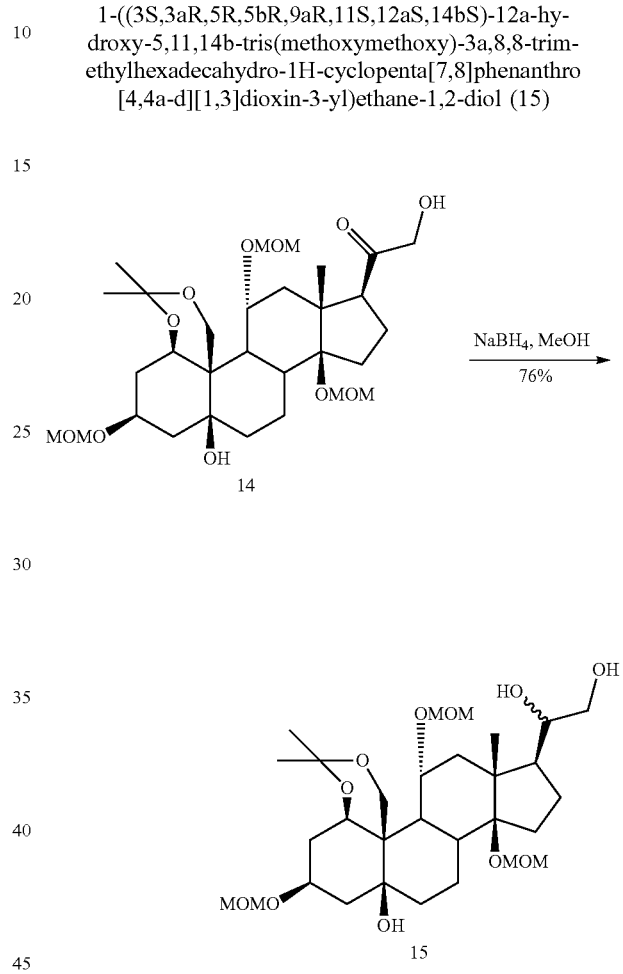

Ozone was bubbled through a solution of 13 (1.00 g, 1.58 mmol) in $CH_2Cl_2$ (20 mL) at −78° C. for 1 h. Once the deep blue color persisted the reaction was allowed to stir at −78° C. for 2 h. Excess ozone was removed by bubbling $N_2$ through the solution until the solution became colorless. Zn (5.6 g, 87.02 mmol) and AcOH (5.88 mL, 102.84 mmol) were added to the above solution and stirred for 2 h at room temperature. The suspension was filtered through a pad of Celite and the pad was washed with $CH_2Cl_2$ (60 mL). The filtrate was washed with water (30 mL) and brine (30 mL), dried over $Na_2SO_4$ and concentrated in vacuo to afford crude hydroxymethyl ester (1.03 g), which was used for the next step without further purification.

To a solution of above crude hydroxymethyl ester compound (1.03 g, 1.55 mmol) in methanol (20 mL) was added $KHCO_3$ (0.46 g, 4.65 mmol) in 1.0 mL of water. After being stirred at room temperature for 3 h, then MeOH was removed under reduced pressure. The residue was taken up in EtOAc (50 mL) and washed with water (30 mL). The organic layer was dried over $Na_2SO_4$ and concentrated in vacuo. The resultant residue was purified by silica gel chromatography (hexanes/ethyl acetate, 3:7) to afford the somewhat unstable hydroxy ketone 14 (0.61 g, 58%, for two steps) as foam: $^1H$ NMR (400 MHz, $CDCl_3$) δ 4.86 (dd, J=11.6, 5.1 Hz, 1H), 4.78-4.54 (m, 6H), 4.50 (dd, J=17.3, 9.1 Hz, 1H), 4.44 (d, J=2.7 Hz, 2H), 4.20 (dd, J=7.1, 4.7 Hz, 2H), 4.12 (td, J=11.1, 5.8 Hz, 1H), 3.56 (dd, J=17.0, 11.2 Hz, 1H), 3.47-3.30 (m, 10H), 3.27 (t, J=4.7 Hz, 1H), 2.22-2.00 (m, 4H), 1.99-1.64 (m, 6H), 1.58-1.19 (m, 11H), 1.18-1.01 (m, 1H), 0.77 (s, 3H).

To a solution of hydroxy ketone 14 (1.00 g, 1.70 mmol) in methanol (20 mL) was added sodium borohydride (0.19 g, 5.11 mmol) at 0° C. After stirred for 30 min, the reaction was quenched with saturated aqueous $NH_4Cl$ (20 mL). The resultant mixture was extracted with ethyl acetate (3×30 mL). The combined organic layers were dried over $Na_2SO_4$ and concentrated in vacuo. The residue was purified by silica gel chromatography (hexanes/ethyl acetate 1:9) to afford the diastereomeric mixture of diol 15 (0.72 g, 76%) as white foam: $^1H$ NMR (400 MHz, $CDCl_3$) δ 4.90-4.53 (m, 8H), 4.48 (d, J=12.2 Hz, 1H), 4.09 (s, 1H), 4.02-3.60 (m, 4H), 3.59-3.21 (m, 11H), 2.31-1.18 (m, 23H), 1.19-0.97 (s, 3H); $^{13}C$ NMR (100 MHz, $CDCl_3$) δ 100.9, 97.1, 94.6, 91.8, 91.4, 75.6, 72.8, 70.8, 69.6, 66.9, 66.3, 60.8, 56.2, 56.0, 55.5, 50.9, 48.7, 48.1, 46.4, 46.1, 38.1, 36.4, 35.1, 30.4, 29.3, 25.0, 23.7, 23.1, 19.3, 17.6; HRMS (ESI) calcd for $C_{30}H_{53}O_{11}$ $(M+H)^+$ 589.3588. found 589.3569.

Example 16

(3S,3aR,5R,5bR,9aR,11S,12aS,14bS)-12a-hydroxy-5,11,14b-tris(methoxymethoxy)-3a,8,8-trimethyl-hexadecahydro-1H-cyclopenta[7,8]phenanthro[4,4a-d][1,3]dioxine-3-carbaldehyde (16)

Example 17

(3S,3aR,5R,5bR,9aR,11S,12aS,14bS)-3-(1-hydroxy-prop-2-yn-1-yl)-5,11,12a-tris(methoxymethoxy)-3a,8,8-trimethylhexadecahydro-1H-cyclopenta[7,8]phenanthro[4,4a-d][1,3]dioxin-14b-ol (17)

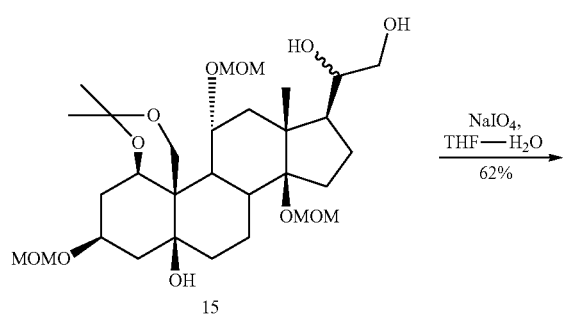

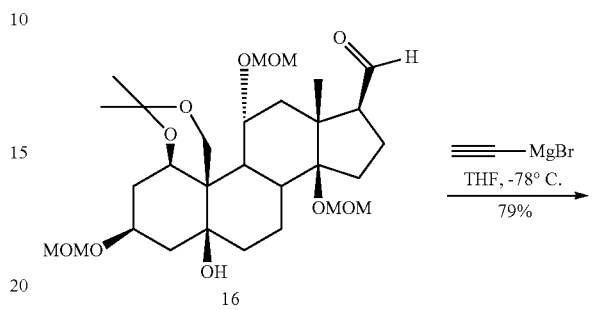

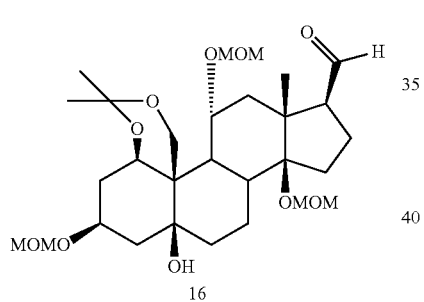

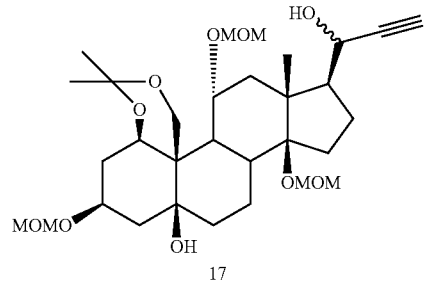

Preparation of Aldehyde 16:

To a solution of diol 15 (0.65 g, 1.10 mmol) in THF:H$_2$O (8:2) (20 mL) was added sodium periodate (0.70 g, 3.31 mmol) at ambient temperature. After being stirring for 1 h, the white precipitate was filtered off and the filtrate was diluted with water (20 mL). The mixture was extracted with ethyl acetate (3×20 mL) and the combined organic layers were dried over Na$_2$SO$_4$, filtered and the solvent was then removed in vacuo. The residue was purified by silica gel chromatography (hexanes/ethyl acetate, 7:3) to afford aldehyde 16 (0.38 g, 62%) as white solid: mp 129-135° C.; $^1$H NMR (400 MHz, CDCl$_3$) δ 9.66 (d, J=2.2 Hz, 1H), 4.90-4.32 (m, 9H), 4.23-3.94 (m, 2H), 3.78-3.54 (m, 1H), 3.51-3.13 (m, 9H), 2.56 (dd, J=9.7, 3.7 Hz, 1H), 2.28-1.15 (m, 21H), 1.12-0.88 (m, 4H); $^{13}$C NMR (100 MHz, CDCl$_3$) δ 204.3, 100.9, 96.8, 94.6, 92.2, 89.9, 75.2, 72.7, 70.8, 66.7, 60.7, 59.8, 56.1, 55.92, 55.52, 50.3, 47.8, 45.3, 43.1, 39.5, 35.9, 34.8, 29.4, 28.2, 25.0, 23.1, 22.9, 20.9, 17.8; HRMS (ESI) calcd for C$_{29}$H$_{48}$O$_{10}$Na(M+Na)$^+$ 579.3145. found 579.3118.

To a solution of aldehyde 16 (0.17 g, 0.30 mmol) in THF (10 mL) at −78° C. was added ethynylmagnesium bromide (0.5 M solution in THF, 6.11 mL, 3.05 mmol). After being stirred for 1 h, the reaction was quenched with saturated aqueous NH$_4$Cl (10 mL). The organic phase was separated and the aqueous phase was extracted with EtOAc (2×15 mL). The combined organic layers were dried over Na$_2$SO$_4$ and concentrated in vacuo. The obtained residue was purified by flash column chromatography (silica gel, hexanes/ethyl acetate, 7:3) to yield alkynol 17 (0.14 g, 79%) as white foam: $^1$H NMR (400 MHz, CDCl$_3$) δ 4.86-4.34 (m, 8H), 4.20 (t, J=24.7 Hz, 4H), 3.54 (dd, J=24.2, 20.5 Hz, 2H), 3.50-3.23 (m, 9H), 2.71 (s, 1H), 2.51-2.21 (m, 2H), 2.17-1.56 (m, 8H), 1.59-1.15 (m, 11H), 1.13 (s, 1H), 0.92 (s, 3H); $^{13}$C NMR (100 MHz, CDCl$_3$) δ 101.0, 96.5, 94.7, 92.8, 91.9, 86.1, 76.9, 72.6, 72.3, 71.0, 66.6, 64.1, 60.9, 56.1, 55.9, 55.5, 50.9, 47.1, 47.0, 43.0, 40.6, 38.5, 34.76, 34.40, 30.0, 29.3, 28.1, 25.1, 23.2, 21.6, 18.5; HRMS (ESI) calcd for C$_{31}$H$_{50}$O$_{10}$Na (M+Na)$^+$ 605.3302. found 605.3315.

Example 18

(3S,3aR,5R,5bR,9aR,11S,12aS,14bS)-3-((1-benzyl-1H-1,2,3-triazol-4-yl)(hydroxy)methyl)-5,11,14b-tris(methoxymethoxy)-3a,8,8-trimethylhexadecahydro-1H-cyclopenta[7,8]phenanthro[4,4a-d][1,3]dioxin-12a-ol (18)

Example 20

(1R,3S,5S,10R,11R,13R,14S,17S)-17-((1-benzyl-11'-1,2,3-triazol-4-yl)(hydroxy)methyl)-10-(hydroxymethyl)-13-methylhexadecahydro-1H-cyclopenta[a]phenanthrene-1,3,5,11,14-pentaol (20)

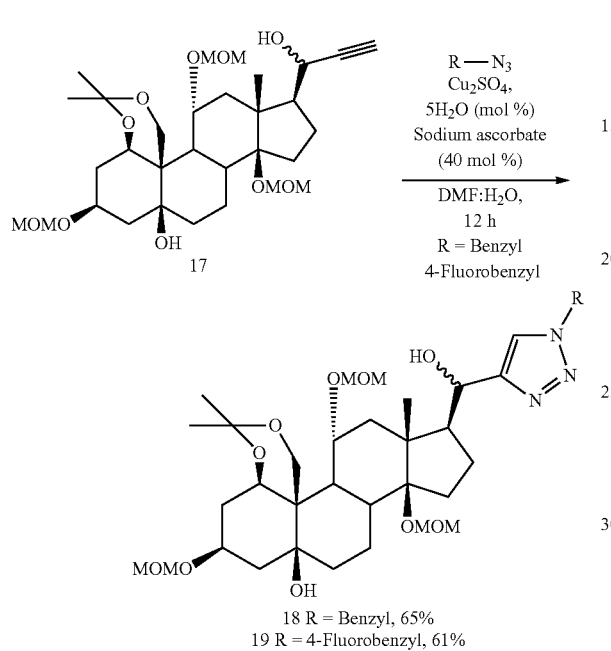

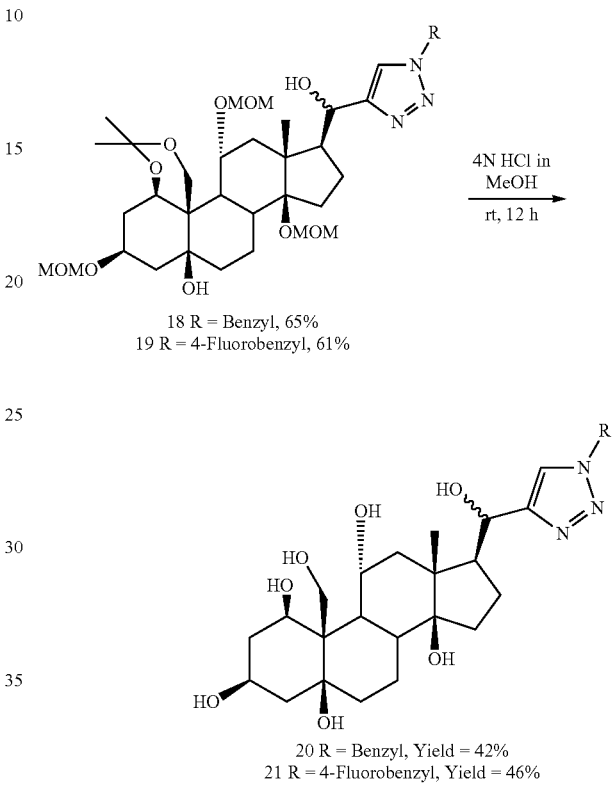

To a solution of the benzyl azide (19 mg, 0.14 mmol) and alkynol 17 (85 mg, 0.14 mmol) in DMF (2 mL) was added sodium ascorbate (11 mg, 0.057 mmol) in 1 mL water and the reaction mixture was stirred for 2 minutes. To the resultant mixture $CuSO_4 \cdot 5H_2O$ (7 mg, 0.028 mmol) in 1 mL water was added. The mixture was stirred at room temperature for 12 h, added water (4 mL), and extracted with EtOAc (3×5 mL). Evaporation of combined organic extracts afforded a green solid, which was purified by flash chromatography (hexanes/ethyl acetate, 2:8) to give compound 18 (66 mg, 65%) as white foam: $^1$H NMR (400 MHz, $CDCl_3$) δ 7.32 (s, 1H), 7.26 (m, 3H), 7.07 (dd, J=11.7, 5.3 Hz, 2H), 5.54-5.42 (m, 2H), 4.83-4.76 (m, 1H), 4.77-4.67 (m, 4H), 4.60 (d, J=7.5 Hz, 1H), 4.50 (d, J=12.2 Hz, 1H), 4.31 (s, 1H), 4.27 (s, 1H), 4.11 (s, 1H), 3.60 (d, J=12.3 Hz, 1H), 3.47-3.29 (m, 9H), 2.97 (td, J=12.0, 6.1 Hz, 1H), 2.44 (d, J=13.2 Hz, 1H), 2.18-2.02 (m, 2H), 2.01-1.85 (m, 2H), 1.78 (d, J=15.0 Hz, 2H), 1.72-1.17 (m, 15H), 1.06 (s, 3H).

Example 19

(3S,3aR,5R,5bR,9aR,11S,12aS,14bS)-3-((1-(4-fluorobenzyl)-1H-1,2,3-triazol-4-yl)(hydroxy)methyl)-5,11,14b-tris(methoxymethoxy)-3a,8,8-trimethylhexadecahydro-1H-cyclopenta[7,8]phenanthro[4,4a-d][1,3]dioxin-12a-ol (19)

Followed the procedure described for 18 to get the 19 (0.12 g, 61%).

The compound 18 (50 mg, 0.07 mmol) was dissolved in 4N HCl in MeOH (5 ml) and the solution was stirred at room temperature for 12 h. After completion of the reaction (monitored by TLC), the solvent was removed in vacuo. The residue was purified by column chromatography on silica gel (EtOAc: MeOH: $H_2O$) to give 20 (16 mg, 42%) white foam: $^1$H NMR (400 MHz, $CD_3OD$): δ 8.22 (s, 1H), 7.37 (s, 5H), 5.65 (s, 2H), 4.50-3.91 (m, 3H), 3.29 (m, 3H), 2.09-1.85 (m, 6H), 1.81-1.03 (m, 11H), 0.88 (s, 3H); HRMS (ESI) calcd for $C_{29}H_{42}N_3O_7$ (M+H)$^+$ 544.3023. found 544.3043.

Example 21

(1R,3S,5S,10R,11R,13R,14S,17S)-17-((1-(4-fluorobenzyl)-1H-1,2,3-triazol-4-yl)(hydroxy)methyl)-10-(hydroxymethyl)-13-methylhexadecahydro-1H-cyclopenta[a]phenanthrene-1,3,5,11,14-pentaol (21)

Followed the procedure described for 20 to get the 21 (25 mg, 46%): $^1$H NMR (400 MHz, $CDCl_3$) δ 7.80 (s, 1H), 7.42-7.31 (m, 2H), 7.17-7.06 (m, 2H), 5.58 (s, 2H), 4.83 (d, J=5.8 Hz, 1H), 4.37 (d, J=10.9 Hz, 1H), 4.30-3.95 (m, 3H), 2.48 (d, J=9.6 Hz, 1H), 2.23-1.82 (m, 6H), 1.77-1.25 (m, 12H), 1.01-0.80 (s, 3H). HRMS (ESI) calcd for $C_{29}H_{41}N_3O_7F$ (M+H)$^+$ 562.2929. found 562.2922.

Example 22

(3S,3aR,5R,5bR,9aR,11S,12aS,14bS)-3-(hydroxymethyl)-5,11,14b-tris(methoxymethoxy)-3a,8,8-trimethylhexadecahydro-1H-cyclopenta[7,8]phenanthro[4,4a-d][1,3]dioxin-12a-ol (22)

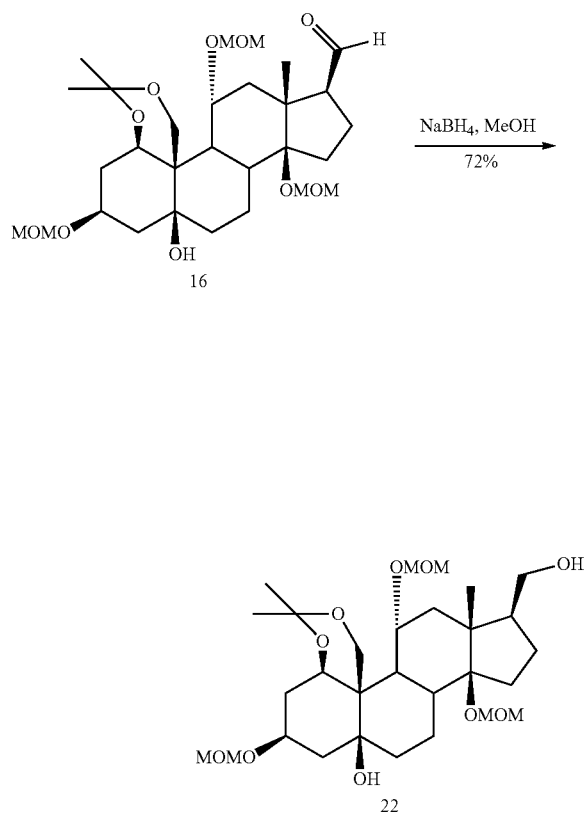

To a solution of aldehyde 16 (0.50 g, 0.89 mmol) in methanol (10 mL) at 0° C. was added sodium borohydride (0.10 g, 2.69 mmol). After being stirred for 30 min, the reaction was quenched with saturated aqueous NH$_4$Cl (15 mL) and extracted with ethyl acetate (3×15 mL). The organic layers were combined, dried over Na$_2$SO$_4$, filtered and the solvent was removed in vacuo. The resultant residue was purified by column chromatography (silica gel, hexanes/ethyl acetate, 1:1) to afford the corresponding alcohol 22 (0.36 g, 72%) as white solid: mp 154-158° C.; [α]$_D^{26}$+2.68 (c 1.30, CHCl$_3$); $^1$H NMR (400 MHz, CDCl$_3$) δ 4.64 (m, 7H), 4.47 (m, 2H), 4.10 (d, J=6.8 Hz, 2H), 3.69-3.50 (m, 3H), 3.45-3.26 (m, 9H), 2.30 (s, 2H), 2.18-1.69 (m, 9H), 1.63 (dd, J=14.6, 4.0 Hz, 1H), 1.56-1.19 (m, 11H), 1.03 (m, 1H), 0.89 (s, 3H); $^{13}$C NMR (100 MHz, CDCl$_3$) δ 100.9, 96.6, 94.6, 92.4, 91.5, 76.0, 72.7, 70.9, 66.7, 63.6, 60.8, 56.0, 55.9, 55.5, 49.1, 47.5, 47.2, 44.3, 41.4, 39.8, 35.4, 34.6, 29.9, 29.4, 25.7, 25.1, 23.1, 22.4, 18.0; HRMS (ESI) calcd for C$_{29}$H$_{50}$O$_{10}$Na (M+Na)$^+$ 581.3302. found 581.3282.

Example 23

((3S,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxin-3-yl)methyl-4-methylbenzenesulfonate (23)

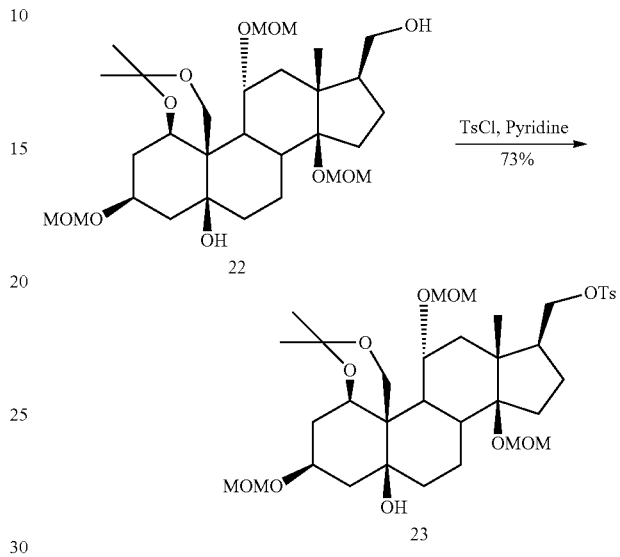

To a solution of alcohol 22 (0.10 g, 0.17 mmol) in CH$_2$Cl$_2$:pyridine (5:1, 6 mL) at 0° C. was added TsCl (0.05 g, 0.26 mmol). The reaction mixture was stirred at ambient temperature for 6 h, the reaction mixture was poured into water and extracted with CH$_2$Cl$_2$ (3×10 mL). The combined organic layers were dried over Na$_2$SO$_4$ and concentrated in vacuo. The residue was purified by column chromatography (silica gel, hexanes/ethyl acetate, 8:2) to give the tosylate 23 (0.09 g, 73%) as colorless oil: $^1$H NMR (400 MHz, CDCl$_3$) δ 7.77 (d, J=8.3 Hz, 2H), 7.33 (d, J=8.2 Hz, 2H), 4.77-4.50 (m, 8H), 4.51-4.38 (m, 1H), 4.20-3.99 (m, 3H), 3.92 (t, J=8.6 Hz, 1H), 3.57 (dd, J=20.2, 12.6 Hz, 1H), 3.41-3.33 (m, 3H), 3.31 (s, 3H), 3.29 (s, 3H), 2.55-2.38 (m, 4H), 2.18-1.87 (m, 4H), 1.87-1.64 (m, 5H), 1.62-1.48 (m, 1H), 1.49-1.17 (m, 12H), 1.12-0.95 (m, 1H), 0.74 (s, 3H).

Example 24

(3S,3aR,5R,5bR,9aR,11S,12aS,14bS)-3-(azidomethyl)-5,11,14b-tris(methoxymethoxy)-3a,8,8-trimethylhexadecahydro-1H-cyclopenta[7,8]phenanthro[4,4a-d][1,3]dioxin-12a-ol (24)

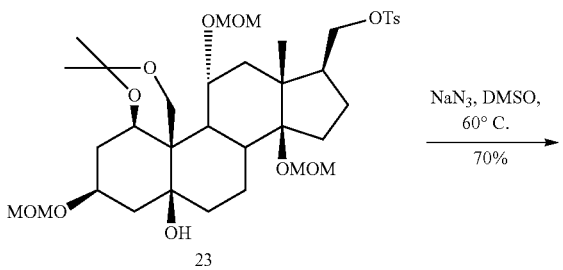

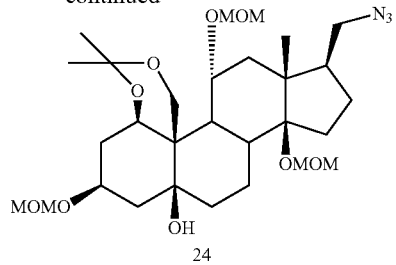

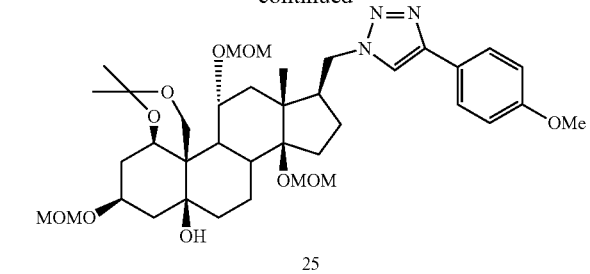

To a stirred solution of tosylate 23 (0.50 g, 0.70 mmol) in DMSO was added NaN$_3$ (0.13 g, 2.10 mmol) and the resulted reaction mixture was heated at 60° C. for 2.5 h. The reaction mixture was diluted with water (15 mL) and extracted with Et$_2$O (3×15 mL). The combined ether layers were washed with brine (15 mL) and dried over Na$_2$SO$_4$ and concentrated in vacuo. The residue was purified by column chromatography (silica gel, hexanes/ethyl acetate, 8:2) to afford azide 24 (0.28 g, 70%) as yellow liquid: $^1$H NMR (400 MHz, CDCl$_3$) δ 4.79-4.55 (m, 7H), 4.57-4.40 (m, 2H), 4.19 (t, J=13.1 Hz, 1H), 4.11 (s, 1H), 3.71-3.51 (m, 1H), 3.46-3.29 (m, 9H), 3.22-3.06 (m, 1H), 2.35 (tt, J=9.8, 6.6 Hz, 1H), 2.15-1.86 (m, 5H), 1.77 (ddd, J=22.5, 9.8, 5.3 Hz, 4H), 1.67-1.54 (m, 2H), 1.51-1.27 (m, 11H), 1.12 (dd, J=23.8, 10.7 Hz, 1H), 0.82 (s, 3H).

Example 25

(3S,3aR,5R,5bR,9aR,11S,12aS,14bS)-5,11,14b-tris(methoxymethoxy)-3-((4-(4-methoxyphenyl)-1H-1,2,3-triazol-1-yl)methyl)-3a,8,8-trimethylhexadecahydro-1H-cyclopenta[7,8]phenanthro[4,4a-d][1,3]dioxin-12a-ol (25)

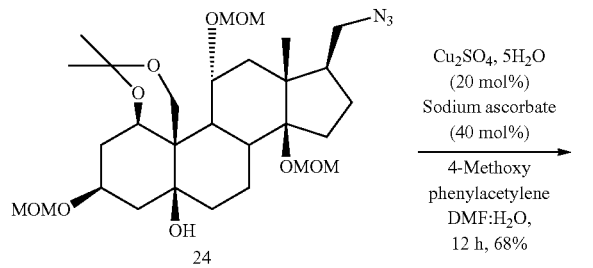

To a solution of the azide 24 (76 mg, 0.13 mmol, 1 eq.) and 4-methoxyphenyl acetylene (25 mg, 0.195 mmol, 1.5 eq.) in DMF (2 mL) was added sodium ascorbate (10 mg, 0.052 mmol) in 1 mL water and the reaction mixture was stirred for 2 minutes. To the resultant mixture CuSO$_4$.5H$_2$O (6 mg, 0.026 mmol) in 1 mL water was added. The mixture was stirred at room temperature for 12 h, added water (4 mL), and extracted with EtOAc (3×5 mL). Evaporation of combined organic extracts afforded a green solid, which was purified by flash chromatography (hexanes/ethyl acetate, 3:7) to give compound 25 (63 mg, 68%) as foam: $^1$H NMR (400 MHz, CDCl$_3$) δ 7.75-7.72 (m, 3H), 7.05-6.84 (m, 2H), 4.81-4.65 (m, 6H), 4.54-4.44 (m, 2H), 4.40 (dd, J=13.3, 3.8 Hz, 1H), 4.34-4.17 (m, 2H), 3.84 (s, 3H), 3.75-3.58 (m, 1H), 3.43-3.34 (m, 9H), 2.77-2.62 (m, 1H), 2.16-1.87 (m, 4H), 1.86-1.57 (m, 6H), 1.56-1.27 (m, 12H), 0.97 (s, 3H); $^{13}$C NMR (100 MHz, CDCl$_3$) δ 159.5, 147.5, 126.8, 123.5, 119.0, 114.2, 101.0, 96.2, 94.7, 92.8, 91.0, 74.9, 72.6, 70.9, 66.6, 60.8, 56.2, 55.9, 55.5, 55.3, 51.7, 47.5, 47.4, 47.3, 44.0, 40.4, 39.4, 35.2, 34.5, 29.5, 28.9, 27.0, 25.1, 23.1, 22.1, 18.2.

Example 26

(1R,3S,5S,10R,11R,13R,14S,17S)-10-(hydroxymethyl)-17-((4-(4-methoxyphenyl)-1H-1,2,3-triazol-1-yl)methyl)-13-methylhexadecahydro-1H-cyclopenta[a]phenanthrene-1,3,5,11,14-pentaol (26)

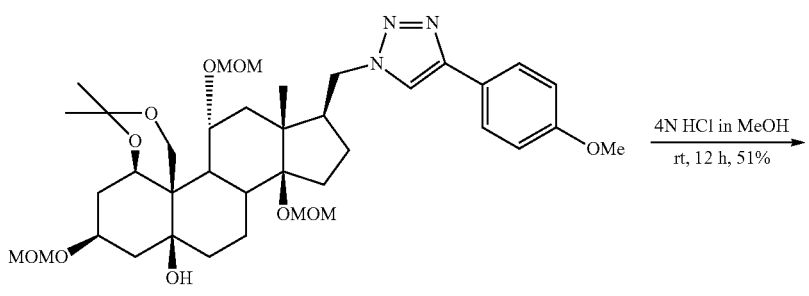

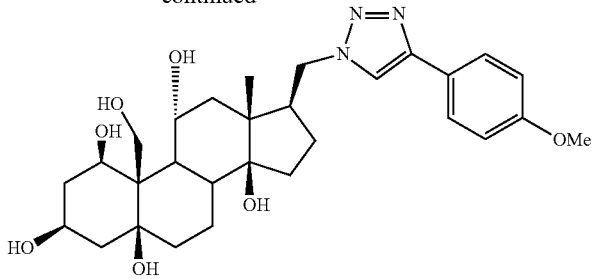

26

The compound 25 (0.050 g, 0.069 mmol) was dissolved in 4N HCl in MeOH (5 ml) and the solution was stirred at room temperature for 12 h. After completion of the reaction (monitored by TLC), the solvent was removed in vacuo. The residue was purified by column chromatography (silica gel, EtOAc/MeOH, 8:2 with 2% H$_2$O) to give 26 (0.019 g, 51%) as white foam: $^1$H NMR (400 MHz, CD$_3$OD) δ 8.59 (s, 1H), 7.72 (d, J=8.4 Hz, 2H), 7.03 (d, J=8.3 Hz, 2H), 4.71-4.50 (m, 2H), 4.47-3.98 (m, 3H), 3.82 (s, 3H), 3.27 (m, 2H), 2.42-1.17 (m, 20H). HRMS (ESI) calcd for C$_{29}$H$_{42}$N$_3$O$_7$ (M+H)$^+$ 544.3023. found 544.3035.

Example 28

(3R,3aR,5R,5bR,9aR,11S,12aS,14bS)-3-ethynyl-5,11,14b-tris(methoxymethoxy)-3a,8,8-trimethylhexadecahydro-1H-cyclopenta[7,8]phenanthro[4,4a-d][1,3]dioxin-12a-ol (28)

hexanes, 9:1) gave alkyne 28 (0.140 g, 71%) as yellow foam. Formation of C17 epimer (10%) was observed which was isolated by flash chromatography in next step. $^1$H NMR (400 MHz, CDCl$_3$) δ 5.09-4.36 (m, 9H), 4.09 (s, 1H), 3.77 (dd, J=16.6, 10.3 Hz, 2H), 3.51-3.25 (m, 9H), 2.71 (d, J=5.1 Hz, 1H), 2.30-1.59 (m, 11H), 1.60-1.17 (m, 11H), 1.17-0.88 (m, 4H); $^{13}$C NMR (100 MHz, CDCl$_3$) δ 100.9, 97.3, 94.6, 92.7, 89.9, 84.6, 76.0, 72.9, 70.8, 70.4, 66.9, 60.5, 56.0, 55.8, 55.5, 48.8, 48.0, 45.9, 40.6, 40.0, 38.9, 36.2, 35.0, 29.3, 27.4, 25.3, 25.0, 23.1, 22.8, 17.6; HRMS (ESI) calcd for C$_{30}$H$_{49}$O$_9$(M+H)$^+$ 553.3377. found 553.3359.

Example 29

(3S,3aR,5R,5bR,9aR,11S,12aS,14bS)-3-(1-benzyl-1H-1,2,3-triazol-4-yl)-5,11,14b-tris(methoxymethoxy)-3a,8,8-trimethylhexadecahydro-1H-cyclopenta[7,8]phenanthro[4,4a-d][1,3]dioxin-12a-ol (29)

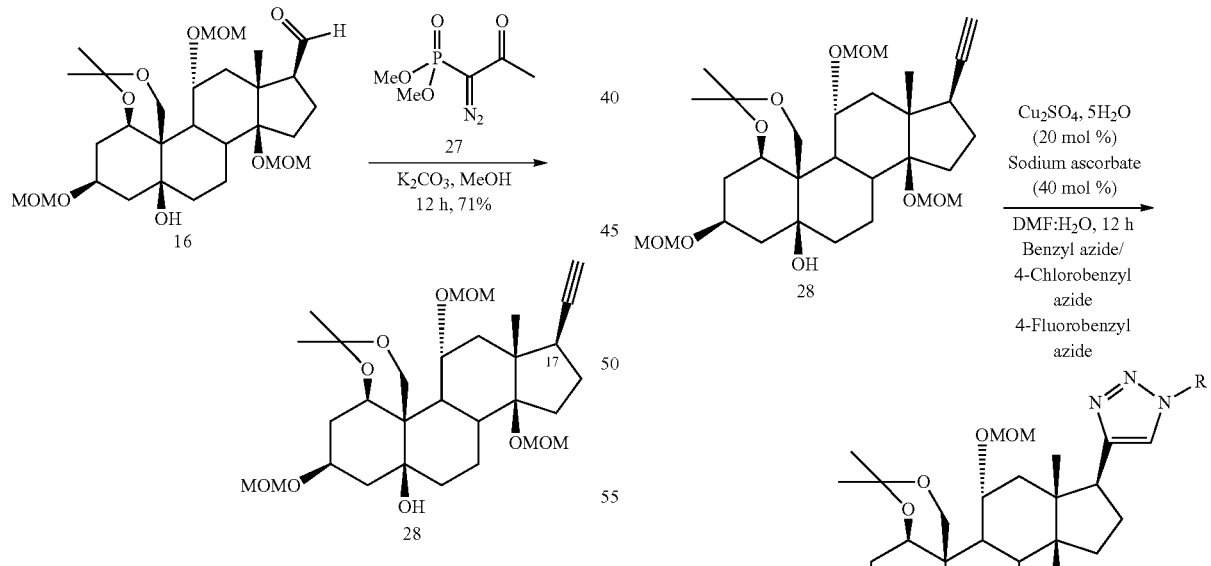

29 R = Benzyl, 58%
30 R = 4-Chlorobenzyl, 56%
31 R = 4-Fluorobenzyl, 66%

To a solution of 27 (0.103 g, 0.53 mmol) in MeOH (3 mL) was added K$_2$CO$_3$ (0.148 g, 1.07 mmol) and stirred for 5 min. A solution of the aldehyde 16 (0.20 g, 0.359 mmol) in MeOH (2 mL) was added to the above mixture at 0° C. After being stirred at room temperature for 3 h, the reaction mixture was diluted with H$_2$O (10 mL) and extracted with EtOAc (3×10 mL), washed with brine (10 mL), dried over Na$_2$SO$_4$, filtered, and concentrated under reduced pressure. Purification by flash chromatography (silica gel, acetone/

To a stirred solution of the benzyl azide (49 mg, 0.375 mmol) and alkyne 28 (138 mg, 0.250 mmol) in DMF (2 mL)

was added sodium ascorbate (20 mg, 0.1 mmol) in 1 mL water and the reaction mixture was stirred for two minutes. To the resultant mixture $CuSO_4 \cdot 5H_2O$ (12 mg, 0.05 mmol) in 1 mL water was added. The mixture was stirred at room temperature for 12 h, added water (5 mL), and extracted with EtOAc (3×10 mL). Evaporation of combined organic extracts afforded a green solid, which was purified by flash chromatography (hexanes/acetone, 7:3) to give compound 29 (99 mg, 58%) as white foam: $^1$H NMR (400 MHz, $CDCl_3$) δ 7.39-7.29 (m, 3H), 7.25-7.19 (m, 2H), 7.18 (s, 1H), 5.49 (q, J=14.9 Hz, 2H), 4.91 (t, J=3.3 Hz, 1H), 4.82 (d, J=7.5 Hz, 1H), 4.76-4.64 (m, 5H), 4.53 (t, J=7.1 Hz, 1H), 4.42 (d, J=12.2 Hz, 1H), 4.08 (s, 1H), 3.68 (ddd, J=13.6, 10.8, 6.1 Hz, 2H), 3.38 (d, J=2.8 Hz, 6H), 3.29-3.17 (m, 1H), 3.09 (s, 3H), 2.25-1.90 (m, 7H), 1.87-1.65 (m, 3H), 1.60-1.40 (m, 3H), 1.40-1.29 (m, 6H), 1.26 (m, 3H), 1.02 (s, 3H); $^{13}$C NMR (100 MHz, $CDCl_3$) δ 147.7, 134.9, 129.0, 128.6, 127.8, 121.1, 100.9, 97.3, 94.6, 93.0, 91.1, 76.4, 73.0, 70.8, 66.9, 60.4, 56.1, 55.5, 54.0, 48.71, 48.01, 45.8, 45.7, 40.6, 39.2, 36.2, 34.9, 29.6, 25.81, 25.14, 25.01, 23.0, 22.8, 18.23; HRMS (ESI) calcd for $C_{37}H_{56}N_3O_9$ $(M+H)^+$ 686.4017. found 686.4005.

Example 30

(3S,3aR,5R,5bR,9aR,11S,12aS,14bS)-3-(1-(4-chlorobenzyl)-1H-1,2,3-triazol-4-yl)-5,11,14b-tris(methoxymethoxy)-3a,8,8-trimethylhexadecahydro-1H-cyclopenta[7,8]phenanthro[4,4a-d][1,3]dioxin-12a-ol (30)

Followed the procedure described for 29 to get the 30 (0.145 g, 56%). $^1$H NMR (400 MHz, $CDCl_3$) δ 7.38-7.28 (m, 2H), 7.22-7.09 (m, 3H), 5.46 (q, J=15.1 Hz, 2H), 4.91 (t, J=3.2 Hz, 1H), 4.83 (d, J=7.5 Hz, 1H), 4.73 (t, J=3.4 Hz, 2H), 4.71-4.65 (m, 3H), 4.53 (d, J=6.4 Hz, 1H), 4.43 (d, J=12.2 Hz, 1H), 4.15-4.02 (m, 1H), 3.69 (ddd, J=13.1, 10.9, 5.6 Hz, 2H), 3.38 (t, J=4.4 Hz, 6H), 3.31-3.18 (m, 1H), 3.11 (s, 3H), 2.15-1.91 (m, 5H), 1.84-1.66 (m, 2H), 1.61-1.41 (m, 3H), 1.40-1.16 (m, 11H), 1.00 (s, 4H). $^{13}$C NMR (100 MHz, $CDCl_3$) δ 147.9, 134.7, 133.4, 129.30, 129.17, 121.1, 100.9, 97.3, 94.6, 93.0, 91.0, 76.4, 73.0, 70.8, 66.9, 60.4, 56.1, 55.5, 53.2, 48.7, 48.0, 45.8, 45.7, 40.6, 39.2, 36.2, 35.0, 29.6, 29.3, 25.7, 25.1, 25.0, 23.1, 22.8, 18.2. HRMS (ESI) calcd for $C_{37}H_{55}N_3O_9$ Cl $(M+H)^+$ 720.3627. found 720.3644.

Example 31

(3S,3aR,5R,5bR,9aR,11S,12aS,14bS)-3-(1-(4-fluorobenzyl)-1H-1,2,3-triazol-4-yl)-5,11,14b-tris(methoxymethoxy)-3a,8,8-trimethylhexadecahydro-1H-cyclopenta[7,8]phenanthro[4,4a-d][1,3]dioxin-12a-ol (31)

Followed the procedure described for 29 to get the 31(0.15 g, 66%). $^1$H NMR (400 MHz, $CDCl_3$) δ 7.25-7.12 (m, 3H), 7.03 (t, J=8.6 Hz, 2H), 5.45 (q, J=15.2 Hz, 2H), 4.94-4.86 (m, 1H), 4.82 (t, J=8.3 Hz, 1H), 4.76-4.63 (m, 5H), 4.59-4.37 (m, 3H), 3.76-3.56 (m, 2H), 3.40-3.30 (m, 7H), 3.23 (dd, J=18.2, 8.4 Hz, 1H), 3.09 (s, 2H), 2.22-1.87 (m, 6H), 1.86-1.63 (m, 2H), 1.56-1.28 (m, 9H), 1.24 (d, J=4.7 Hz, 2H), 1.07-0.95 (m, 2H), 0.44 (s, 1H).

Example 32

(1R,3S,5S,10R,11R,13R,14S,17S)-17-(1-benzyl-1H-1,2,3-triazol-4-yl)-10-(hydroxymethyl)-13-methyl-hexadecahydro-1H-cyclopenta[a]phenanthrene-1,3,5,11,14-pentaol (32)

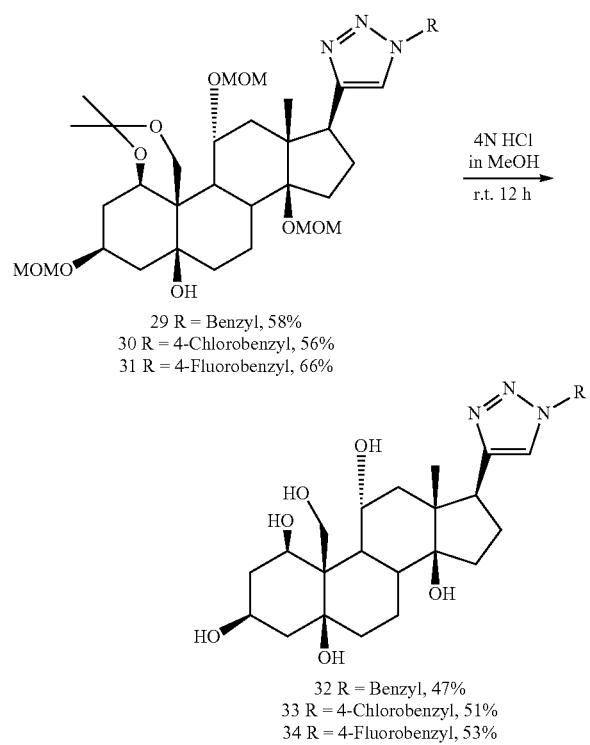

29 R = Benzyl, 58%
30 R = 4-Chlorobenzyl, 56%
31 R = 4-Fluorobenzyl, 66%

32 R = Benzyl, 47%
33 R = 4-Chlorobenzyl, 51%
34 R = 4-Fluorobenzyl, 53%

The compound 29 (0.05 g, 0.072 mmol) was dissolved in 4N HCl in MeOH (5 ml) and the solution was stirred at room temperature for 12 h. After completion of the reaction, the solvent was removed in vacuo. The residue was purified by column chromatography on silica gel (EtOAc/MeOH, 8:2 with 2% $H_2O$) to give the 32 (0.017 g, 47%) as white solid: mp 109-111° C.; $[\alpha]_D^{26}$+0.60 (c=1.00, MeOH). $^1$H NMR (400 MHz, $CD_3OD$) δ 7.81 (s, 1H), 7.47-7.19 (m, 5H), 5.58 (s, 2H), 4.51-3.95 (m, 4H), 3.51-3.37 (m, 1H), 2.12 (m 7H), 1.84-1.17 (m, 9H), 1.10-0.80 (m, 4H). $^{13}$C NMR (100 MHz, $CD_3OD$) δ 148.6, 136.4, 130.1, 129.77, 129.10, 125.0, 87.3, 78.7, 78.4, 75.8, 68.6, 62.7, 55.4, 52.3, 50.0, 47.1, 39.0, 38.9, 38.2, 37.4, 37.0, 31.5, 26.0, 25.3, 21.4, 19.6. HRMS (ESI) calcd for $C_{28}H_{40}N_3O_6$ $(M+H)^+$ 514.2917. found 514.2908.

Example 33

(1R,3S,5S,10R,11R,13R,14S,17S)-17-(1-(4-chlorobenzyl)-1H-1,2,3-triazol-4-yl)-10-(hydroxymethyl)-13-methylhexadecahydro-1H-cyclopenta[a]phenanthrene-1,3,5,11,14-pentaol (33)

Followed the procedure described for 32 to get the 33 (0.027 g, 51%): $^1$H NMR (400 MHz, $CD_3OD$) δ 8.26-8.08 (m, 1H), 7.39 (dd, J=21.4, 8.5 Hz, 4H), 5.66 (d, J=9.0 Hz, 2H), 4.45-4.11 (m, 4H), 3.56-3.39 (m, 1H), 2.38-2.03 (m, 6H), 1.82-1.24 (m, 10H), 1.11-0.79 (m, 4H).

Example 34

(1R,3S,5S,10R,11R,13R,14S,17S)-17-(1-(4-fluorobenzyl)-1H-1,2,3-triazol-4-yl)-10-(hydroxymethyl)-13-methylhexadecahydro-1H-cyclopenta[a]phenanthrene-1,3,5,11,14-pentaol (34)

Followed the procedure described for 32 to get the 34 (0.04 g, 53%): mp 166-168° C.; $^1$H NMR (400 MHz, CD$_3$OD) δ 7.83-7.74 (s, 0.7H), 7.67 (s, 0.3H), 7.42-7.21 (m, 2H), 7.09 (dd, J=12.2, 5.2 Hz, 2H), 5.60-5.38 (m, 2H), 4.47-3.84 (m, 4H), 3.49-3.35 (m, 1H), 2.37-1.04 (m, 16H), 1.05-0.76 (m, 3H), 0.70-0.55 (m, 1H); HRMS (ESI) calcd for C$_{28}$H$_{39}$FN$_3$O$_6$ (M+H)$^+$ 532.2823. found 532.2807.

Example 35

12a-hydroxy-5,11,14b-tris(methoxymethoxy)-3a,8,8-trimethylhexadecahydro-1H-cyclopenta[7,8]phenanthro[4,4a-d][1,3]dioxine-3-carbaldehyde oxime (35)

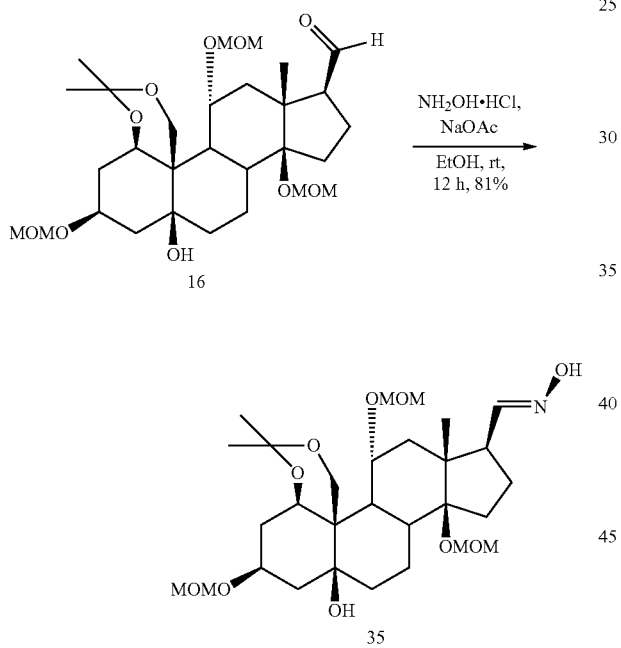

To a solution of aldehyde 16 (0.60 g, 1.07 mmol) in EtOH (10 mL) at room temperature were added NH$_2$OH.HCl (0.29 g, 4.31 mmol) and NaOAc (0.39 g, 4.85 mmol). After being stirred for 1 h, the reaction mixture was diluted with water (15 mL) and extracted with EtOAc (3×15 mL). The combined organic layers were dried over Na$_2$SO$_4$ and concentrated in vacuo. The residue was purified by column chromatography (silica gel, hexanes/ethyl acetate, 7:3) to give oxime 35 (0.49 g, 81%) as colorless foam: $^1$H NMR (400 MHz, CDCl$_3$) δ 7.39 (dd, J=14.0, 7.3 Hz, 0.7H), 6.81 (d, J=7.7 Hz, 0.3H), 4.79-4.63 (m, 7H), 4.57 (d, J=13.2 Hz, 1H), 4.54-4.42 (m, 1H), 4.23-3.95 (m, 2H), 3.74-3.59 (m, 1H), 3.42-3.31 (m, 9H), 2.89 (dd, J=15.6, 7.8 Hz, 1H), 2.15-1.28 (m, 22H), 1.14-0.95 (m, 2H), 0.91-0.81 (m, 2H); $^{13}$C NMR (100 MHz, CDCl$_3$) δ 154.1, 101.0, 96.6, 95.9, 94.6, 92.5, 90.5, 74.6, 72.9, 72.8, 70.9, 66.6, 60.8, 56.3, 55.9, 55.5, 49.5, 48.9, 47.5, 44.4, 40.2, 35.4, 34.6, 29.5, 26.2, 25.0, 23.1, 22.4, 19.2; HRMS (ESI) calcd for C$_{29}$H$_{50}$NO$_{10}$ (M+H)$^+$ 572.3435. found 572.3422.

Example 36

(3S,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxine-3-carbonitrile (36)

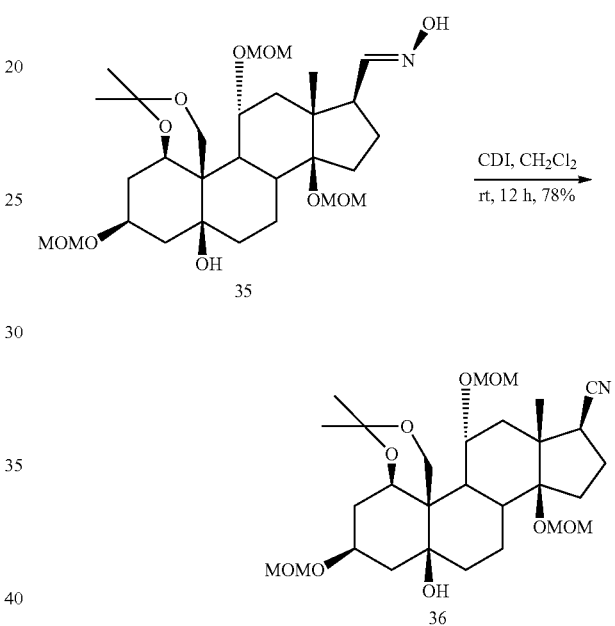

To a stirred solution of oxime 35 (0.30 g, 0.525 mmol) in CH$_2$Cl$_2$ (10 mL) and 1,1'-carbonyldiimidazole (0.297 g, 1.87 mmol) was added at room temperature. After being stirred for 12 h, saturated aqueous NH$_4$Cl (10 mL) was added and the mixture was extracted with CH$_2$Cl$_2$ (3×10 mL). The combined organic layers were dried over Na$_2$SO$_4$ and concentrated to a residue, which was purified by flash chromatography (silica gel, hexanes/ethyl acetate, 8:2) to furnish nitrile 36 (0.22 g, 78%) as colorless foam: [α]$_D^{26}$+ 21.2 (c 2.15, CHCl$_3$); $^1$H NMR (400 MHz, CDCl$_3$) δ 4.75-4.64 (m, 6H), 4.52-4.42 (m, 2H), 4.20 (q, J=5.2 Hz, 1H), 4.07 (d, J=17.8 Hz, 1H), 3.59 (d, J=12.3 Hz, 1H), 3.42-3.29 (m, 9H), 3.17 (dd, J=8.9, 7.5 Hz, 1H), 2.17-2.06 (m, 3H), 2.05-1.87 (m, 3H), 1.86-1.65 (m, 5H), 1.56-1.26 (m, 11H), 1.15 (s, 3H), 1.09-0.95 (m, 1H); $^{13}$C NMR (100 MHz, CDCl$_3$) δ 120.8, 101.1, 96.3, 94.6, 92.8, 89.1, 74.8, 72.6, 70.8, 66.4, 60.7, 56.4, 56.2, 55.5, 48.2, 47.4, 44.3, 40.2, 39.2, 38.4, 35.3, 34.6, 29.5, 29.4, 27.1, 25.0, 23.1, 22.2, 20.4; HRMS (ESI) calcd for C$_{29}$H$_{48}$NO$_9$ (M+H)$^+$ 554.3329. found 554.3327.

Example 37

(3S,3aR,5R,5bR,9aR,11S,12aS,14bS)-5,11,14b-tris(methoxymethoxy)-3a,8,8-trimethyl-3-(2,2,2-trifluoro-1-hydroxyethyl)hexadecahydro-1H-cyclopenta[7,8]phenanthro[4,4a-d][1,3]dioxin-12a-ol (37)

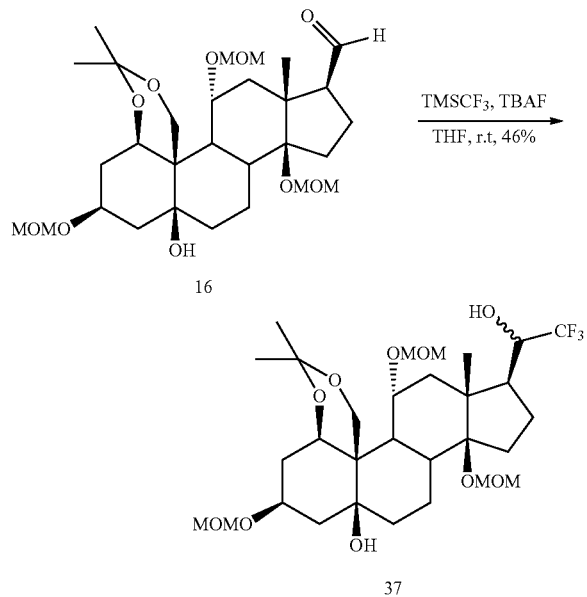

To a stirred solution of aldehyde 16 (0.20 g, 0.36 mmol) in THF (10 mL) were added TMSCF$_3$ (0.09 mL, 0.46 mmol, 0.5 M THF solution) and catalytic amount of TBAF. After 1 h, an additional TBAF (0.5 mL, 0.5 mmol, 1M solution in THF) was added and stirred for 6 h at room temperature. The reaction mixture was concentrated and purified on column chromatography (silica gel, hexanes/ethyl acetate, 1:1) to furnish compound 37 (0.10 g, 46%) as colorless foam: $^1$H NMR (400 MHz, CDCl$_3$) δ 4.86-4.43 (m, 8H), 4.33 (s, 1H), 4.17-4.03 (m, 1H), 3.91-3.67 (m, 1H), 3.54 (d, J=12.2 Hz, 1H), 3.45-3.28 (m, 9H), 2.78 (td, J=12.5, 5.5 Hz, 1H), 2.42-2.37 (m, 1H), 2.21-1.25 (m, 19H), 1.18-1.01 (m, 2H), 0.99-0.78 (m, 3H). HRMS (ESI) calcd for C$_{30}$H$_{50}$F$_3$O$_{10}$ (M+H)$^+$ 627.3356. found 627.3367.

Example 38

(3S,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxine-3-carboxylic acid (38)

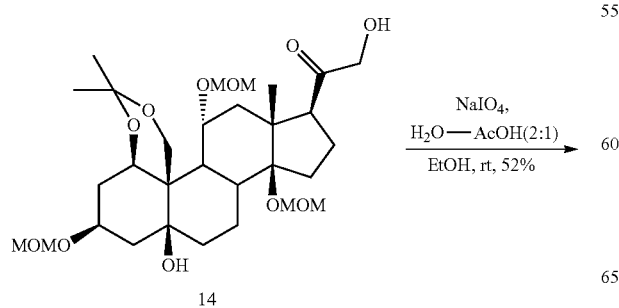

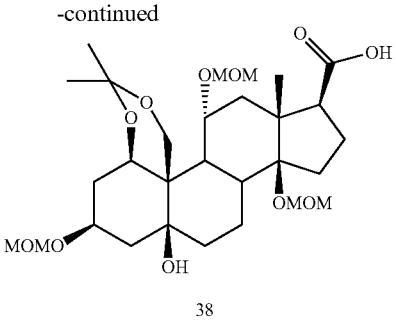

To a solution of hydroxyl ketone 14 (0.20 g, 0.34 mmol) in EtOH:H$_2$O (1:1) 10 mL were added AcOH (1 mL) and NaIO$_4$ (0.21 g, 1.02 mmol). After being stirred for 1 h, the reaction mixture was diluted with H$_2$O (10 mL) and extracted with CH$_2$Cl$_2$ (3×10 mL). The combined organic layers were dried over Na$_2$SO$_4$ and concentrated to a residue, which was purified by flash chromatography (silica gel, hexanes/ethyl acetate, 6:4) to furnish acid 38 (0.10 g, 52%) as white foam: [α]$_D^{26}$ -5.47 (c 1.09, CHCl$_3$); $^1$H NMR (400 MHz, CDCl$_3$) δ 4.84 (d, J=6.8 Hz, 1H), 4.81-4.67 (m, 3H), 4.59 (t, J=4.4 Hz, 3H), 4.55-4.36 (m, 3H), 4.12 (s, 1H), 3.57 (t, J=10.6 Hz, 1H), 3.45 (dt, J=17.0, 8.5 Hz, 1H), 3.42-3.31 (m, 9H), 2.28-2.02 (m, 4H), 1.96 (dd, J=14.8, 3.1 Hz, 1H), 1.84 (dt, J=18.2, 9.5 Hz, 4H), 1.66 (ddd, J=26.9, 16.7, 9.5 Hz, 1H), 1.58-1.26 (m, 11H), 1.20-1.01 (m, 1H), 0.86 (s, 3H); $^{13}$C NMR (100 MHz, CDCl$_3$) δ 177.8, 101.1, 95.1, 94.6, 92.8, 90.4, 73.9, 72.6, 70.9, 66.3, 60.8, 56.3, 56.1, 55.6, 51.2, 47.4, 47.0, 43.4, 40.9, 36.1, 34.8, 34.4, 29.6, 29.4, 25.9, 25.1, 23.2, 21.8, 20.6; HRMS (ESI) calcd for C$_{29}$H$_{49}$O$_{11}$ (M+H)$^+$ 573.3275. found 573.3257.

Example 39, 40 and 41

4a'-methyl-4',4a',7',8'-tetrahydro-3'H-spiro[[1,3]dithiolane-2,2'-naphthalen]-5'(6'H)-one (39) 4a'-methyl-4',4a',5',6',7',8'-hexahydro-3'H-spiro[[1,3]dithiolane-2,2'-naphthalene]-5'-carbaldehyde (40) 8a-methyl-6-oxo-1,2,3,4,6,7,8,8a-octahydronaphthalene-1-carbaldehyde (41)

Formula II compounds of the present invention synthesized from commercially available Wieland-Miescher ketone (+/−). Compounds 39, 40 and 41 were synthesized according to the following scheme from Paquette et al, *J. Am. Chem. Soc.* 1994, 116, 3367-3374.

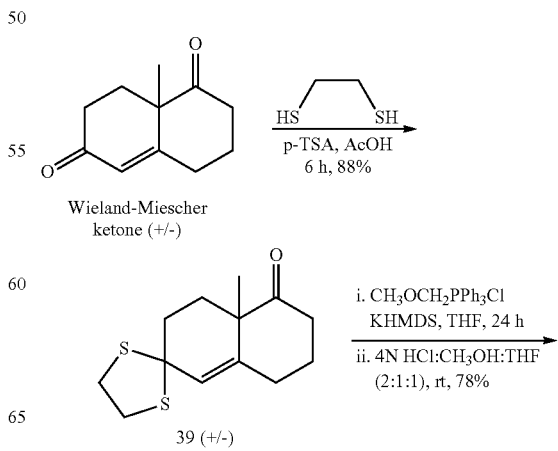

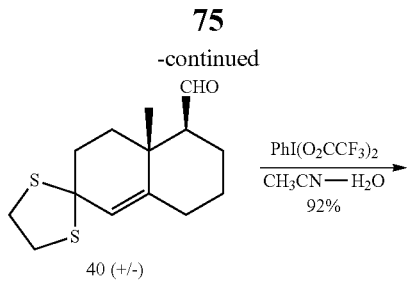

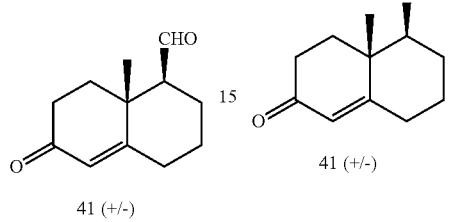

Example 42

8a-methyl-6-oxo-1,2,3,4,6,7,8,8a-octahydronaphthalene-1-carbaldehyde bis(amidinohydrazone) (42)

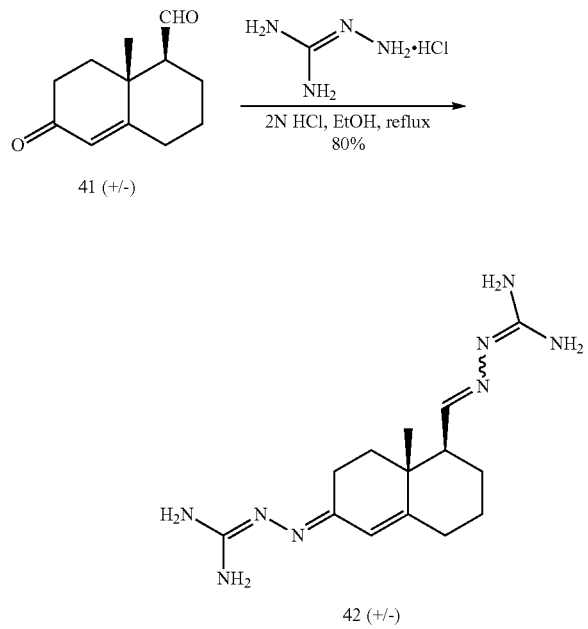

To a 0.05 M solution of the ketone-aldehyde 41 (40 mg, 0.20 mmol) in EtOH (6 mL) were added aminoguanidine hydrochloride (48 mg, 0.43 mmol) and 1 equiv of 2 N HCl in EtOH were added. The mixture was heated to reflux for 45 min, then cooled to room temperature, concentrated to dryness, and crystallized to obtain the corresponding amidinohydrazone 42 (50 mg, 80%) as white foam: $^1$H NMR (400 MHz, CD$_3$OD) δ 7.44 (dt, J=15.2, 8.1 Hz, 1H), 7.15 (s, 1H), 3.13-3.12 (m, 1H), 3.09-2.79 (m, 1H), 2.70-1.94 (m, 4H), 1.72-1.45 (m, 4H), 1.37-0.80 (m, 4H). HRMS (ESI) calcd for C$_{14}$H$_{25}$N$_8$ (M+H)$^+$ 305.2202. found 305.2204.

Example 43

5-ethynyl-4-a-methyl-4,4-a,5,6,7,8-hexahydronaphthalen-2(3H)-one (43)

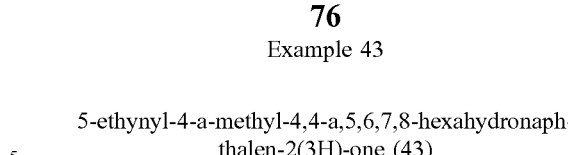
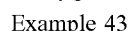
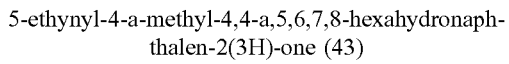

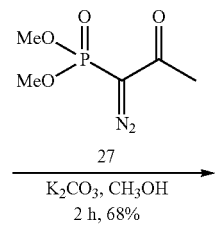

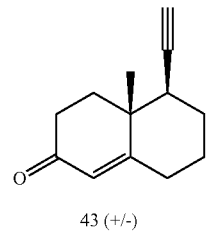

To a solution of Bestmann reagent 27 (0.60 g, 3.12 mmol) in MeOH (10 mL) were added K$_2$CO$_3$ (0.86 g, 6.25 mmol) and stirred for 10 mint at 0° C., and subsequently a solution of the aldehyde 41 (0.40 g, 2.08 mmol) in MeOH (5 mL). After being stirred at room temperature for 8 h, the reaction mixture was treated with saturated aqueous NaHCO$_3$ and methanol was removed by evaporation. The residue was dissolved in EtOAc (30 mL) and washed with water, dried over Na$_2$SO$_4$ and concentrated in vacuo to give crude residue, which was purified by column chromatography (silica gel, EtOAc/hexanes, 2:8) to get 43 (0.26 g, 68%) as solid: $^1$H NMR (400 MHz, CDCl$_3$) δ 5.91-5.67 (m, 1H), 2.61-2.18 (m, 5H), 2.01-1.71 (m, 4H), 1.68-1.55 (m, 1H), 1.51-1.16 (m, 5H).

Example 44

5-(1-benzyl-1H-1,2,3-triazol-4-yl)-4-a-methyl-4,4a,5,6,7,8-hexahydronaphthalen-2(3H)-one (44)

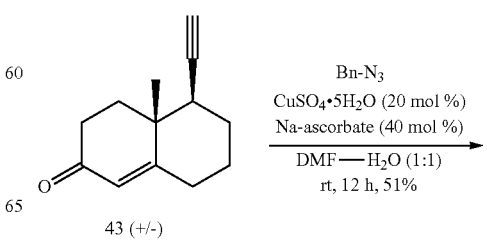

-continued

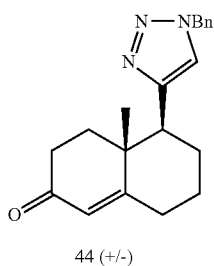

44 (+/-)

A solution of the benzyl azide (0.21 g, 1.59 mmol) in a mixture H$_2$O/DMF (1:1) (6 mL) was added to alkyne 43 (0.20 g, 1.06 mmol) in a vial. Then CuSO$_4$·5H$_2$O (52 mg, 0.21 mmol) and sodium ascorbate (84 mg, 0.42 mmol) were added. The mixture was stirred at room temperature for 12 h, quenched with water (10 mL), and extracted with EtOAc (3×10 mL). Usual workup afforded a green solid, which was purified by flash chromatography (silica gel, EtOAc/hexanes, 4:6) to give compound 44 (0.17 g, 51%) as white solid: $^1$H NMR (400 MHz, CDCl$_3$) δ 7.49-7.37 (m, 3H), 7.35-7.26 (m, 3H), 5.85 (d, J=1.6 Hz, 1H), 5.64-5.48 (m, 2H), 2.89 (dd, J=13.1, 3.4 Hz, 1H), 2.60-2.46 (m, 1H), 2.45-2.31 (m, 3H), 2.16 (qd, J=13.4, 3.7 Hz, 1H), 2.09-1.96 (m, 2H), 1.85 (d, J=13.6 Hz, 1H), 1.76 (dt, J=13.6, 4.3 Hz, 1H), 1.56 (ddd, J=16.2, 10.2, 5.5 Hz, 1H), 1.15 (s, 3H); $^{13}$C NMR (100 MHz, CDCl$_3$) δ 199.5, 169.3, 148.2, 134.8, 129.1, 128.7, 127.8, 124.8, 121.5, 54.0, 46.3, 35.9, 33.7, 32.7, 27.6, 26.3, 17.8; HRMS (ESI) calcd for C$_{20}$H$_{24}$N$_3$O (M+H)$^+$ 322.1919. found 322.1910.

Example 45

5-(1-benzyl-1H-1,2,3-triazol-4-yl)-4-a-methyl-4,4a,5,6,7,8-hexahydronaphthalen-2(3H)-one amidinohydrazone (45)

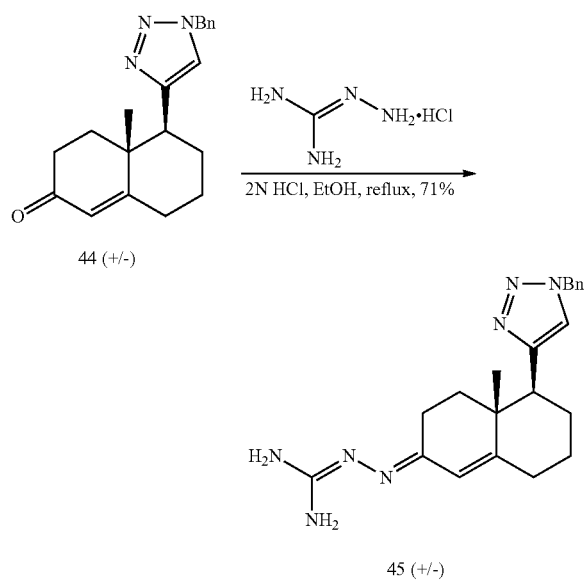

45 (+/-)

To a 0.05 M solution of 44 (116 mg, 0.36 mmol) in EtOH (10 mL), 1.0 equiv of the aminoguanidine hydrochloride (39 mg, 0.36 mmol) and 1 equiv of 2 N HCl in EtOH (0.18 mL) were added. The mixture was heated to reflux for 45 min, then cooled to room temperature, concentrated to dryness, and crystallized to obtain the corresponding amidinohydrazone 45 (95 mg, 71%) as yellow foam: $^1$H NMR (400 MHz, CD$_3$OD) δ 7.99-7.83 (m, 1H), 7.38-7.15 (m, 5H), 5.96 (t, J=7.2 Hz, 1H), 5.60-5.46 (m, 2H), 2.75 (td, J=13.1, 3.3 Hz, 1H), 2.65-2.22 (m, 3H), 2.22-2.01 (m, 2H), 2.01-1.84 (m, 1H), 1.77-1.60 (m, 2H), 1.58-1.27 (m, 2H), 1.30-1.04 (m, 1H), 1.04-0.90 (m, 3H); HRMS (ESI) calcd for C$_{21}$H$_{28}$N$_7$ (M+H)$^+$ 378.2406. found 378.2396.

Example 46

5-hydroxy-4a-methyl-4,4a,5,6,7,8-hexahydronaphthalen-2(3H)-one (46)

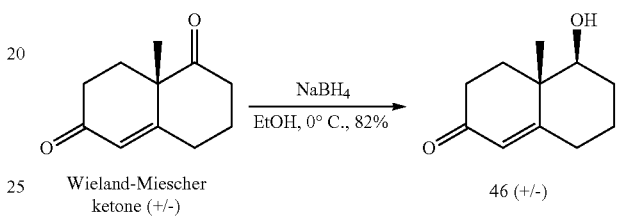

To a solution of Wieland-Miescher ketone (0.50 g, 2.80 mmol) in EtOH (18 mL) was added NaBH$_4$ (40 mg, 1.10 mmol) at 0° C. and reaction was stirred for 5 min. AcOH (0.5 mL) was added to the reaction and stirred for an additional 5 minutes. Volatiles were removed and diluted with EtOAc (30 mL), washed with brine, dried over Na$_2$SO$_4$. Purification by flash chromatography (EtOAc:hexane 1:3) gave the hydroxy ketone 46 (0.41 g, 82%) as colorless liquid: $^1$H NMR (400 MHz, CDCl$_3$) δ 5.74 (d, J=1.8 Hz, 1H), 3.39 (dd, J=11.6, 4.3 Hz, 1H), 2.66-2.51 (m, 1H), 2.48-2.23 (m, 3H), 2.25-2.08 (m, 2H), 1.90-1.74 (m, 3H), 1.73-1.61 (m, 1H), 1.46-1.28 (m, 1H), 1.16 (s, 3H); $^{13}$C NMR (100 MHz, CDCl$_3$) δ 199.9, 169.1, 125.3, 78.0, 41.6, 34.2, 33.7, 32.0, 30.2, 23.1, 15.2.

Example 47

5-azido-4a-methyl-4,4a,5,6,7,8-hexahydronaphthalen-2(3H)-one (47)

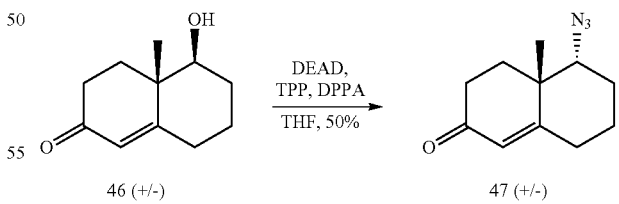

To a solution of triphenyl phosphine (0.16 g, 0.64 mmol) in THF (10 mL) was added diethyl azodicarboxylate (0.11 mL, 0.64 mmol) at 0° C. and the resulted orange solution was stirred for 10 min. Alcohol 46 (0.10 g, 0.58 mmol) in THF (3 mL) was added to the above solution. After stirring for 10 min, a solution of diphenylphosphoryl azide (0.13 mL, 0.64 mmol) was added. The reaction mixture was allowed to warm to room temperature and stirred for 10 h. The solvent was evaporated and the residue was purified by column chromatography (silica gel, EtOAc/hexanes, 2:8) to give 47 (0.059 g, 50%) as yellow liquid: $^1$H NMR (400 MHz, CDCl$_3$) δ 5.83 (d, J=1.9 Hz, 1H), 3.58 (t, J=2.8 Hz, 1H), 2.61-2.36 (m, 3H), 2.30 (ddd, J=15.4, 7.9, 5.5 Hz, 1H), 2.21-1.93 (m, 2H), 1.93-1.64 (m, 2H), 1.64-1.49 (m, 1H), 1.38-1.23 (m, 4H); $^{13}$C NMR (100 MHz, CDCl$_3$) δ 198.6, 165.5, 126.8, 68.5, 39.9, 33.8, 31.9, 31.3, 25.4, 22.3, 20.2.

Example 48

4a-methyl-5-(4-phenyl-1H-1,2,3-triazol-1-yl)-4,4a,5,6,7,8-hexahydronaphthalen-2(3H)-one (48)

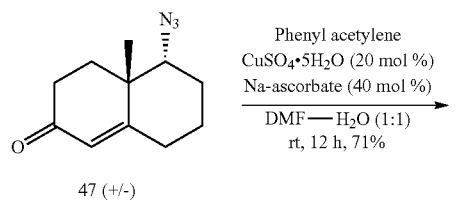

To a mixture of the azide 47 (49 mg, 0.22 mmol) and phenyl acetylene (36 mg, 0.33 mmol) in DMF (2 mL) was added sodium ascorbate (17 mg, 0.088 mmol) in H$_2$O (1 mL) and stirred for 2 min at ambient temperature. Then a CuSO$_4$.5H$_2$O (11 mg, 0.044 mmol) in H$_2$O (1 mL) was added to the above mixture. The reaction was stirred at room temperature for 12 h, quenched with water (3 mL), and extracted with EtOAc (3×5 mL). Evaporated the volatiles to give greenish residue, which was purified by flash chromatography (silica gel, EtOAc/hexanes, 4:6) to give 48 (48 mg, 71%) as white solid: mp 158-159° C. $^1$H NMR (400 MHz, CDCl$_3$) δ 7.83-7.77 (m, 2H), 7.73 (s, 1H), 7.45-7.38 (m, 2H), 7.36-7.29 (m, 1H), 5.98 (d, J=1.9 Hz, 1H), 4.84 (t, J=3.7 Hz, 1H), 2.73-2.33 (m, 4H), 2.27-2.16 (m, 1H), 2.15-1.85 (m, 2H), 1.56 (s, 3H), 1.54-1.42 (m, 2H); $^{13}$C NMR (100 MHz, CDCl$_3$) δ 197.5, 164.8, 147.5, 130.2, 128.8, 128.3, 127.1, 125.7, 119.4, 66.4, 39.8, 33.5, 30.9, 30.7, 26.8, 23.9, 20.4; HRMS (ESI) calcd for C$_{19}$H$_{22}$N$_3$O (M+H)$^+$ 308.1763. found 308.1776.

Example 49, 50, 51, 52 and 53

(S)-7a'-methyl-2',3',7',7a'-tetrahydrospiro[[1,3]dithiolane-2,5'-inden]-1'(6'H)-one (49)

(R)-7a'-methyl-1'-methylene-1',2',3',6',7',7a'-hexahydrospiro[[1,3]dithiolane-2,5'-indene] (50)

((1'S,7a'R)-7a'-methyl-1',2',3',6',7',7a'-hexahydrospiro[[1,3]dithiolane-2,5'-inden]-1'-yl)methanol (51)

(1S,7aR)-1-(hydroxymethyl)-7a-methyl-2,3,7,7a-tetrahydro-1H-inden-5(6H)-one (52)

(1S,7aR)-7a-methyl-5-oxo-2,3,5,6,7,7a-hexahydro-1H-indene-1-carbaldehyde (53)

(1S,7aR)-7a-methyl-5-oxo-2,3,5,6,7,7a-hexahydro-1H-indene-1-carbaldehyde bis amidinohydrazone (54)

Synthesis of formula III compounds of the present invention initiated from commercially available Hajos-Wiechert ketone. Compounds 49, 50, 51, 52, 53 and 54 were synthesized according to the following scheme from Sevillano et al., *J. Med. Chem.* 2002, 45, 127-136 and *Bioorg. Med. Chem.* 1999, 7, 2991-3001.

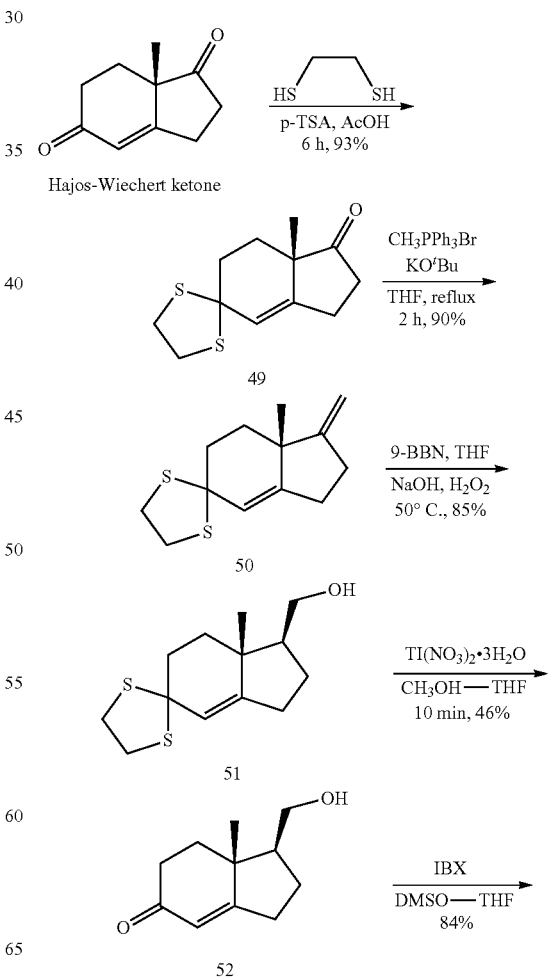

81

-continued

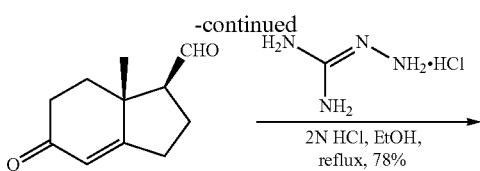

53

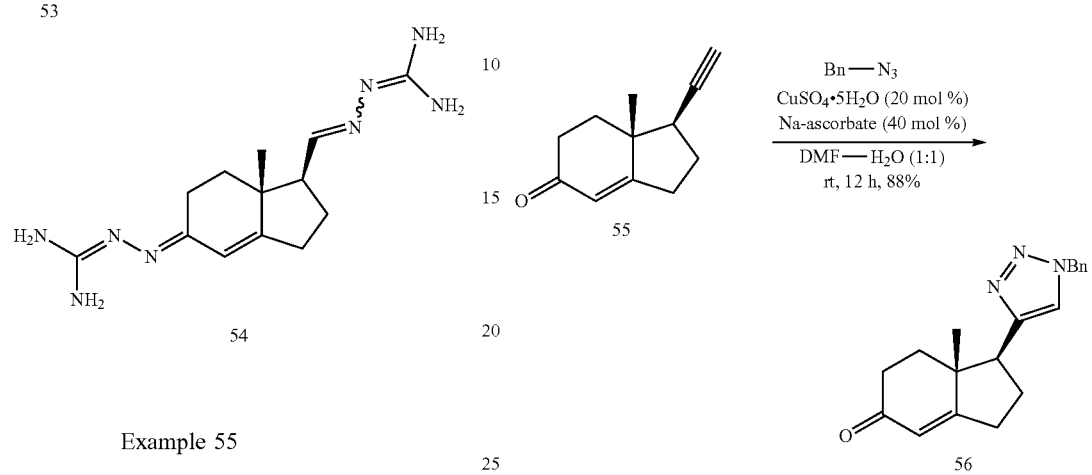

54

Example 55

(1R,7aR)-1-ethynyl-7a-methyl-2,3,7,7a-tetrahydro-1H-inden-5(6H)-one (55)

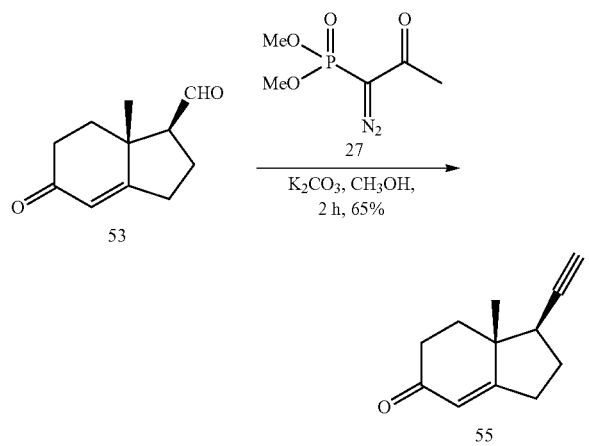

To a solution of Bestmann reagent 27 (0.13 g, 0.71 mmol) in MeOH (3 mL) was added K₂CO₃ (0.19 g, 1.43 mmol) and stirred for 10 mint at 0° C. Subsequently a solution of the aldehyde 53 (85 mg, 0.47 mmol) in MeOH (2 mL). After being stirred at room temperature for 2 h, the reaction mixture was treated with saturated aqueous NaHCO₃ and methanol was removed by evaporation. The residue was dissolved in EtOAc (30 mL) and washed with water, dried over dried over Na₂SO₄ and concentrated in vacuo to give crude residue, which was purified by column chromatography (silica gel, EtOAc/hexanes, 1:9) to get 55 (54 mg, 65%) as solid: $^1$H NMR (400 MHz, CDCl₃) δ 5.77 (s, 1H), 2.72 (dddd, J=9.0, 7.2, 5.0, 2.7 Hz, 1H), 2.59-2.33 (m, 4H), 2.23-2.11 (m, 3H), 2.04-1.89 (m, 1H), 1.78 (td, J=13.7, 5.2 Hz, 1H), 1.23 (d, J=12.4 Hz, 3H); $^{13}$C NMR (100 MHz, CDCl₃) δ 198.8, 175.3, 122.5, 82.6, 71.7, 45.3, 42.3, 34.5, 33.3, 28.7, 28.2, 17.6; HRMS (ESI) calcd for C₁₂H₁₅O (M+H)⁺ 175.1123. found 175.1128.

82

Example 56

(1S,7aR)-1-(1-benzyl-1H-1,2,3-triazol-4-yl)-7a-methyl-2,3,7,7a-tetrahydro-1H-inden-5(6H)-one (56)

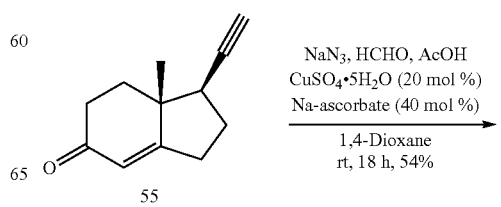

To a mixture of the benzyl azide (57 mg, 0.43 mmol) alkyne 55 (50 mg, 0.28 mmol) in DMF (2 mL) was added sodium ascorbate (22 mg, 0.11 mmol) in H₂O (1 mL) and stirred for 2 min at ambient temperature. Then a CuSO₄.5H₂O (13 mg, 0.056 mmol) in H₂O (1 mL) was added to the above mixture. The reaction was stirred at room temperature for 12 h, quenched with water (3 mL), and extracted with EtOAc (3×5 mL). Evaporated the volatiles to give greenish residue, which was purified by flash chromatography (silica gel, EtOAc/hexanes, 3:7) to give 56 (48 mg, 71%) as white solid: mp 122-125° C.; $[\alpha]_D^{26}$+71.2 (c 0.40, CHCl₃); $^1$H NMR (400 MHz, CDCl₃) δ 7.41-7.24 (m, 3H), 7.25-7.13 (m, 3H), 5.76 (d, J=10.1 Hz, 1H), 5.53-5.37 (m, 2H), 2.96 (dd, J=12.3, 7.4 Hz, 1H), 2.82-2.65 (m, 1H), 2.60-1.84 (m, 7H), 0.82 (s, 3H); $^{13}$C NMR (100 MHz, CDCl₃) δ 199.2, 177.0, 146.7, 134.6, 129.1, 128.8, 127.9, 122.4, 121.2, 54.2, 47.6, 45.5, 35.2, 33.3, 28.8, 26.0, 17.3; HRMS (ESI) calcd for C₁₉H₂₂N₃O (M+H)⁺ 308.1763. found 308.1766.

Example 57

(1S,7aR)-1-(1-(hydroxymethyl)-1H-1,2,3-triazol-4-yl)-7a-methyl-2,3,7,7a-tetrahydro-1H-inden-5(6H)-one (57a); (1S,7aR)-1-(2-(hydroxymethyl)-2H-1,2,3-triazol-4-yl)-7a-methyl-2,3,7,7a-tetrahydro-1H-inden-5(6H)-one (57b)

83
-continued

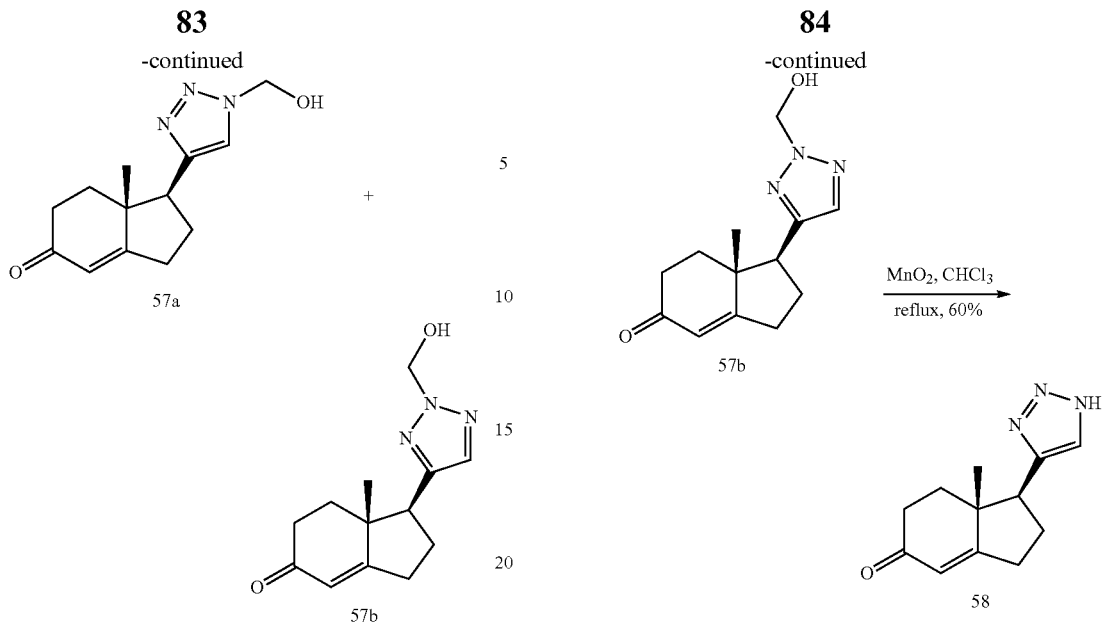

84
-continued

The mixture of HCHO (0.41 mL, 5.17 mmol, 10 equiv, 37% aq.), glacial AcOH (0.04 mL, 0.77 mmol), and 1,4-dioxane (0.41 mL) was stirred for 15 min was added NaN₃ (0.05 g, 0.77 mmol) followed by alkyne 55 (0.09 g, 0.51 mmol). After additional 10 min of stirring, sodium ascorbate (38.8 g, 0.196 mol, 20 mol %) was added, followed by CuSO₄.5H₂O. The mixture was stirred for 18 h at room temperature and extracted with CHCl₃ (3×10 mL). Combined organic layers were dried over Na₂SO₄, filtered and concentrated on a rotary evaporator to give residue 57a and 57b (0.06 g, 54%). The crude product was sufficiently pure to be used without further purification: ¹H NMR (400 MHz, CDCl₃) δ 7.59-7.41 (m, 1H), 5.94-5.64 (m, 3H), 5.05-4.64 (m, 3H), 3.45-3.31 (m, 1H), 3.01 (dd, J=12.2, 7.5 Hz, 1H), 2.84 (dd, J=19.6, 10.6 Hz, 1H), 2.71-2.55 (m, 1H), 2.56-2.13 (m, 5H), 2.12-1.83 (m, 3H), 0.90 (s, 4H); ¹³C NMR (100 MHz, CDCl₃) δ 199.2, 177.0, 147.6, 134.0, 122.4, 67.0, 47.6, 45.5, 35.1, 33.2, 28.8, 25.7, 17.3.

The mixture of 57a and 57b (65 mg, 0.26 mmol) and active MnO₂ (220 mg, 2.63 mmol) in CHCl₃ (10 mL) was stirred under reflux for 20 h. Then reaction was filtered through celite, washed with CHCl₃: MeOH (1:1, 20 mL) and the solvents were removed under reduced pressure. The residue was purified by column chromatography (silica gel, acetone/hexanes, 3:7) to get 58 (34 mg, 60%) as white solid: mp 126-129° C.; [α]$_D^{26}$+2.25 (c 0.31, CHCl₃); ¹H NMR (400 MHz, CDCl₃) δ 7.59 (d, J=14.0 Hz, 1H), 5.97-5.77 (m, 1H), 3.18-2.99 (m, 1H), 2.96-2.74 (m, 1H), 2.77-1.91 (m, 8H), 1.00-0.69 (m, 4H); ¹³C NMR (100 MHz, CDCl₃) δ 199.6, 177.5, 122.4, 47.4, 45.6, 35.1, 33.3, 28.9, 25.9, 17.3; HRMS (ESI) calcd for C₁₂H₁₆N₃O (M+H)⁺ 218.1293. found 218.1279.

Formula IV compounds of the present invention were synthesized from commercially available pregnenolone and dehydro-epi-androsterone.

Example 58

(1S,7aR)-7a-methyl-1-(2H-1,2,3-triazol-4-yl)-2,3,7,7a-tetrahydro-1H-inden-5(6H)-one (58)

Example 59

1-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)ethanone (59)

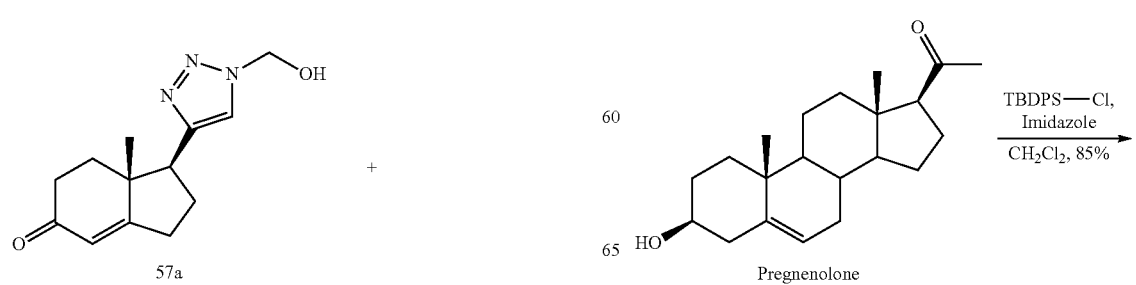

-continued

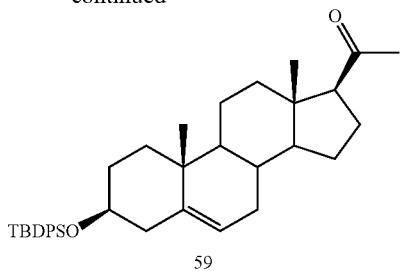

59

To a solution of pregnenolone (4.00 g, 12.65 mmol) in CH$_2$Cl$_2$ (100 mL) at 0° C. were added imidazole (2.58 g, 37.97 mmol) and TBDPSCl (4.80 mL, 18.98 mmol). After being stirred at ambient temperature for 4 h, the reaction mixture was quenched with saturated aqueous NaHCO$_3$ (60 mL). The organic phase was separated and extracted with an additional CH$_2$Cl$_2$ (2×100 mL). The combined organic layers were dried over Na$_2$SO$_4$ and concentrated in vacuo to give residue, which was purified by column chromatography (silica gel, EtOAc/hexanes, 1:9) to get TBDPS-ether 59 (5.96 g, 85%) as white solid: $^1$H NMR (400 MHz, CDCl$_3$) δ 7.71-7.66 (m, 4H), 7.46-7.32 (m, 6H), 5.17-5.09 (m, 1H), 3.66-3.42 (m, 1H), 2.59-2.44 (m, 1H), 2.43-2.26 (m, 1H), 2.22-2.08 (m, 5H), 2.07-1.85 (m, 2H), 1.80-1.32 (m, 10H), 1.31-1.15 (m, 1H), 1.14-1.03 (m, 10H), 0.99 (s, 3H), 0.87 (ddd, J=13.9, 6.6, 3.6 Hz, 2H), 0.61 (s, 3H); $^{13}$C NMR (100 MHz, CDCl$_3$) δ 209.5, 141.2, 135.78, 135.77, 134.8, 134.7, 129.46, 129.43, 127.47, 127.45, 120.8, 73.1, 63.7, 56.9, 49.9, 43.9, 42.4, 38.8, 37.2, 36.5, 31.8, 31.7, 31.5, 27.0, 24.7, 22.8, 21.0, 19.1, 19.1, 13.2.

Example 60

2-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)-2-oxoethyl acetate (60)

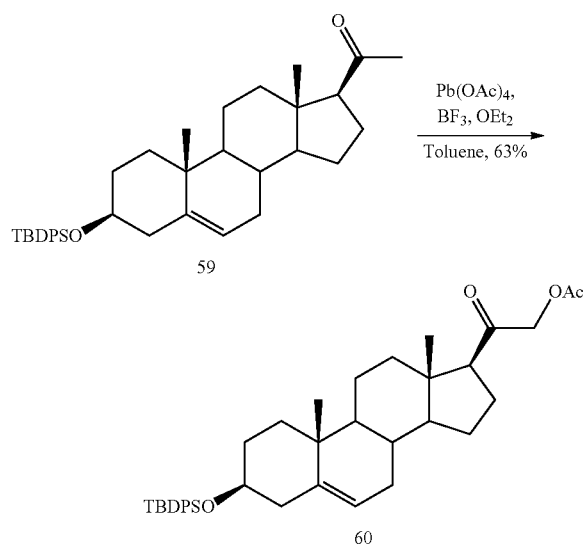

To a stirred solution of compound 59 (1.00 g, 1.80 mmol) in toluene (28 mL), methanol (3.40 mL) containing of BF$_3$.OEt$_2$ (3.37 mL, 27.00 mmol) was added lead tetraacetate (0.87 g, 1.98 mmol) at room temperature. After being stirred at room temperature for 4 h, the mixture was poured into ice water and extracted with CH$_2$Cl$_2$ (3×30 mL). Purification on column chromatography (silica gel, EtOAc/hexanes, 15:85) gave compound 60 (0.69 g, 63%) as white powder: $^1$H NMR (400 MHz, CDCl$_3$) δ 7.75-7.61 (m, 4H), 7.50-7.29 (m, 6H), 5.12 (d, J=5.1 Hz, 1H), 4.70 (dd, J=16.9, 6.6 Hz, 1H), 4.51 (dd, J=16.8, 5.9 Hz, 1H), 3.63-3.44 (m, 1H), 2.55-2.25 (m, 2H), 2.24-2.08 (m, 5H), 2.07-1.81 (m, 2H), 1.80-1.17 (m, 12H), 1.15-0.92 (m, 12H), 0.85 (ddd, J=22.5, 14.4, 8.3 Hz, 2H), 0.68-0.61 (m, 3H); $^{13}$C NMR (100 MHz, CDCl$_3$) δ 203.8, 170.2, 141.3, 135.7, 135.6, 134.79, 134.76, 129.45, 129.43, 127.46, 127.44, 120.7, 73.1, 69.1, 59.29, 59.22, 57.0, 49.8, 44.6, 42.4, 38.5, 37.1, 36.5, 31.82, 31.73, 26.9, 24.5, 22.8, 20.9, 20.4, 19.3, 19.1, 13.0.

Example 61

1-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)ethane-1,2-diol (61)

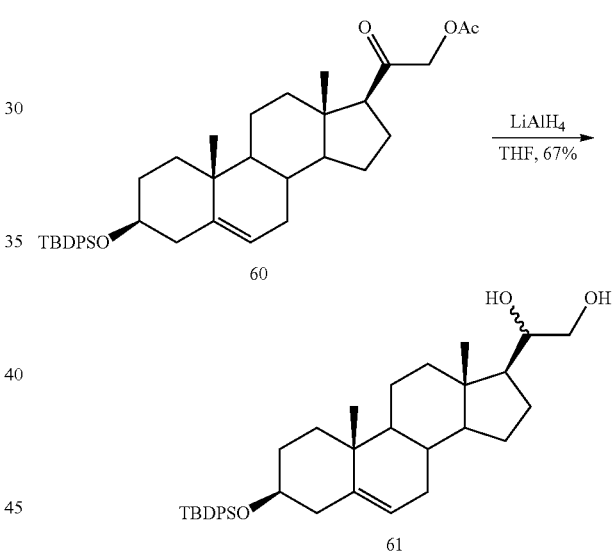

A 100-mL, two-necked, round-bottomed flask was charged with LiAlH$_4$ (0.86 g, 22.74 mmol) under nitrogen and cooled to 0° C. Anhydrous THF (40 mL) followed by the compound 60 (3.48 g, 5.68 mmol) in THF (10 mL) was added dropwise and the resulting mixture was stirred at ambient temperature for 30 min. The reaction mixture was quenched with H$_2$O (0.9 mL), 15% of NaOH solution (0.9 mL) and H$_2$O (2.7 mL), and stirred for another 10 min. The precipitate was filtered and washed with Et$_2$O, the filtrate was dried over Na$_2$SO$_4$ and concentrated in vacuo and the residue was purified by column chromatography (silica gel, EtOAc/hexanes, 3:7) to get 61(2.17 g, 67%) as white foam: $^1$H NMR (400 MHz, CDCl$_3$) δ 7.72-7.63 (m, 4H), 7.47-7.31 (m, 6H), 5.12 (d, J=5.0 Hz, 1H), 3.64 (d, J=9.3 Hz, 2H), 3.60-3.46 (m, 1H), 3.36 (t, J=9.2 Hz, 1H), 2.33 (t, J=12.2 Hz, 1H), 2.22-1.98 (m, 2H), 1.99-1.79 (m, 3H), 1.77-1.53 (m, 6H), 1.52-1.33 (m, 5H), 1.31-1.10 (m, 3H), 1.05 (s, 9H), 0.99 (s, 3H), 0.92-0.78 (m, 2H), 0.76 (s, 3H); $^{13}$C NMR (100 MHz, CDCl$_3$) δ 141.3, 135.77, 135.76, 134.81, 134.80, 129.43, 129.41, 127.45, 127.43, 120.8, 74.6, 73.2, 66.4, 55.9, 52.4, 50.0, 42.47, 42.40, 39.7, 37.2, 36.5, 31.87, 31.84, 31.7, 26.9, 24.6, 24.5, 20.8, 19.4, 19.1, 12.3.

Example 62 tert-butyl(((3S,10R,13S,17R)-17-ethynyl-10,13-dimethyl-2,3,4,7,8,9,10,11,12,13,14,15,16,17-tetradecahydro-1H-cyclopenta[a]phenanthren-3-yl)oxy)diphenylsilane (62)

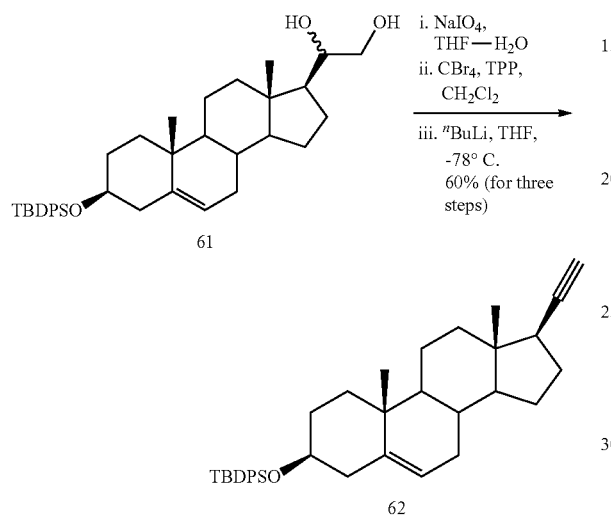

Sodium periodate (0.55 g, 2.62 mmol) was added to a solution of diol 61 (0.50 g, 0.87 mmol) in THF:H$_2$O (8:2, 20 mL) and the solution was stirred for 1 h. The reaction mixture was then diluted with water (20 mL), organic phase was separated and extracted with ethyl acetate (3×30 mL). The combined organic layers were dried over Na$_2$SO$_4$, filtered and concentrated in vacuo. The residue was purified by column chromatography (silica gel, EtOAc/hexanes, 3:7) to afford the aldehyde (0.50 g), which was used for the next step without further purification.

To a solution of tetrabromomethane (0.91 g, 2.77 mmol) in anhydrous dichloromethane (20 mL) was added triphenylphosphine (1.45 g, 5.55 mmol) at 0° C., and the resulting mixture was stirred for 10 min. Subsequently, a solution of the above aldehyde (0.50 g, 0.92 mmol) in dichloromethane (5 mL) was added. After stirring for 20 min, the reaction mixture was diluted with dichloromethane (30 mL) and the organic phase was washed with water (30 mL) and saturated NaCl solution (30 mL) and dried over Na$_2$SO$_4$, concentrated in vacuo to give dibromoalkene (0.70 g), which was also used for the next step without further purification.

A solution of n-BuLi (1.6 M) in hexane (2.51 mL, 4.02 mmol) was added to a solution of dibromoalkene (0.70 g, 1.0 mmol) in anhydrous THF (20 mL) at −78° C., and the resulting mixture was stirred at the same temperature for 1 h. The reaction mixture was quenched with saturated aqueous NH$_4$Cl (20 mL), the mixture was extracted with ethyl acetate (3×20 mL), dried over Na$_2$SO$_4$, and then concentrated in vacuo. The obtained residue was purified by column chromatography (silica gel, hexanes/EtOAc, 1:9) to afford the alkyne 62 (0.33 g, 60%) as white solid: $^1$H NMR (400 MHz, CDCl$_3$) δ 7.76-7.61 (m, 4H), 7.51-7.28 (m, 6H), 5.12 (d, J=5.2 Hz, 1H), 3.69-3.42 (m, 1H), 2.35 (dt, J=13.2, 11.3 Hz, 1H), 2.21-1.78 (m, 5H), 1.79-1.33 (m, 10H), 1.35-1.12 (m, 1H), 1.06 (s, 9H), 1.03 (d, J=4.5 Hz, 1H), 1.00 (s, 3H), 0.86 (m, 3H), 0.79 (s, 3H); $^{13}$C NMR (100 MHz, CDCl$_3$) δ 141.3, 135.78, 135.76, 134.8, 134.7, 129.45, 129.43, 127.46, 127.44, 120.8, 85.9, 73.1, 69.1, 54.9, 50.0, 43.6, 42.4, 41.8, 37.2, 37.1, 36.5, 32.3, 31.8, 29.0, 27.0, 24.6, 20.8, 19.45, 19.13, 13.3.

Example 63

1-benzyl-4-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)-1H-1,2,3-triazole (63)

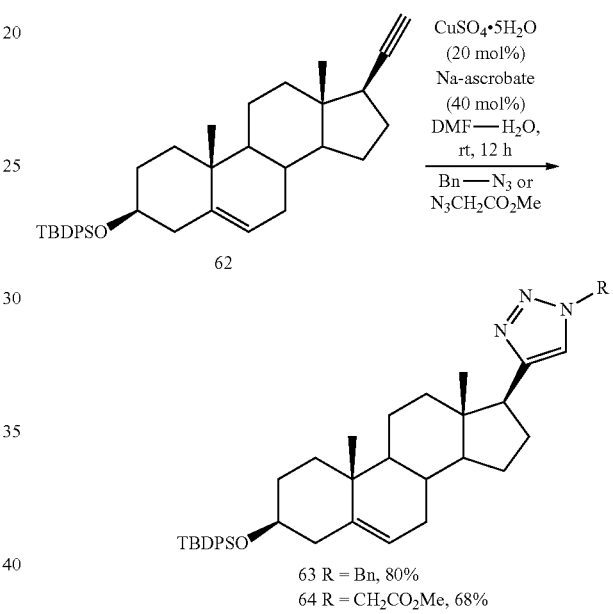

63 R = Bn, 80%
64 R = CH$_2$CO$_2$Me, 68%

General Procedure:

A mixture of the alkyne 62 (1 eq), azide (1.5 eq) and in DMF (6 mL) was added sodium ascorbate (0.4 eq) in H$_2$O (3 mL) and stirred for two minutes at ambient temperature. Then a CuSO$_4$.5H$_2$O (0.2 eq) in H$_2$O (3 mL) was added to the above mixture. The mixture was stirred at room temperature for 12 h, water was added (6 mL), and extracted with EtOAc (3×10 mL). The volatiles were evaporated and then purified by flash chromatography (silica gel, hexanes/ethyl acetate, 2:8) to give triazole compound.

Compound 63, yield (0.29 g, 80%) as white foam: $^1$H NMR (400 MHz, CDCl$_3$) δ 7.65-7.54 (m, 4H), 7.40-7.22 (m, 9H), 7.18-7.12 (m, 2H), 7.10 (s, 1H), 5.49-5.35 (m, 2H), 5.06 (d, J=5.0 Hz, 1H), 3.53-3.36 (m, 1H), 2.67 (t, J=9.8 Hz, 1H), 2.35-2.17 (m, 1H), 2.12-1.79 (m, 4H), 1.74-0.99 (m, 12H), 0.98 (s, 9H), 0.88 (d, J=13.9 Hz, 3H), 0.85-0.71 (m, 2H), 0.36 (s, 3H); $^{13}$C NMR (100 MHz, CDCl$_3$) δ 149.4, 141.3, 135.82, 135.80, 135.12, 134.6, 129.53, 129.52, 129.0, 128.5, 127.8, 127.54, 127.52, 121.0, 120.9, 73.1, 55.9, 53.9, 50.0, 47.8, 43.5, 42.4, 37.5, 37.1, 36.5, 32.2, 31.8, 27.0, 26.6, 24.5, 20.6, 19.53, 19.19, 13.0. HRMS (ESI) calcd for C$_{44}$H$_{56}$N$_3$OSi (M+H)$^+$ 670.4193. found 670.4189.

Example 64

Methyl 2-(4-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)-1H-1,2,3-triazol-1-yl)acetate (64)

Compound 64 (0.33 g, 68% yield) as white foam: $^1$H NMR (400 MHz, CDCl$_3$) δ 7.72-7.62 (m, 4H), 7.46-7.31 (m, 7H), 5.18-5.09 (m, 3H), 3.79 (s, 3H), 3.64-3.46 (m, 1H), 2.80 (t, J=9.8 Hz, 1H), 2.33 (td, J=13.5, 6.9 Hz, 1H), 2.21-1.89 (m, 4H), 1.86-1.09 (m, 12H), 1.05 (d, J=4.7 Hz, 9H), 1.00-0.96 (m, 3H), 0.95-0.80 (m, 2H), 0.49 (s, 3H); $^{13}$C NMR (100 MHz, CDCl$_3$) δ 167.0, 149.3, 141.4, 135.77, 135.76, 134.8, 129.44, 129.43, 127.46, 127.44, 122.2, 120.9, 73.2, 56.0, 52.9, 50.5, 50.1, 47.8, 43.5, 42.4, 37.6, 37.2, 36.6, 32.2, 31.87, 31.85, 27.0, 26.6, 24.5, 20.6, 19.4, 19.1, 12.9; HRMS (ESI) calcd for C$_{40}$H$_{54}$N$_3$O$_3$Si (M+H)$^+$ 652.3934. found 652.3919.

Example 65

4-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)-1H-1,2,3-triazole (65)

The mixture of HCHO (0.60 mL, 7.46 mmol, 37% aq), glacial AcOH (64 µL, 1.19 mol), and 1,4-dioxane (0.60 mL) was stirred for 15 min, then NaN$_3$ (72 mg, 1.5 mmol), followed by alkyne 62 (0.40 g, 0.74 mmol) were added to the reaction. After additional 10 minutes of stirring, sodium ascorbate (59 mg, 0.029 mol) and CuSO$_4$.5H$_2$O (37 mg, 0.014 mmol) were added. The mixture was stirred for 18 h at room temperature, then diluted with H$_2$O (20 mL) and extracted with CHCl$_3$ (3×20 mL), dried over Na$_2$SO$_4$, filtered, and concentrated on a rotary evaporator to give residue, which was used for the next step without further purification. The above product (0.22 g, 0.37 mmol), and active MnO$_2$ (0.32 g, 3.70 mmol) in CHCl$_3$ (20 mL) was stirred under reflux for 20 h. Then reaction was filtered through Celite, washed with CHCl$_3$:MeOH, 1:1 and the solvent was removed under reduced pressure. The residue was purified by column chromatography to get 65 (0.17 g, 82%) as white foam: $^1$H NMR (400 MHz, CDCl$_3$) δ 7.72-7.64 (m, 4H), 7.50 (s, 1H), 7.45-7.32 (m, 6H), 5.14 (d, J=5.2 Hz, 1H), 3.64-3.45 (m, 1H), 2.77 (t, J=9.8 Hz, 1H), 2.33 (td, J=13.4, 6.8 Hz, 1H), 2.23-1.87 (m, 4H), 1.86-1.10 (m, 13H), 1.06 (d, J=5.7 Hz, 9H), 1.01-0.96 (m, 3H), 0.95-0.80 (m, 2H), 0.49 (s, 3H); $^{13}$C NMR (100 MHz, CDCl$_3$) δ 141.3, 135.78, 135.77, 134.7, 129.46, 129.44, 127.47, 127.45, 120.8, 73.1, 56.0, 50.1, 47.3, 43.7, 42.4, 37.5, 37.2, 36.5, 32.2, 31.8, 27.0, 26.4, 24.5, 20.6, 19.4, 19.1, 12.9; HRMS (ESI) calcd for C$_{37}$H$_{50}$N$_3$OSi (M+H)$^+$ 580.3723. found 580.3740.

Example 66

(3S,10R,13S,17S)-17-(1-benzyl-1H-1,2,3-triazol-4-yl)-10,13-dimethyl-2,3,4,7,8,9,10,11,12,13,14,15,16,17-tetradecahydro-1H-cyclopenta[a]phenanthren-3-ol (66)

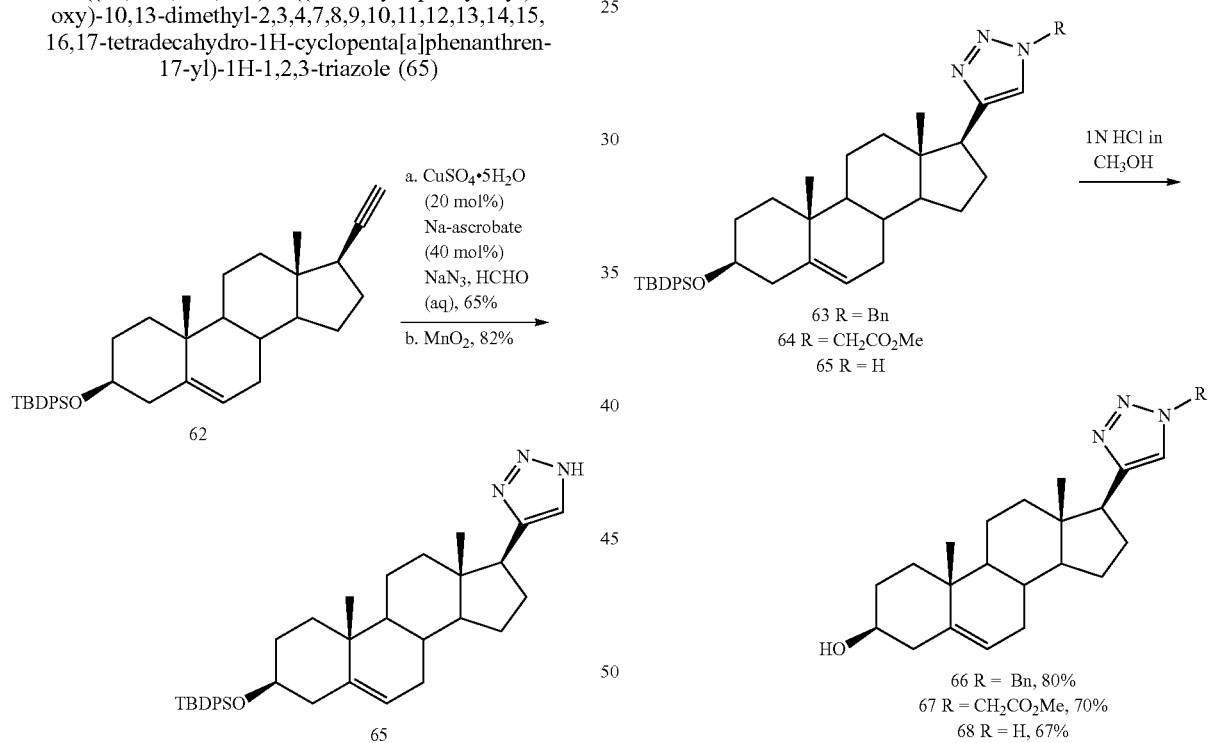

Silylated triazole 63 (0.08 g, 0.11 mmol) was dissolved in 1N HCl in MeOH (4:3 mL) and the solution stirred for 5 h at room temperature. The reaction mixture was concentrated in vacuo. The residue was purified by column chromatography (acetone/hexanes, 4:6) to give 66 (41 mg, 80%) as white solid: mp 286-287° C.; [α]$_D^{26}$-9.41 (c 1.55, CHCl$_3$:MeOH (3:1); $^1$H NMR (400 MHz, CDCl$_3$+CD$_3$OD) δ 7.98-7.87 (m, 4H), 7.80 (dd, J=7.6, 1.7 Hz, 2H), 6.08 (s, 2H), 5.91 (d, J=5.1 Hz, 1H), 4.10-3.95 (m, 1H), 3.33 (t, J=9.8 Hz, 1H), 2.92-2.71 (m, 2H), 2.70-2.46 (m, 3H), 2.47-2.24 (m, 4H), 2.23-1.61 (m, 10H), 1.54 (s, J=9.4 Hz, 3H), 1.04 (s, 3H); $^{13}$C NMR (100 MHz, CDCl$_3$+CD$_3$OD) δ 153.0, 144.8, 138.7, 132.9, 132.5, 131.6, 125.3, 125.1, 75.0, 59.8, 57.8, 54.1, 47.3, 45.6, 41.38, 41.15, 40.4, 36.2, 35.6, 34.9, 30.5, 28.3, 24.5, 23.1, 16.6; HRMS (ESI) calcd for C$_{28}$H$_{38}$N$_3$O (M+H)$^+$ 432.3015. found 432.3018.

Example 67 methyl 2-(4-((3S,10R,13S,17S)-3-hydroxy-10,13-dimethyl-2,3,4,7,8,9,10,11,12,13,14,15,16,17-tetradecahydro-1H-cyclopenta[a]phenanthren-17-yl)-1H-1,2,3-triazol-1-yl)acetate (67)

Followed the procedure described for 66 to get 67 (0.026 g, 70%) as white solid: mp 221-223° C.; [α]$_D^{26}$ −15.68 (c 0.38, CHCl$_3$: MeOH (3:1)); $^1$H NMR (400 MHz, CDCl$_3$) δ 8.03 (s, 1H), 5.92 (s, 1H), 5.73 (s, 2H), 4.37 (s, 3H), 3.38 (t, J=9.8 Hz, 1H), 2.91-2.72 (m, 2H), 2.62 (dd, J=22.9, 11.8 Hz, 3H), 2.39 (dd, J=16.9, 12.1 Hz, 4H), 2.25-1.72 (m, 10H), 1.71-1.32 (m, 6H), 1.08 (s, 3H); $^{13}$C NMR (100 MHz, CDCl$_3$) δ 167.0, 149.1, 140.8, 122.6, 121.2, 71.2, 55.9, 52.8, 50.54, 50.16, 47.6, 43.5, 41.8, 37.44, 37.18, 36.5, 32.2, 31.7, 31.1, 29.5, 26.6, 24.4, 20.6, 19.2, 12.7; HRMS (ESI) calcd for C$_{24}$H$_{36}$N$_3$O$_3$(M+H)$^+$ 414.2757. found 414.2767.

Example 68

(3S,10R,13S,17S)-10,13-dimethyl-17-(1H-1,2,3-triazol-4-yl)-2,3,4,7,8,9,10,11,12,13,14,15,16,17-tetradecahydro-1H-cyclopenta[a]phenanthren-3-ol (68)

Compound 68 (0.07 g, 0.12 mmol), yield (0.027 g, 67%) as white solid: mp. 275-277° C. $^1$H NMR (400 MHz, CDCl$_3$) δ 8.36 (s, 1H), 6.39-6.23 (m, 1H), 3.76 (t, J=9.8 Hz, 1H), 3.38-3.11 (m, 2H), 3.10-2.92 (m, 3H), 2.89-2.65 (m, 4H), 2.67-2.11 (m, 12H), 2.12-1.61 (m, 6H), 1.48 (s, 3H); HRMS (ESI) calcd for C$_{21}$H$_{32}$N$_3$O (M+H)$^+$ 342.2545. found 342.2553.

Example 69

(3S,10R,13S)-3-((tert-butyldiphenylsilyl)oxy)-10,13-dimethyl-3,4,7,8,9,10,11,12,13,14,15,16-dodecahydro-1H-cyclopenta[a]phenanthren-17(2H)-one (69)

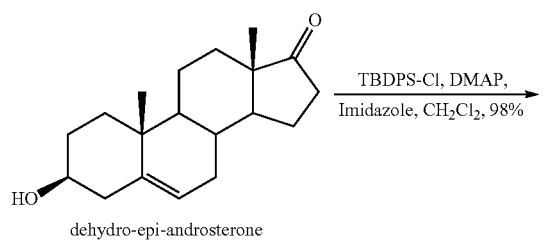

To a solution of dehydro-epi-androsterone (3.00 g, 10.41 mmol) in CH$_2$Cl$_2$ (75 mL) at 0° C. were added imidazole (1.41 g, 20.83 mmol) and TBDPSCl (2.92 mL, 11.45 mmol). After being stirred at ambient temperature for 5 h, the reaction mixture was quenched with saturated aqueous NaHCO$_3$ (50 mL) and extracted with CH$_2$Cl$_2$ (2×75 mL). The combined organic layers were dried over Na$_2$SO$_4$ and concentrated in vacuo to give residue, which was purified by column chromatography (silica gel, EtOAc/hexanes, 1:9) to give compound 69 (5.36 g, 98%) as a white solid. Analytical data was in agreement with that reported by Calogeropoulou et al., *J. Med. Chem.* 2009, 52, 6569-6587.

Example 70

(3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-ol (70)

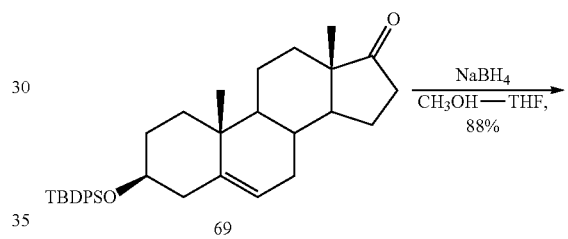

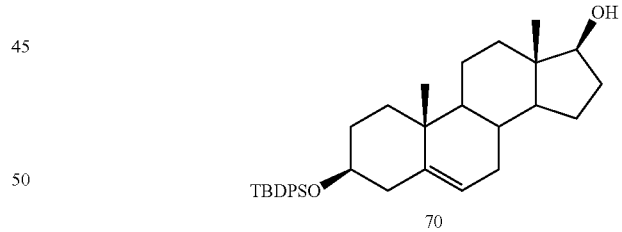

To a solution of ketone 69 (1.70 g, 3.23 mmol) in MeOH:THF (30 mL, 1:1) was added NaBH$_4$ (0.36 g, 9.69 mmol) at 0° C. After stirred for 1 h, the reaction mixture was quenched by addition of saturated aqueous NH$_4$Cl (50 mL). The mixture was extracted with EtOAc (3×50 mL), washed with brine (50 mL), dried over Na$_2$SO$_4$. The volatiles were evaporated and purified by flash chromatography (silica gel, EtOAc/hexane 2:8) to afford the alcohol 70 (1.50 g, 88%) as white solid: Analytical data was in agreement with that reported by Calogeropoulou et al., *J. Med. Chem.* 2009, 52, 6569-6587.

Example 71

(((3S,10R,13S,17R)-17-azido-10,13-dimethyl-2,3,4,7,8,9,10,11,12,13,14,15,16,17-tetradecahydro-1H-cyclopenta[a]phenanthren-3-yl)oxy)(tert-butyl)diphenylsilane (71)

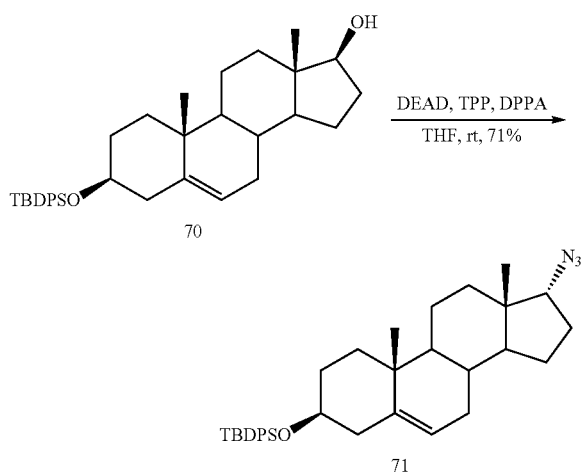

To a solution of triphenyl phosphine (1.09 g, 4.18 mmol) in THF (30 mL) was added diethyl azodicarboxylate (2.20 mL, 4.82 mmol, 40% solution in toluene) at 0° C. and the resulted orange solution was stirred for 10 min. Alcohol 70 (1.70 g, 3.21 mmol) in THF (10 mL) was added to the above solution. After stirring for 10 min, a solution of diphenylphosphoryl azide (1.18 g, 4.82 mmol) was added. The reaction mixture was allowed to warm to room temperature and stirred for 10 h. The solvent was evaporated and the residue was purified by column chromatography (silica gel, EtOAc/hexanes, 1:9) to yield 71 (1.26 g, 71%) as viscous oil: $^1$H NMR (400 MHz, CDCl$_3$) δ 7.77-7.59 (m, 4H), 7.48-7.29 (m, 6H), 5.18-5.05 (m, 1H), 3.53 (ddd, J=16.4, 10.5, 5.4 Hz, 2H), 2.44-2.23 (m, 1H), 2.24-2.04 (m, 2H), 2.03-1.84 (m, 1H), 1.81-1.29 (m, 13H), 1.28-1.12 (m, 2H), 1.06 (s, 9H), 0.98 (s, 3H), 0.92-0.81 (m, 2H), 0.73 (s, 3H); $^{13}$C NMR (100 MHz, CDCl$_3$) δ 141.2, 135.77, 135.76, 134.7, 129.45, 129.44, 127.47, 127.44, 120.8, 73.1, 71.4, 49.8, 49.6, 45.6, 42.4, 37.2, 36.5, 32.4, 32.1, 32.0, 31.8, 28.6, 27.0, 24.7, 20.5, 19.4, 19.1, 17.4.

Example 72

1-((3S,10R,13S,17R)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)-4-phenyl-1H-1,2,3-triazole (72)

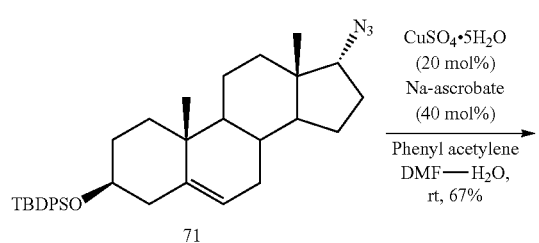

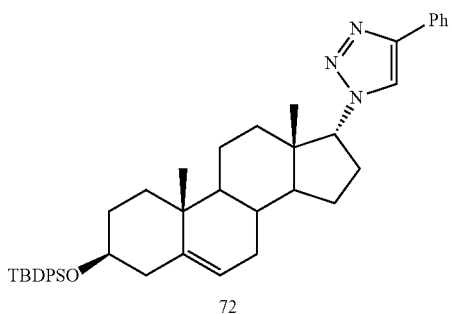

A mixture of the azide 71 (0.90 g, 1.62 mmol) and phenyl acetylene (0.33 g, 3.25 mmol) in DMF (12 mL) was added sodium ascorbate (128 mg, 0.64 mmol) in H$_2$O (6 mL) and stirred for two minutes at ambient temperature. Then a CuSO$_4$.5H$_2$O (80 mg, 0.32 mmol) in H$_2$O (6 mL) was added to the above mixture. The mixture was stirred at room temperature for 12 h, water was added (20 mL), and extracted with EtOAc (3×20 mL). Evaporation of combined organic extracts afforded a green solid, which was purified by flash chromatography (hexanes/ethyl acetate, 2:8) to give compound 72 (0.71 g, 67%) as solid: $^1$H NMR (400 MHz, CDCl$_3$) δ 7.82 (dd, J=8.2, 1.2 Hz, 2H), 7.69-7.60 (m, 5H), 7.47-7.28 (m, 9H), 5.21-5.04 (m, 1H), 4.62 (dt, J=14.0, 7.0 Hz, 1H), 3.61-3.35 (m, 1H), 2.66-2.41 (m, 1H), 2.26 (tt, J=22.9, 11.6 Hz, 2H), 2.19-1.91 (m, 3H), 1.74-1.31 (m, 11H), 1.12-0.99 (m, 9H), 0.97 (s, 3H), 0.95 (s, 3H), 0.83-0.62 (m, 2H); $^{13}$C NMR (100 MHz, CDCl$_3$) δ 146.9, 141.2, 135.74, 135.72, 134.74, 134.73, 129.45, 129.43, 128.7, 127.9, 127.46, 127.43, 125.6, 120.6, 119.5, 73.1, 70.3, 50.2, 49.3, 46.1, 42.4, 37.0, 36.4, 32.45, 32.16, 31.94, 31.76, 28.6, 26.9, 25.3, 20.3, 19.3, 19.1, 18.3; HRMS (ESI) calcd for C$_{43}$H$_{54}$N$_3$OSi (M+H)$^+$ 656.4036. found 656.4038.

Example 73

(3S,10R,13S,17R)-10,13-dimethyl-17-(4-phenyl-1H-1,2,3-triazol-1-yl)-2,3,4,7,8,9,10,11,12,13,14,15,16,17-tetradecahydro-1H-cyclopenta[a]phenanthren-3-ol (73)

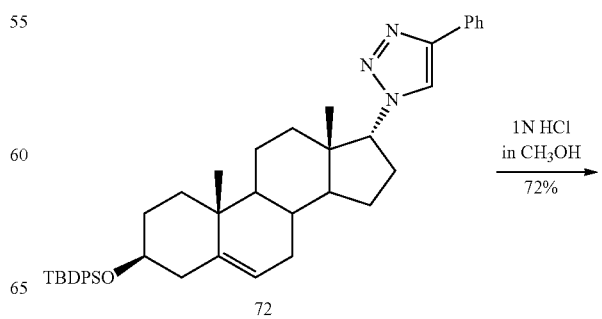

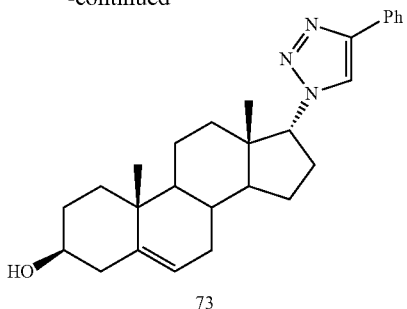

73

The silylated triazole 72 (0.50 g, 0.76 mmol) was dissolved in 1N HCl in MeOH (10 mL) and the solution stirred for 5 h at room temperature. The reaction mixture was concentrated. The residue was purified by column chromatography (silica gel, acetone/hexanes, 4:6) to give 73 (0.22 g, 72%) as a white solid: mp 234-236° C.; $[\alpha]_D^{26}$ −25.36 (c 0.40, CHCl$_3$); $^1$H NMR (400 MHz, CDCl$_3$) δ 7.84 (d, J=7.2 Hz, 2H), 7.67 (s, 1H), 7.42 (t, J=7.6 Hz, 2H), 7.32 (t, J=7.4 Hz, 1H), 5.43-5.28 (m, 1H), 4.64 (dd, J=8.5, 1.6 Hz, 1H), 3.60-3.37 (m, 1H), 2.55 (ddd, J=18.7, 10.8, 2.5 Hz, 1H), 2.43-1.97 (m, 5H), 1.87-1.33 (m, 13H), 1.08-0.77 (m, 8H), 0.46-0.22 (m, 1H); $^{13}$C NMR (100 MHz, CDCl$_3$) δ 146.9, 140.7, 130.7, 128.8, 128.0, 125.6, 121.2, 119.7, 71.6, 70.3, 50.2, 49.4, 46.1, 42.1, 37.1, 36.4, 32.4, 32.2, 31.9, 31.5, 28.6, 25.3, 20.4, 19.3, 18.4; HRMS (ESI) calcd for C$_{27}$H$_{36}$N$_3$O (M+H)$^+$ 418.2858. found 418.2842.

Example 74

1-((3R,10R,13S,17R)-3-azido-10,13-dimethyl-2,3,4,7,8,9,10,11,12,13,14,15,16,17-tetradecahydro-1H-cyclopenta[a]phenanthren-17-yl)-4-phenyl-1H-1,2,3-triazole (74)

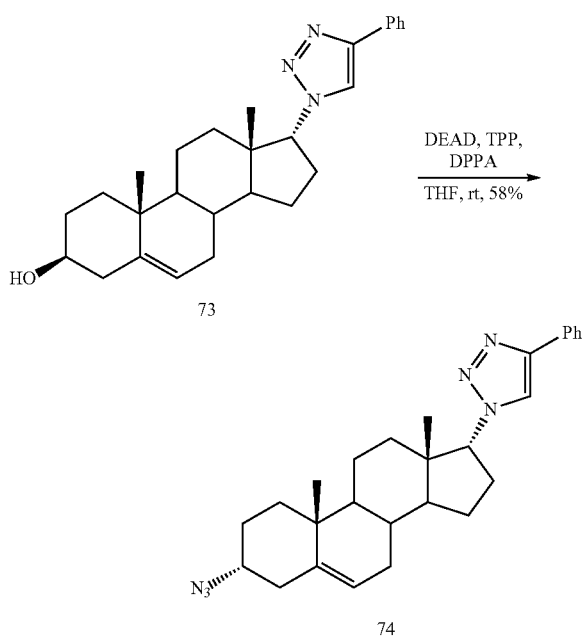

To a solution of triphenyl phosphine (0.16 g, 0.62 mmol) in THF (10 mL) was added diethyl azodicarboxylate (0.12 g, 0.71 mmol, 40% solution in toluene) at 0° C. and the resulted orange solution was stirred for 10 min. Alcohol 73 (0.20 g, 0.47 mmol) in THF (3 mL) was added to the above solution. After stirring for 10 min, a solution of diphenylphosphoryl azide (0.22 mL, 0.81 mmol) was added. The reaction mixture was allowed to warm to room temperature and stirred for 10 h. The solvent was evaporated and the residue was purified by column chromatography (silica gel, acetone/hexanes, 3:7) to give 74 (0.12 g, 58%) as yellow foam: $^1$H NMR (400 MHz, CDCl$_3$) δ 7.89-7.79 (m, 2H), 7.67 (d, J=5.7 Hz, 1H), 7.42 (t, J=7.6 Hz, 2H), 7.32 (t, J=7.4 Hz, 1H), 5.39 (dd, J=13.5, 11.0 Hz, 1H), 4.69 (dd, J=8.6, 1.8 Hz, 1H), 3.88-3.80 (m, 1H), 2.72-2.39 (m, 2H), 2.41-1.97 (m, 4H), 1.90-1.21 (m, 12H), 1.08-0.90 (m, 6H), 0.45-0.21 (m, 1H); $^{13}$C NMR (100 MHz, CDCl$_3$) δ 147.0, 138.0, 128.7, 128.0, 125.66, 125.62, 122.6, 119.3, 70.2, 57.9, 50.3, 49.2, 46.0, 37.0, 35.9, 33.4, 32.4, 32.0, 31.9, 28.7, 26.0, 25.2, 20.0, 18.9, 18.3; HRMS (ESI) calcd for C$_{27}$H$_{35}$N$_6$ (M+H)$^+$ 443.2923. found 443.2911.

Example 75

4-((3R,10R,13S,17R)-10,13-dimethyl-17-(4-phenyl-1H-1,2,3-triazol-1-yl)-2,3,4,7,8,9,10,11,12,13,14,15,16,17-tetradecahydro-1H-cyclopenta[a]phenanthren-3-yl)morpholine (75)

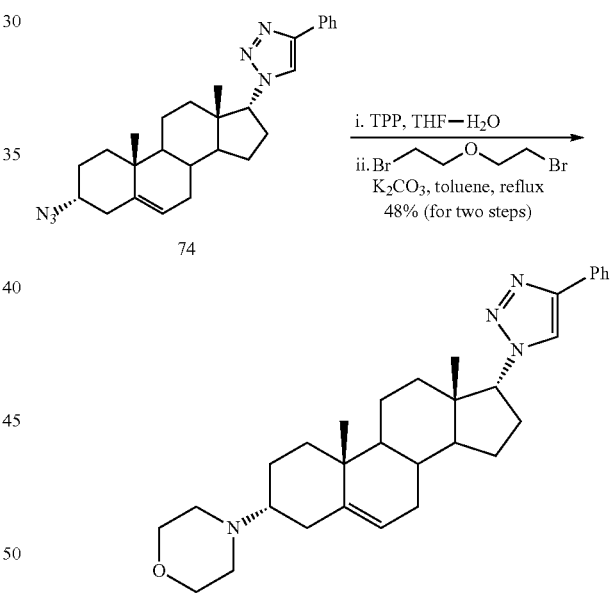

To a solution of azide 74 (0.13 g, 0.30 mmol) in THF was added triphenyl phosphine (0.10 g, 0.39 mmol) at ambient temperature. After stirred for 1 h, the reaction mixture was diluted with water and stirred at room temperature for 10 h. The solvent was evaporated to give corresponding amine, which was used for the next step without purification.

To a solution of crude amine (0.13 g, 0.32 mmol) in toluene (10 mL) was added 2-bromoethyl ether (0.11 g, 0.48 mmol) and K$_2$CO$_3$ (0.050 g, 0.64 mmol). The reaction mixture was refluxed under for 24 h. After cooling, the reaction mixture was filtered and concentrated. The residue was purified by column chromatography (silica gel, CHCl$_3$/MeOH, 1:9) to afford 75 (0.11 g, 70%) as a white solid: mp 178-180° C. $[\alpha]_D^{26}$ −15.56 (c 0.25, CHCl$_3$); $^1$H NMR (400 MHz, CDCl$_3$) δ 7.94-7.78 (m, 2H), 7.68 (s, 1H), 7.43 (dd, J=10.4, 4.7 Hz, 2H), 7.32 (dd, J=16.2, 8.7 Hz, 1H), 5.18 (s, 1H), 4.71-4.59 (m, 1H), 3.65 (s, 4H), 2.66-1.98 (m, 10H), 1.86-1.19 (m, 14H), 0.99 (d, J=9.7 Hz, 6H), 0.35 (dd, J=12.3, 8.0 Hz, 1H); $^{13}$C NMR (100 MHz, CDCl$_3$) δ 146.9, 130.8, 128.8, 128.0, 125.6, 119.9, 119.6, 70.3, 67.1, 59.9, 50.34, 50.30, 49.0, 46.1, 36.9, 34.5, 33.3, 32.5, 32.1, 31.8, 28.7, 25.2, 24.2, 20.0, 19.9, 18.4; HRMS (ESI) calcd for C$_{31}$H$_{43}$N$_4$O (M+H)$^+$ 487.3437. found 487.3437.

Example 76

(3S,10R,13S,17R)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-ol (76)

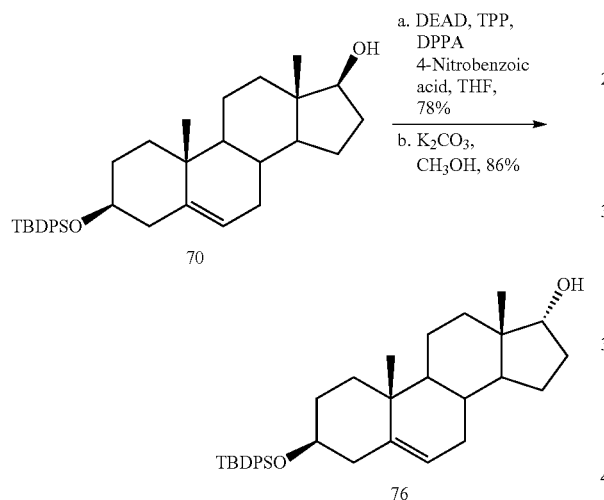

To a solution of triphenyl phosphine (3.87 g, 14.77 mmol) in THF (100 mL) was added diethyl azodicarboxylate (2.87 g, 16.25 mmol) at 0° C. and the resulted orange solution was stirred for 10 min. Alcohol 70 (3.90 g, 7.38 mmol) in THF (20 mL) was added to the above solution. After stirring for 10 min, a solution of 4-nitrobenzoic acid (2.96 g, 17.72 mmol) in THF (15 mL) was added. The reaction mixture was allowed to warm to room temperature and stirred for 12 h. The solvent was evaporated and the residue was purified by column chromatography (silica gel, EtOAc/hexanes, 15:85) to furnish 4-nitrobenzoate (3.90 g, 78%) as yellowish foam.

4-Nitrobenzoate (3.10 g, 4.64 mmol) was dissolved in THF (30 mL) and MeOH (10 mL). Powdered K$_2$CO$_3$ (1.28 g, 9.29 mmol) was added and the reaction mixture was stirred at room temperature overnight. EtOAc (100 mL) was added to dilute the reaction. It was filtered through a pad of celite. Purification by chromatography (EtOAc/hexanex 1:2) gave corresponding alcohol 76 (2.07 g, 86%) as viscous oil: $^1$H NMR (400 MHz, CDCl$_3$) δ 7.79-7.61 (m, 4H), 7.51-7.29 (m, 6H), 5.26-5.07 (m, 1H), 3.73 (d, J=5.9 Hz, 1H), 3.67-3.46 (m, 1H), 2.51-2.25 (m, 1H), 2.23-2.09 (m, 2H), 2.03-1.90 (m, 1H), 1.81-1.28 (m, 13H), 1.22-1.07 (m, 10H), 1.01 (s, 3H), 0.94-0.83 (m, 2H), 0.66 (s, 3H).

Example 77

(((3S,10R,13S,17S)-17-azido-10,13-dimethyl-2,3,4,7,8,9,10,11,12,13,14,15,16,17-tetradecahydro-1H-cyclopenta[a]phenanthren-3-yl)oxy)(tert-butyl)diphenylsilane (77)

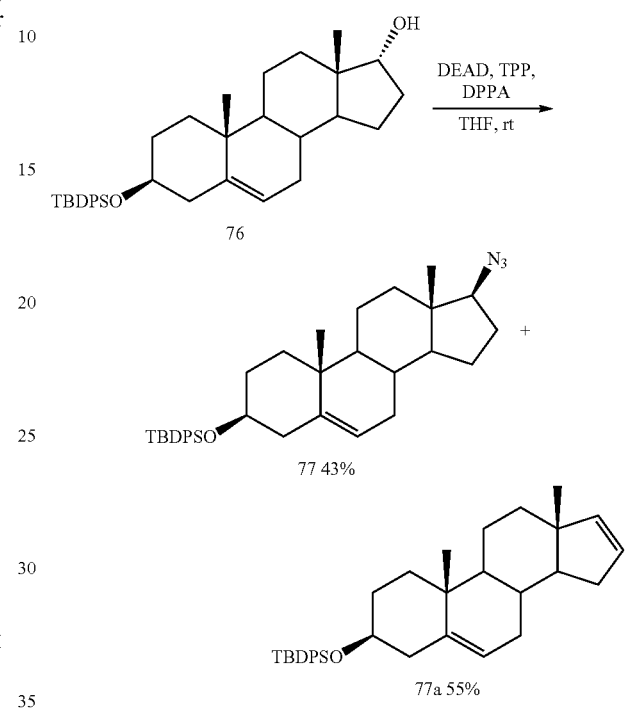

To a solution of triphenyl phosphine (1.22 g, 4.67 mmol) in THF (50 mL) was added diethyl azodicarboxylate (0.93 g, 5.39 mmol) at 0° C. and the resulted orange solution was stirred for 10 min. Alcohol 76 (1.90 g, 3.59 mmol) in THF (10 mL) was added to the above solution. After being stirred for 10 min, a solution of diphenylphosphoryl azide (1.68 g, 6.11 mmol) was added. The reaction mixture was allowed to warm to room temperature and stirred for 12 h. The solvent was evaporated and the residue was purified by column chromatography (silica gel, EtOAc/hexanes) to give 77 (0.85 g, 43%) along with eliminated product 77a (1.00 g, 55%) as yellow oil: LCMS (ESI) m/z 576.24 (M+Na)$^+$.

Example 78

1-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)-4-phenyl-1H-1,2,3-triazole (78)

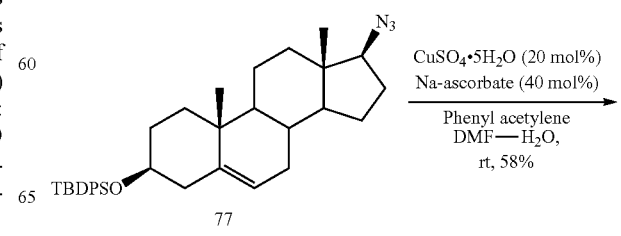

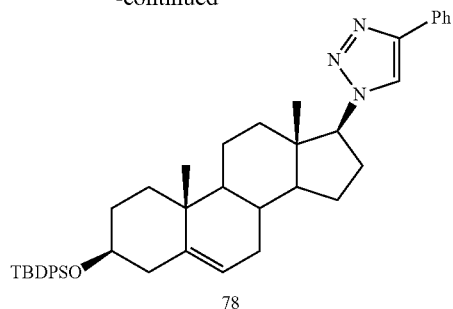
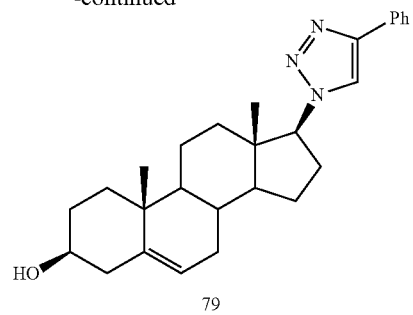

To a mixture of the azide 77 (0.40 g, 0.72, mmol) and phenyl acetylene (0.14 g, 1.44 mmol) in DMF (6 mL) was added sodium ascorbate (57 mg, 0.29 mmol) in H$_2$O (3 mL) and stirred for two minutes at ambient temperature. Then a CuSO$_4$.5H$_2$O (35 mg, 0.14 mmol) in H$_2$O (3 mL) was added to the above mixture. The mixture was stirred at room temperature for 12 h, added water (20 mL), and extracted with EtOAc (3×20 mL). Evaporation of combined organic extracts afforded a green solid, which was purified by flash chromatography (silica gel, acetone/hexanes, 2:8) to give compound 78 (0.27 g, 58%) as viscous oil: $^1$H NMR (400 MHz, CDCl$_3$) δ 7.86-7.80 (m, 2H), 7.73 (s, 1H), 7.68 (ddd, J=7.9, 3.4, 1.5 Hz, 4H), 7.47-7.31 (m, 9H), 5.14 (d, J=5.1 Hz, 1H), 4.41 (t, J=9.5 Hz, 1H), 3.63-3.45 (m, 1H), 2.69-2.46 (m, 1H), 2.41-2.22 (m, 2H), 2.15 (dd, J=13.3, 2.8 Hz, 1H), 2.09-1.76 (m, 3H), 1.77-1.43 (m, 7H), 1.40-1.12 (m, 4H), 1.06 (s, 9H), 1.00 (d, J=11.1 Hz, 3H), 0.97-0.80 (m, 2H), 0.59 (s, 3H). $^{13}$C NMR (100 MHz, CDCl$_3$) δ 146.89, 141.48, 135.79, 135.77, 134.77, 130.85, 129.49, 129.48, 128.81, 128.00, 127.50, 127.48, 125.67, 120.53, 119.09, 73.13, 70.66, 53.19, 50.01, 44.29, 42.45, 37.19, 36.92, 36.57, 32.01, 31.81, 31.48, 27.02, 25.88, 23.51, 20.60, 19.46, 19.15, 12.02.

Example 79

(3S,10R,13S,17S)-10,13-dimethyl-17-(4-phenyl-1H-1,2,3-triazol-1-yl)-2,3,4,7,8,9,10,11,12,13,14,15,16,17-tetradecahydro-1H-cyclopenta[a]phenanthren-3-ol (79)

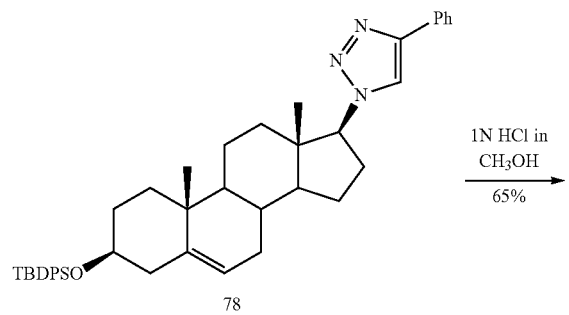

Silylated triazole 78 (0.17 g, 0.25 mmol) was dissolved in 1N HCl in MeOH (5 mL) and the solution was stirred for 5 h at room temperature. The reaction mixture was concentrated in vacuo. The residue was purified by column chromatography (silica gel, acetone/hexanes, 3:7) to give compound 79 (70 g, 65%) as a white solid: mp 278-280° C. $^1$H NMR (400 MHz, CDCl$_3$) δ 7.85 (s, 1H), 7.77 (d, J=6.8 Hz, 2H), 7.38 (t, J=7.1 Hz, 2H), 7.30 (t, J=7.9 Hz, 1H), 5.28 (d, J=23.0 Hz, 1H), 4.42 (t, J=8.9 Hz, 1H), 3.40 (m, 1H), 2.53 (m, 1H), 2.22 (dt, J=23.8, 15.3 Hz, 3H), 2.01 (d, J=15.0 Hz, 1H), 1.79 (d, J=13.0 Hz, 4H), 1.69-1.14 (m, 8H), 1.13-0.87 (m, 5H), 0.56 (s, 3H); $^{13}$C NMR (100 MHz, CDCl$_3$) δ 150.5, 144.9, 133.4, 132.8, 132.4, 129.6, 124.7, 124.0, 75.0, 74.9, 57.0, 53.9, 48.2, 45.6, 41.1, 40.6, 40.4, 35.9, 35.3, 34.9, 29.6, 27.3, 24.4, 23.1, 15.8; LCMS (ESI) m/z 418.41 (M+H)$^+$.

Example 80

(3S,10R,13S,17R)-17-ethynyl-10,13-dimethyl-2,3,4,7,8,9,10,11,12,13,14,15,16,17-tetradecahydro-1H-cyclopenta[a]phenanthren-3-ol (80)

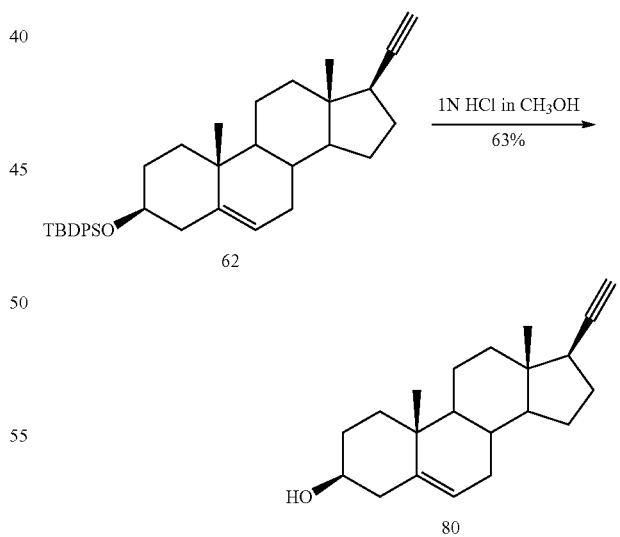

Silylated alkyne 62 (0.48 g, 0.89 mmol) was dissolved in 1N HCl in MeOH (10 mL) and the solution was stirred for 5 h at room temperature. The reaction mixture was concentrated in vacuo. The residue was purified by column chromatography (silica gel, acetone/hexanes, 2:7) to give compound 80 (0.160 g, 63%) as white solid: $^1$H NMR (400 MHz, CDCl$_3$) δ 5.36-5.29 (m, 1H), 3.59-3.43 (m, 1H), 2.38-2.10

(m, 3H), 2.09-1.94 (m, 2H), 1.93-1.77 (m, 3H), 1.76-1.37 (m, 8H), 1.34-1.14 (m, 1H), 1.16-0.87 (m, 7H), 0.79 (s, 3H); $^{13}$C NMR (100 MHz, CDCl$_3$) δ 140.8, 121.4, 85.9, 71.7, 69.8, 54.9, 50.1, 43.6, 42.2, 41.9, 37.3, 37.1, 36.6, 32.4, 31.8, 31.6, 29.0, 24.6, 20.8, 19.4, 13.3.

Example 81

(2S)-(3S,10R,13S,17S)-17-(1-benzyl-1H-1,2,3-triazol-4-yl)-10,13-dimethyl-2,3,4,7,8,9,10,11,12,13,14,15,16,17-tetradecahydro-1H-cyclopenta[a]phenanthren-3-yl 2-((((9H-fluoren-9-yl)methoxy)carbonyl)amino)-3-methylbutanoate (81)

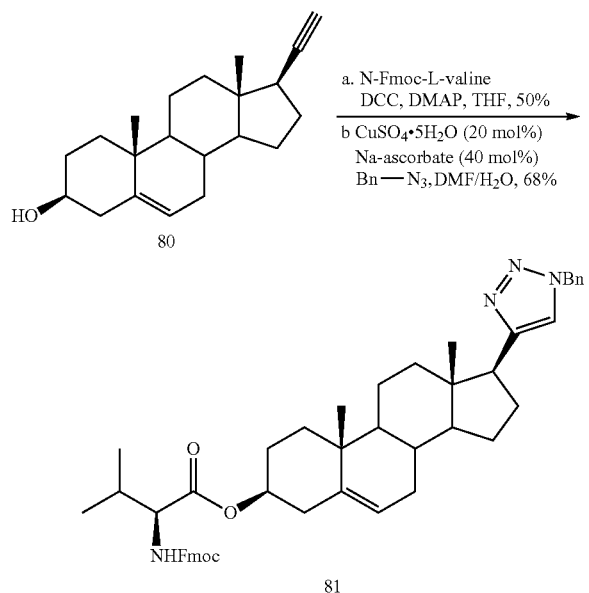

To a solution of compound 80 (0.48 g, 1.61 mmol), N-Fmoc-L-valine (0.60 g, 1.77 mmol) and 4-dimethylaminopyridine (19 mg, 0.16 mmol) in anhydrous THF (20 mL) was added dicyclohexylcarbodiimide (0.27 mL, 1.77 mmol) at ambient temperature. The solution was stirred overnight and then filtered through the celite. The filtrate was concentrated in vacuo and purified by column chromatography (ethyl acetate/hexanes, 2:8) to give N-Fmoc-L-valine ester (0.49 g, 50%) as white solid.

A mixture of the benzylazide (0.24 g, 1.86 mmol) and N-Fmoc-L-valine ester (0.57 g, 0.93 mmol) in DMF (12 mL) was added sodium ascorbate (73 mg, 0.37 mmol) in H$_2$O (6 mL) and stirred for two minutes at ambient temperature. Then a CuSO$_4$.5H$_2$O (46 mg, 0.18 mmol) in H$_2$O (6 mL) was added to the above mixture. The mixture was stirred at room temperature for 12 h, added water (6 mL), and extracted with EtOAc (3×20 mL). Evaporation of combined organic extracts afforded a green solid, which was purified by flash chromatography (hexanes/ethyl acetate, 3:7) to give compound 81 (0.47 g, 68%) as solid: $^1$H NMR (400 MHz, CDCl$_3$) δ 7.85 (d, J=7.5 Hz, 2H), 7.72 (dd, J=24.6, 7.4 Hz, 2H), 7.55-7.28 (m, 10H), 5.68-5.52 (m, 2H), 5.45 (dd, J=26.2, 6.4 Hz, 2H), 4.75 (t, J=19.2 Hz, 1H), 4.48 (d, J=7.1 Hz, 2H), 4.35 (dt, J=14.9, 5.8 Hz, 2H), 2.87 (t, J=9.8 Hz, 1H), 2.42 (d, J=7.8 Hz, 2H), 2.35-2.02 (m, 3H), 2.04-1.18 (m, 14H), 1.19-0.87 (m, 10H), 0.64-0.48 (m, 3H); $^{13}$C NMR (100 MHz, CDCl$_3$) δ 171.4, 156.2, 149.2, 143.9, 143.8, 141.3, 135.1, 129.0, 128.5, 127.8, 127.7, 127.0, 125.1, 122.7, 120.8, 119.9, 75.0, 66.9, 59.0, 55.9, 53.9, 50.1, 47.8, 47.2, 43.5, 38.0, 37.6, 36.9, 36.6, 32.2, 31.8, 31.4, 27.7, 26.6, 24.5, 20.6, 19.3, 18.9, 17.5, 12.9; LCMS (ESI) m/z 753.22 (M+H)$^+$.

Example 82

(2S)-(3S,10R,13S,17S)-17-(1-benzyl-1H-1,2,3-triazol-4-yl)-10,13-dimethyl-2,3,4,7,8,9,10,11,12,13,14,15,16,17-tetradecahydro-1H-cyclopenta[a]phenanthren-3-yl 2-amino-3-methylbutanoate (82)

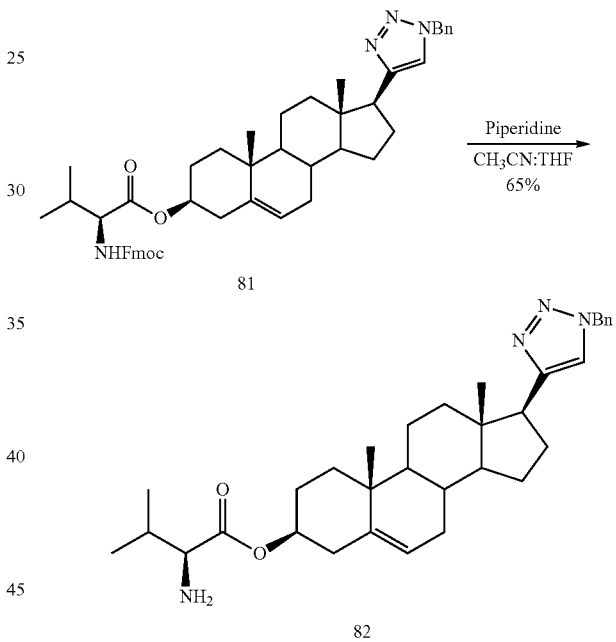

To a stirred solution of 81 (0.14 g, 0.19 mmol) in CH$_3$CN:THF (1:1, 6 mL) was added piperidine (0.18 mL, 1.90 mmol). After stirring for 20 min, solvent was removed under reduced pressure by the addition of toluene (5 mL) for complete removal of piperidine. The residue was purified by column chromatography (silica gel, MeOH/EtOAc, 2:98) to get 82 (63 mg, 65%) as white solid: mp 195-197° C. [α]$_D^{26}$ −7.74 (c 0.723, CHCl$_3$). $^1$H NMR (400 MHz, CDCl$_3$) δ 7.51-7.40 (m, 3H), 7.38-7.29 (m, 4H), 5.65-5.54 (m, 2H), 5.48 (d, J=4.7 Hz, 1H), 4.76 (tdd, J=11.1, 6.8, 4.2 Hz, 1H), 3.34 (d, J=4.9 Hz, 1H), 2.87 (t, J=9.8 Hz, 1H), 2.42 (d, J=7.0 Hz, 2H), 2.22-2.04 (m, 4H), 2.02-1.79 (m, 5H), 1.80-1.19 (m, 17H), 1.17-1.05 (m, 7H), 1.00 (d, J=6.8 Hz, 3H), 0.57 (s, 3H); $^{13}$C NMR (100 MHz, CDCl$_3$) δ 174.9, 149.2, 139.6, 135.1, 129.0, 128.5, 127.7, 122.5, 120.8, 74.2, 59.9, 55.9, 53.9, 50.1, 47.8, 43.5, 38.1, 37.6, 36.9, 36.7, 32.2, 31.8, 27.7, 26.6, 24.5, 20.6, 19.34, 19.29, 17.1, 12.9; LCMS (ESI) m/z 531.46 (M+H)$^+$.

Example 83

(2S)-(3S,10R,13S,17R)-17-ethynyl-10,13-dimethyl-2,3,4,7,8,9,10,11,12,13,14,15,16,17-tetradecahydro-1H-cyclopenta[a]phenanthren-3-yl-2,6-bis((tert-butoxycarbonyl)amino)hexanoate (83)

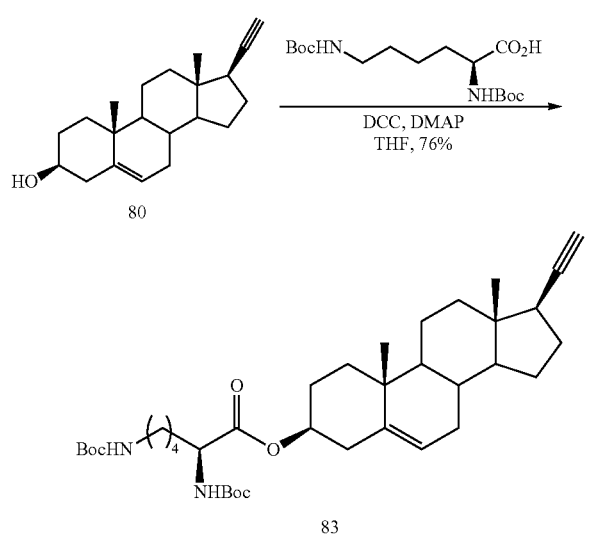

To a solution of compound 80 (0.19 g, 0.63 mmol), N,N-diBoc-L-lycine (0.24 g, 0.70 mmol) and 4-dimethylaminopyridine (7 mg, 0.006 mmol) in anhydrous THF (12 mL) was added dicyclohexylcarbodiimide (0.10 g, 0.70 mmol) at ambient temperature. The solution was stirred overnight and then filtered through celite. The filtrate was concentrated in vacuo and purified by column chromatography (acetone/hexanes, 3:7) to give compound 83 (0.30 g, 76%) as colorless oil: $^1$H NMR (400 MHz, CDCl$_3$) δ 5.37 (d, J=4.5 Hz, 1H), 5.07 (d, J=7.0 Hz, 1H), 4.73-4.51 (m, 2H), 4.22 (d, J=4.8 Hz, 1H), 3.11 (d, J=6.2 Hz, 2H), 2.31 (d, J=7.6 Hz, 2H), 2.25-2.13 (m, 1H), 2.12-1.95 (m, 2H), 1.94-0.89 (m, 43H), 0.81 (s, 3H); $^{13}$C NMR (100 MHz, CDCl$_3$) δ 172.1, 156.0, 155.4, 139.4, 122.6, 85.8, 79.7, 79.1, 74.8, 69.8, 54.8, 53.3, 50.0, 43.6, 41.8, 40.1, 37.9, 37.0, 36.9, 36.6, 32.5, 32.3, 31.8, 29.6, 29.0, 28.4, 28.3, 27.6, 24.6, 22.4, 20.8, 19.3, 13.3.

Example 84

(2S)-(3S,10R,13S,17S)-17-(1-benzyl-1H-1,2,3-triazol-4-yl)-10,13-dimethyl-2,3,4,7,8,9,10,11,12,13,14,15,16,17-tetradecahydro-1H-cyclopenta[a]phenanthren-3-yl 2,6-bis((tert-butoxycarbonyl)amino)hexanoate (84)

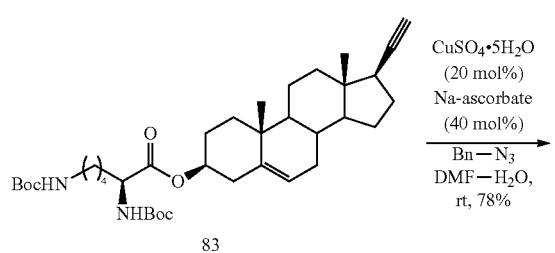

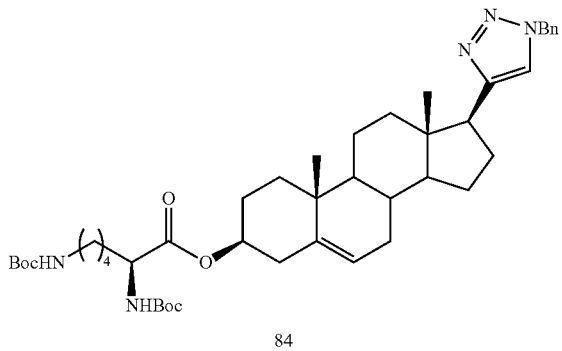

A mixture of the benzyl azide (0.13 g, 1.0 mmol) and alkyne 83 (0.31 g, 0.50 mmol) in DMF (6 mL) was added sodium ascorbate (39 mg, 0.20 mmol) in H$_2$O (3 mL) and stirred for 2 min at ambient temperature. Then a CuSO$_4$.5H$_2$O (24 mg, 0.10 mmol) in H$_2$O (3 mL) was added to the above mixture. The mixture was stirred at room temperature for 12 h, added water (6 mL), and extracted with EtOAc (3×15 mL). Evaporation of combined organic extracts afforded a green solid, which was purified by flash chromatography (hexanes/ethyl acetate, 4:6) to give compound 84 (0.29 g, 78%) as solid: $^1$H NMR (400 MHz, CDCl$_3$) δ 7.49-7.39 (m, 3H), 7.34 (d, J=5.8 Hz, 1H), 7.32 (dd, J=7.5, 1.8 Hz, 2H), 5.65-5.55 (m, 2H), 5.47 (d, J=3.9 Hz, 1H), 5.18 (d, J=7.5 Hz, 1H), 4.85-4.59 (m, 2H), 4.31 (d, J=4.6 Hz, 1H), 3.19 (d, J=6.1 Hz, 2H), 2.87 (t, J=9.8 Hz, 1H), 2.40 (d, J=7.7 Hz, 2H), 2.23-2.02 (m, 3H), 2.01-1.16 (m, 38H), 1.16-1.00 (m, 4H), 0.57 (s, 3H); $^{13}$C NMR (100 MHz, CDCl$_3$) δ 172.1, 156.0, 155.4, 149.2, 139.4, 135.1, 129.0, 128.5, 127.7, 122.7, 120.8, 79.7, 79.1, 74.9, 55.9, 53.9, 53.3, 50.1, 47.8, 43.5, 40.1, 37.9, 37.6, 36.9, 36.6, 32.4, 32.2, 31.8, 29.5, 28.4, 28.3, 27.6, 26.6, 24.5, 22.4, 20.6, 19.3, 12.9.

Example 85

(2S)-(3S,10R,13S,17S)-17-(1-benzyl-1H-1,2,3-triazol-4-yl)-10,13-dimethyl-2,3,4,7,8,9,10,11,12,13,14,15,16,17-tetradecahydro-1H-cyclopenta[a]phenanthren-3-yl 2,6-diaminohexanoate (85)

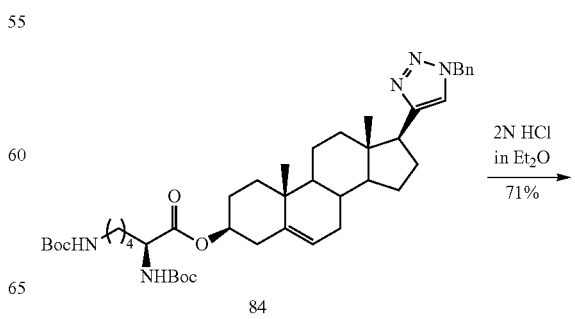

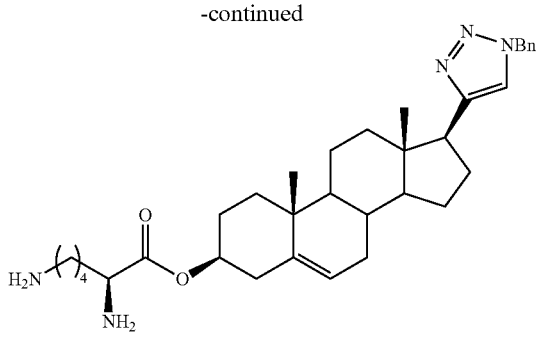

85

Compound 84 (0.20 g, 0.26 mmol) was dissolved in 2N HCl in ether (10 mL), and the reaction mixture was stirred at room temperature for overnight. The solvent was removed under vacuum and the residue was purified by column chromatography (silica gel, MeOH/CH$_2$Cl$_2$, 2:8) to get 85 (0.10 g, 71%) as yellowish solid: mp 258-260° C.; [α]$_D^{26}$– 0.50 (c 0.59, MeOH). $^1$H NMR (400 MHz, CD$_3$OD) δ 8.02 (s, 1H), 7.36 (s, 5H), 5.56 (s, 2H), 5.45 (s, 1H), 4.02 (s, 1H), 2.91-2.75 (m, 3H), 2.60-2.31 (m, 2H), 2.30-0.84 (m, 26H), 0.53 (s, 3H); $^{13}$C NMR (100 MHz, CD$_3$OD) δ 169.7, 140.5, 136.2, 130.1, 129.8, 129.3, 125.5, 124.1, 77.9, 57.2, 56.1, 54.1, 51.6, 44.9, 40.9, 39.1, 38.6, 38.21, 37.8, 33.5, 33.0, 31.4, 28.8, 28.3, 27.8, 25.5, 23.5, 21.9, 20.0, 13.6; LCMS (ESI) m/z 560.52 (M+H)$^+$.

Example 86

(3R,10R,13S,17R)-3-azido-17-ethynyl-10,13-dimethyl-2,3,4,7,8,9,10,11,12,13,14,15,16,17-tetradecahydro-1H-cyclopenta[a]phenanthrene (86)

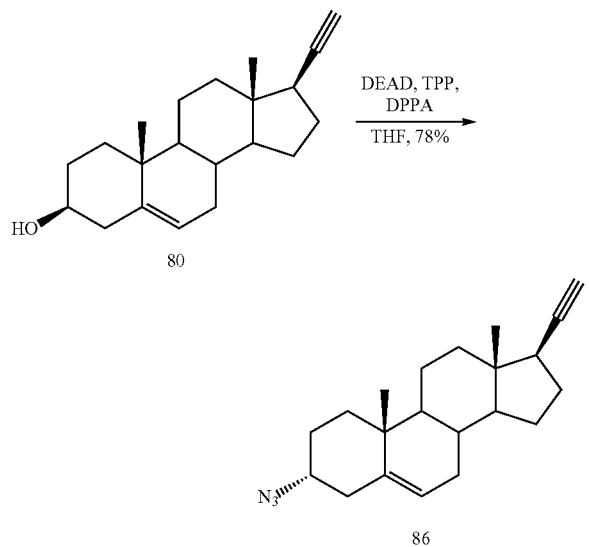 [SMILES: C#C[C@H]1CCC2C3CC=C4C[C@@H](O)CC[C@]4(C)C3CC[C@@]21C ; C#C[C@H]1CCC2C3CC=C4C[C@H](N=[N+]=[N-])CC[C@]4(C)C3CC[C@@]21C]

To a solution of triphenyl phosphine (0.16 g, 0.48 mmol) in THF (10 mL) was added diethyl azodicarboxylate (0.33 g, 0.72 mmol) at 0° C. and the resulted orange solution was stirred for 10 min. Alcohol 80 (0.14 g, 0.48 mmol) in THF (3 mL) was added to the above solution. After being stirred for 10 min, a solution of diphenylphosphoryl azide (0.17 mL, 0.82 mmol) was added. The reaction mixture was allowed to warm to room temperature and stirred for 10 h. The solvent was evaporated and the residue was purified by column chromatography (silica gel, acetone/hexanes, 5:95) to get 86 (0.12 g, 78%) as yellowish oil: $^1$H NMR (400 MHz, CDCl$_3$) δ 5.51-5.23 (m, 1H), 3.99-3.75 (m, 1H), 2.58-2.47 (m, 1H), 2.19 (ddd, J=9.3, 5.7, 3.1 Hz, 2H), 2.12-1.95 (m, 3H), 1.93-1.85 (m, 1H), 1.69 (ddddd, J=17.9, 13.3, 7.1, 5.5, 3.2 Hz, 8H), 1.53-1.34 (m, 3H), 1.33-1.19 (m, 1H), 1.16-1.06 (m, 2H), 1.05-0.92 (m, 4H), 0.81 (s, 3H); $^{13}$C NMR (100 MHz, CDCl$_3$) δ 138.1, 122.8, 85.9, 69.8, 58.1, 54.9, 49.9, 43.6, 41.8, 37.1, 37.0, 36.0, 33.6, 32.2, 31.7, 29.0, 26.0, 24.6, 20.5, 19.0, 13.3.

Example 87 tert-butyl ((3R,10R,13S,17R)-17-ethynyl-10,13-dimethyl-2,3,4,7,8,9,10,11,12,13,14,15,16,17-tetradecahydro-1H-cyclopenta[a]phenanthren-3-yl)carbamate (87)

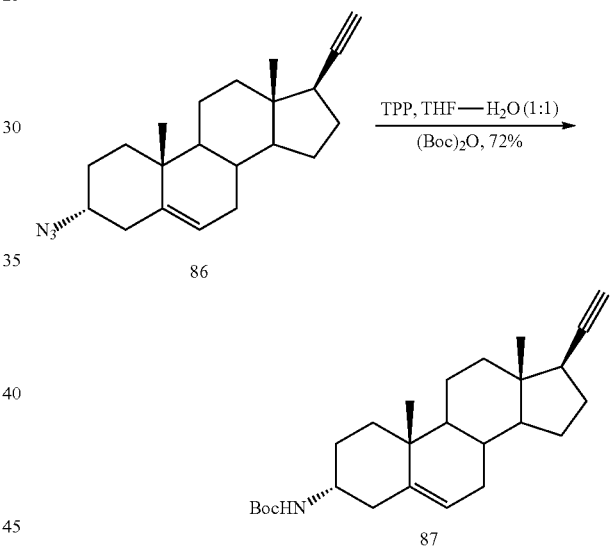

To a solution of azide 86 (0.12 g, 0.38 mmol) in THF (10 mL) was added triphenyl phosphine (0.13 g, 0.50 mmol) at ambient temperature. After being stirred for 1 h, the reaction mixture was diluted with H$_2$O (5 mL) and (Boc)$_2$O (0.12 g, 0.58 mmol) was added and stirred at the same temperature for an additional 10 h. The volatiles were evaporated and purified by column chromatography (silica gel, hexanes/ethyl acetate) to afford compound 87 (0.11 g, 72%) as white foam: $^1$H NMR (400 MHz, CDCl$_3$) δ 5.53-5.21 (m, 1H), 4.62 (d, J=6.9 Hz, 1H), 3.89 (d, J=25.7 Hz, 1H), 2.56 (d, J=13.7 Hz, 1H), 2.23-2.13 (m, 1H), 2.11-1.84 (m, 5H), 1.81-1.55 (m, 8H), 1.51-1.38 (m, 11H), 1.34-1.15 (m, 3H), 1.14-0.84 (m, 7H), 0.82 (d, J=9.2 Hz, 3H). $^{13}$C NMR (100 MHz, CDCl$_3$) δ 155.0, 139.0, 122.9, 85.8, 78.9, 69.8, 54.9, 50.3, 46.6, 43.6, 41.9, 37.3, 37.1, 33.9, 32.3, 31.8, 31.5, 29.0, 28.4, 26.3, 24.6, 20.5, 18.9, 13.3.

Example 88 tert-butyl ((3R,10R,13S,17S)-17-(1-benzyl-1H-1,2,3-triazol-4-yl)-10,13-dimethyl-2,3,4,7,8,9,10,11,12,13,14,15,16,17-tetradecahydro-1H-cyclopenta[a]phenanthren-3-yl)carbamate (88)

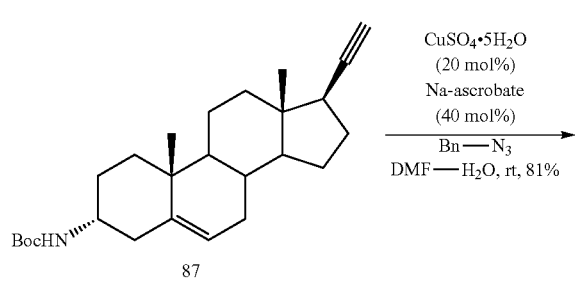

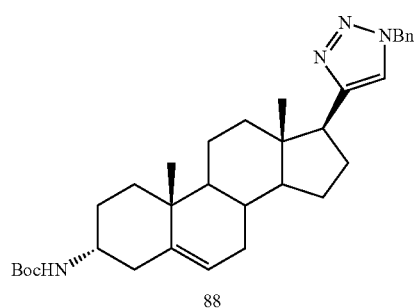

A mixture of the benzyl azide (0.06 g, 0.50 mmol) and alkyne 87 (0.10 g, 0.25 mmol) in DMF (6 mL) was added sodium ascorbate (19 mg, 0.10 mmol) in H₂O (3 mL) and stirred for two minutes at ambient temperature. Then a CuSO₄.5H₂O (12 mg, 0.10 mmol) in H₂O (3 mL) was added to the above mixture. The mixture was stirred at room temperature for 12 h, added water (6 mL), and extracted with EtOAc (3×10 mL). Evaporation of combined organic extracts afforded a green solid, which was purified by flash chromatography (silica gel, acetone/hexanes, 3:7) to give compound 88 (0.10 g, 81%) as white solid: ¹H NMR (400 MHz, CDCl₃) δ 7.51-7.39 (m, 3H), 7.37-7.28 (m, 3H), 5.64-5.53 (m, 2H), 5.46 (d, J=4.7 Hz, 1H), 4.73 (d, J=7.4 Hz, 1H), 3.95 (s, 1H), 2.88 (t, J=9.8 Hz, 1H), 2.65 (d, J=14.1 Hz, 1H), 2.20-1.97 (m, 4H), 1.96-1.60 (m, 10H), 1.60-1.49 (m, 9H), 1.49-1.12 (m, 7H), 1.08 (s, 3H), 0.56 (s, 3H); ¹³C NMR (100 MHz, CDCl₃) δ 155.1, 149.2, 139.0, 135.1, 129.0, 128.5, 127.8, 123.0, 120.8, 79.0, 56.0, 53.9, 50.4, 47.9, 46.6, 43.4, 37.6, 37.4, 33.9, 32.2, 31.9, 28.4, 26.69, 26.39, 24.5, 20.4, 18.8, 12.9.

Example 89

1-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)-2-hydroxyethanone (89)

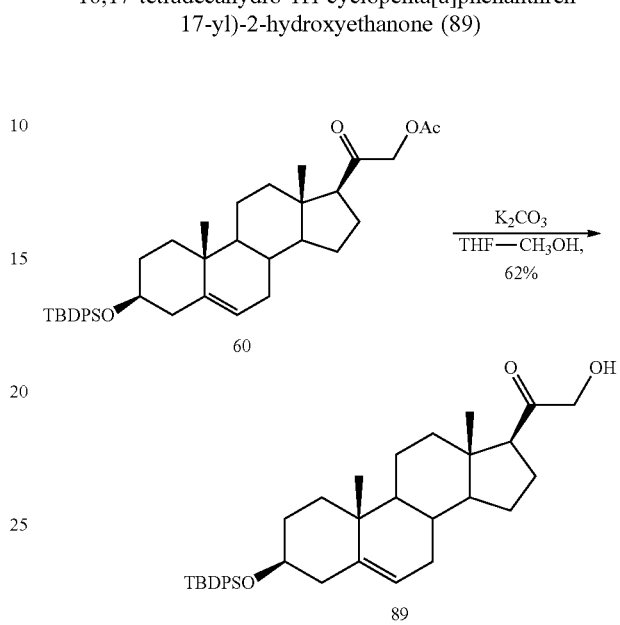

Acetate 60 (0.50 g, 0.81 mmol) was dissolved in THF (10 mL) and MeOH (10 mL). Powdered K₂CO₃ (0.33 g, 2.45 mmol) was added and the reaction mixture was stirred at room temperature overnight. EtOAc (50 mL) was added to dilute the reaction and filtered through a pad of silica gel. The reaction mixture concentrated and the residue was directly purified by column chromatography (silica gel, hexanes/EtOAc 1:1) to give the corresponding alcohol 89 (0.288 g, 62%) as white solid: ¹H NMR (400 MHz, CDCl₃) δ 7.72-7.64 (m, 4H), 7.46-7.31 (m, 6H), 5.12 (d, J=5.1 Hz, 1H), 4.28-4.06 (m, 2H), 3.61-3.45 (m, 1H), 3.25 (s, 1H), 2.48-2.08 (m, 4H), 2.02-1.81 (m, 2H), 1.79-1.16 (m, 13H), 1.06 (s, 10H), 0.98 (s, 3H), 0.85 (tt, J=22.5, 11.2 Hz, 2H), 0.66-0.58 (m, 3H); ¹³C NMR (100 MHz, CDCl₃) δ 210.3, 141.3, 135.77, 135.76, 134.77, 134.76, 129.45, 129.43, 127.46, 127.44, 120.6, 73.1, 69.4, 59.2, 56.9, 49.8, 44.7, 42.4, 38.5, 37.1, 36.4, 31.82, 31.79, 31.72, 26.9, 24.5, 22.9, 20.9, 19.3, 19.1, 13.3.

Example 90

4-((3S,10R,13S,17S)-3-((tert-butyldiphenylsilyl)oxy)-10,13-dimethyl-2,3,4,7,8,9,10,11,12,13,14,15,16,17-tetradecahydro-1H-cyclopenta[a]phenanthren-17-yl)furan-2(5H)-one (90)

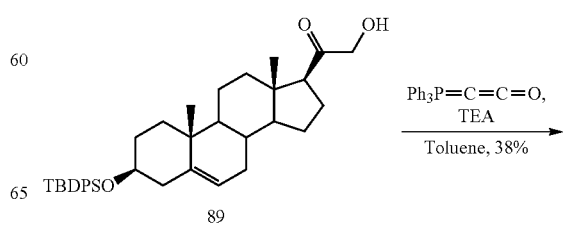

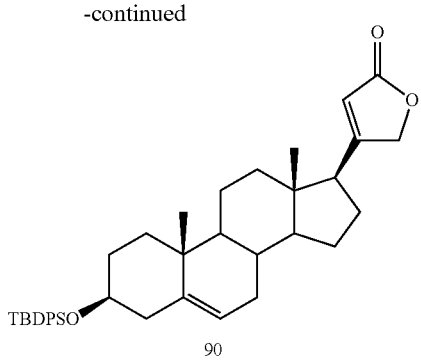

To a mixture of hydroxyketone 89 (0.24 g, 0.42 mmol), triethylamine (0.29 mL, 2.10 mmol) in toluene (10 mL) was added triphenylphosphoranylidene ketene (016 g, 084 mmol) at room temperature and the reaction was stirred for 24 h for overnight. The reaction mixture concentrated and the residue was directly purified by column chromatography (silica gel, hexanes/EtOAc 1:1) to give the 90 (0.09 g, 38%) as white solid: $^1$H NMR (400 MHz, CDCl$_3$) δ 7.74-7.58 (m, 4H), 7.51-7.28 (m, 6H), 5.82 (d, J=1.5 Hz, 1H), 5.22-5.03 (m, 1H), 4.86-4.56 (m, 2H), 3.66-3.41 (m, 1H), 2.36 (dt, J=23.7, 9.4 Hz, 2H), 2.24-2.09 (m, 2H), 2.04-1.85 (m, 2H), 1.84-1.14 (m, 14H), 1.06 (s, 9H), 0.99 (d, J=4.0 Hz, 3H), 0.86 (ddd, J=13.8.5, 7.2, 3.7 Hz, 2H), 0.62 (d, J=4.9 Hz, 3H).

Example 91

4-((3S,10R,13S,17S)-3-hydroxy-10,13-dimethyl-2,3,4,7,8,9,10,11,12,13,14,15,16,17-tetradecahydro-1H-cyclopenta[a]phenanthren-17-yl)furan-2(5H)-one (91)

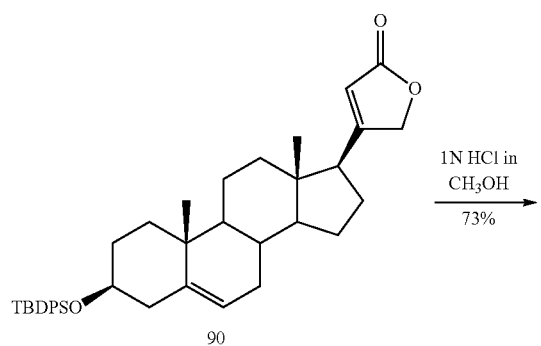

Silylated lactone 90 (0.07 g, 0.11 mmol) was dissolved in MeOH/1N HCl (4:1, 3 mL) and the solution stirred for 5 h at room temperature. The reaction mixture was concentrated in vacuo. The residue was purified by column chromatography (silica gel, acetone/hexanes, 4:6) to give 91 (0.03 g, 73%) as white solid: mp 286-287° C.; $[\alpha]_D^{26}$ −9.73 (c 0.26, CHCl$_3$:MeOH (3:1)); $^1$H NMR (400 MHz, CDCl$_3$+CD$_3$OD) 5.78 (s, 1H), 5.28 (s, 1H), 4.82-4.60 (m, 2H), 2.37-2.08 (m, 3H), 1.94-1.85 (m, 2H), 1.84-1.63 (m, 6H), 1.63-1.34 (m, 5H), 1.32-1.06 (m, 4H), 1.07-0.86 (m, 5H), 0.57 (s, 3H); $^{13}$C NMR (100 MHz, CDCl$_3$) δ 174.8, 172.0, 140.8, 121.0, 115.7, 73.7, 71.1, 56.4, 50.7, 49.9, 44.3, 41.7, 37.9, 37.1, 36.4, 32.0, 31.5, 31.1, 25.8, 24.3, 20.7, 19.2, 13.0; LCMS (ESI) m/z 357.36 (M+H)$^+$.

Example 92

The following illustrate representative pharmaceutical dosage forms, containing a compound of formula I ('Compound X'), for therapeutic or prophylactic use in humans.

| (i) Tablet 1 | |
|---|---|
| | mg/tablet |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | |
|---|---|
| | mg/tablet |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | |
|---|---|
| | mg/capsule |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | |
|---|---|
| | mg/ml |
| Compound X = (free acid form) | 1.0 |
| Dibasic sodium phosphate | 12.0 |
| Monobasic sodium phosphate | 0.7 |
| Sodium chloride | 4.5 |

-continued

(iv) Injection 1 (1 mg/ml)

| | mg/ml |
|---|---|
| 1.0N Sodium hydroxide solution (pH adjustment to 7.0-7.5) | q.s. |
| Water for injection | q.s. ad 1 mL |

(v) Injection 2 (10 mg/ml)

| | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

(vi) Aerosol

| | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Example 93

Figure 2:
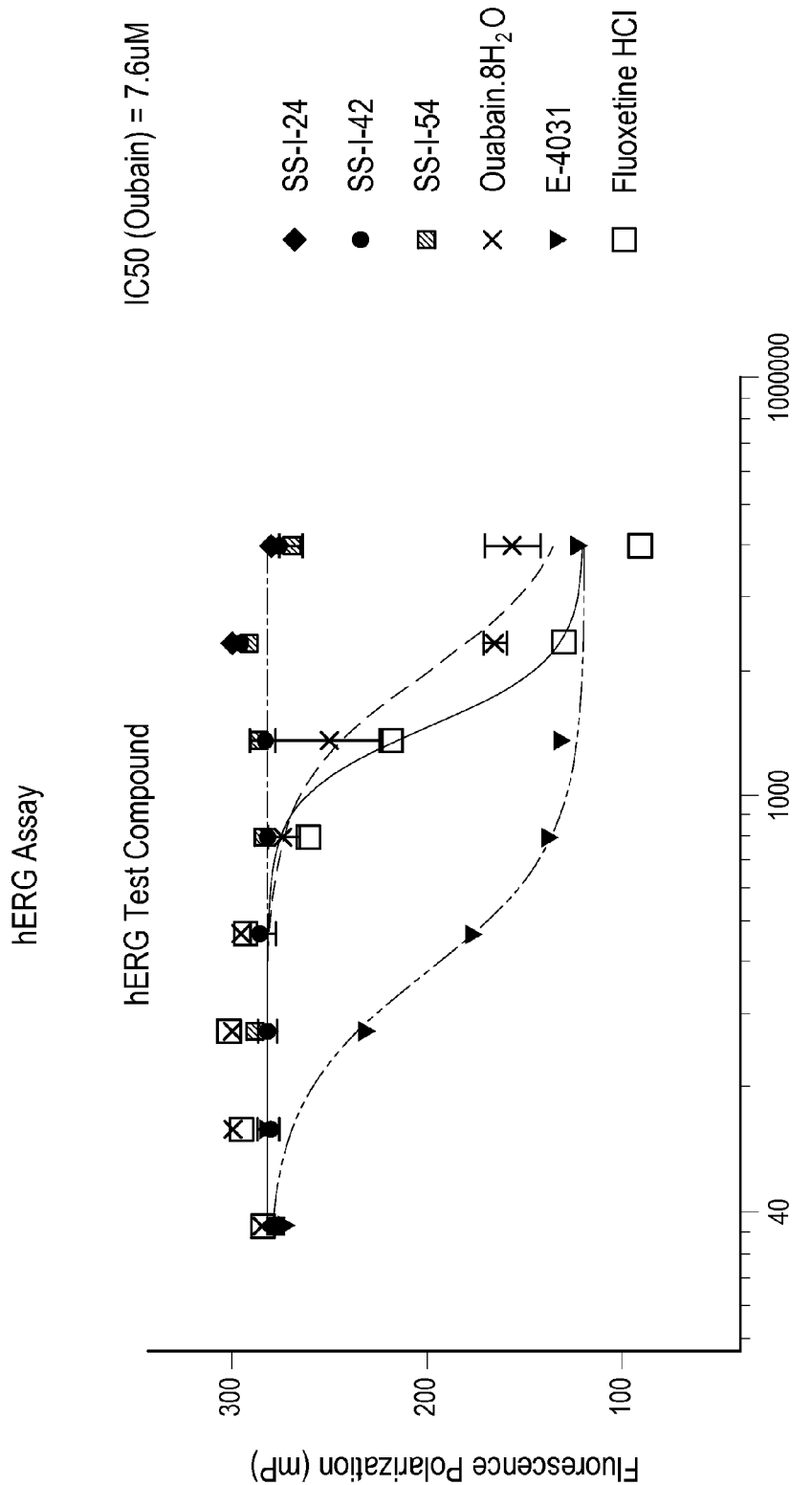
FIG. 2 includes a graph that illustrates data of fluorescence polarization versus compound concentration of hERG test compounds.

A hERG assay was conducted. We have assessed the effect of compound SS-I-54 on human ether-a-go-go related gene (hERG) tail current recorded from human embryonic kidney (HEK293) cells stably transfected with hERG cDNA. Compounds which affect the hERG channel in cell culture are known to prolong the QTc interval in patients and lead to potentially life threatening arrhythmias. Performing this assay is relevant for our compounds, since cardenolides have the potential of targeting the heart. Importantly, SS-I-54, SS-48 and SS-I-24 had no significant effect on hERG. In contrast, ouabain, the naturally occurring cardenolide, from which we derived our compounds inhibited hERG activity. FIG. 2 includes a graph that illustrates data of fluorescence polarization versus compound concentration of hERG test compounds showing the above-discussed results.

Example 94

Figure 3:
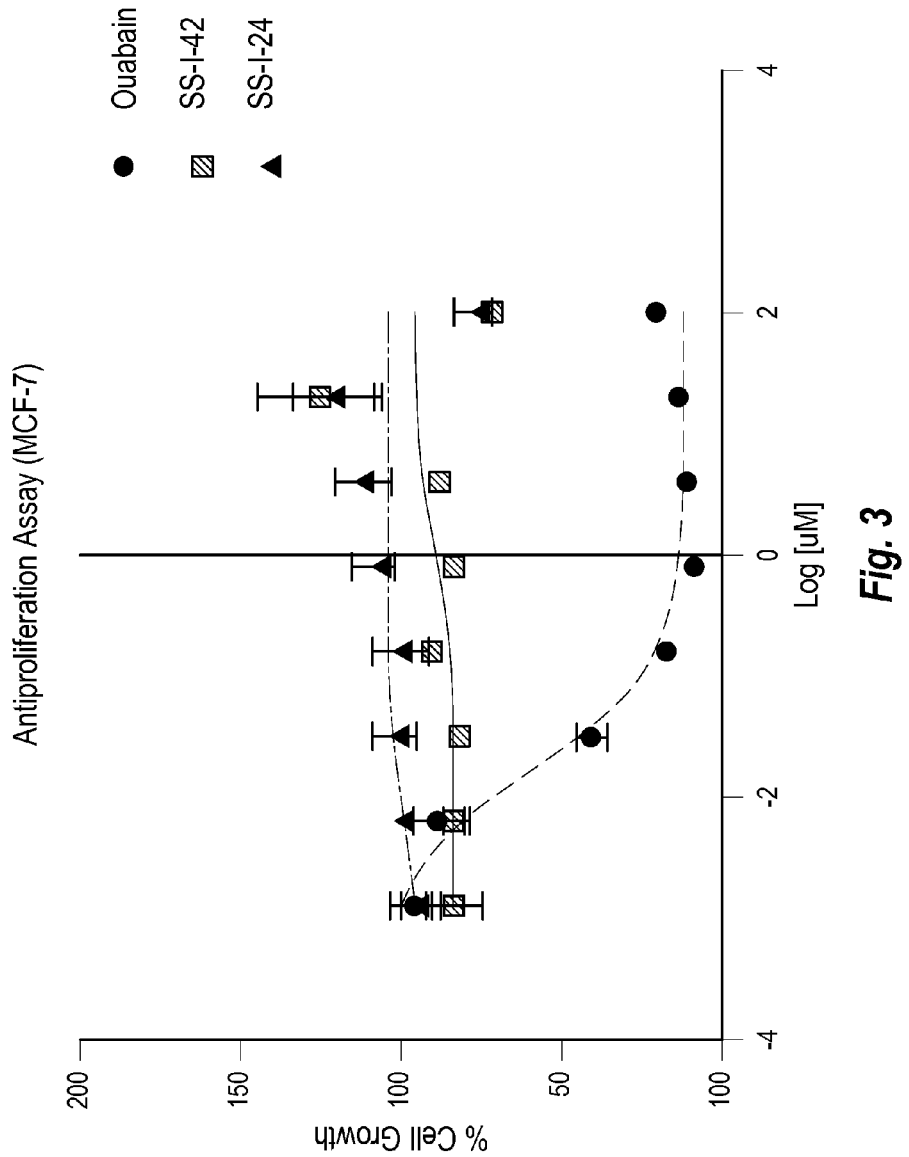
FIG. 3 includes a graph that illustrates percent cell growth versus concentration for hERG test compounds in an antiproliferation assay.

An antiproliferative assay was conducted with MCF-7 cells. This assay follows the proliferation and viability of cells after administration of increasing concentrations of the tested compound. In contrast to ouabain, SS-I-42 and SS-I-24 had no significant effect on cell proliferation, suggesting lack of toxicity under these studies. FIG. 3 includes a graph that illustrates percent cell growth versus concentration for hERG test compounds in an antiproliferation assay showing the above-discussed results.

Example 95

A metabolic stability assay was conducted to assess the metabolic stability of a compound based on the rate of disappearance of compound from rodents (mouse and rat), non-rodent (dog and monkey), and human hepatic microsomal S9 fractions. Compound SS-I-54 was tested at a concentration of $10^{-6}$ M in each species, and after incubation with the S9 microsomes, the remaining compound was measured by HPLC. SS-I-54 showed good metabolic stability and a low degree of degradation. The metabolic stability showed: in mouse, the compound remaining was 76%; in rat, the compound remaining was 95%; in dog, the compound remaining was 99%; in monkey, the compound remaining was 89%; and in human, the compound remaining was 107%.

Example 96

An in vitro permeability assay was conducted. This assays tests the capacity of a compound to traverse an epithelium layer and gives an estimate of the extent to which a given compound crosses cell membranes and of the in vitro absorption of the compound. We tested our SS-I-54 compound in vitro on human colon carcinoma cells (Caco-2 cells) grown on polarized transwell culture filters. SS-I-54 was applied at a concentration of $10^{-5}$ M either at the basal, or apical side of the cells. Aliquots of the media at the opposite side of the cell monolayer were taken to measure the levels of SS-I-54. Results showed that the cells had a low permeability for SS-I-54, which was almost all recovered in the media. In apical to basal, mean recovery was 94%. In basal to apical, mean recovery was 98%.

Example 97

Figures 4A, 4B, 4C:
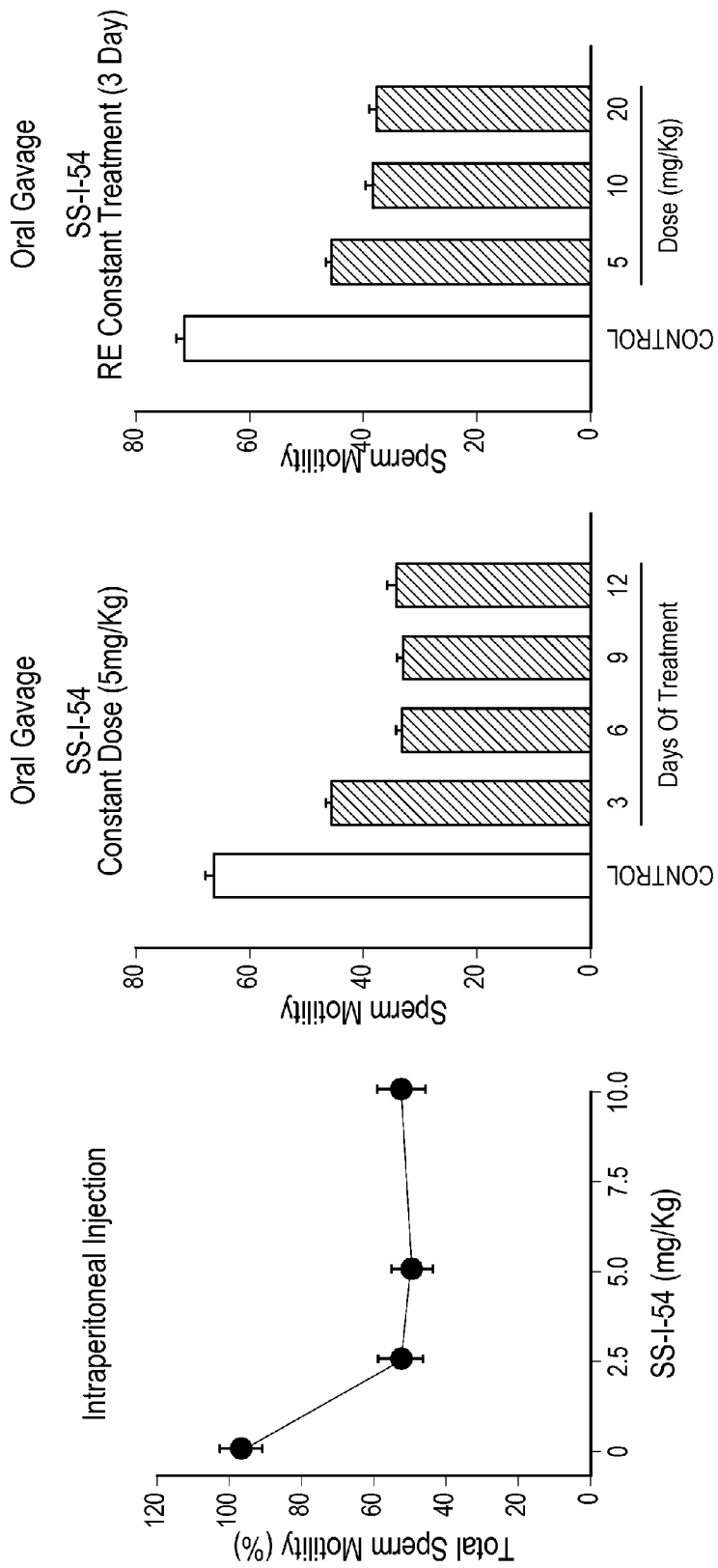
FIG. 4A includes a graph that illustrates total sperm motility percent versus dose for intraperitoneal injection of SS-I-54.
FIG. 4B includes a graph that illustrates sperm motility percent versus days of treatment for oral gavage of SS-I-54 when dosed at 5 mg/Kg.
FIG. 4C includes a graph that illustrates sperm motility percent versus dose for oral gavage of SS-I-54 at day 3 of treatment.

Studies were conducted that shows synthetic cardenolides of the invention inhibit sperm motility in vivo. To test whether our lead cardenolides can also inhibit sperm movement in vivo, we have measured motility of caudal epididymal sperm in rats treated with SS-I-54. We administered SS-I-54 to rats. SS-I-54 was dissolved in Captisol™ and this vehicle alone was used in our controls. Dose and time response effects with SS-I-54 were determined. When SS-I-54 was administered via intraperitoneal (i.p.) injection, it inhibited sperm motility at concentrations as low as 2.5 mg/Kg weight (FIG. 4A). Also, when rats were treated with SS-I-54 via oral gavage, using a constant dose of 5 mg/Kg for different days (3, 6, 9 and 12 days), or a variable dose of 5, 10 and 20 mg/Kg for only 3 days, SS-I-54 inhibited sperm motility. These results show that SS-I-54 effectively interferes with sperm motility in whole rats, validating the in vivo action of cardenolides in this species. FIG. 4A includes a graph that illustrates total sperm motility percent versus dose for intraperitoneal injection of SS-I-54. FIG. 4B includes a graph that illustrates sperm motility percent versus days of treatment for oral gavage of SS-I-54 when dosed at 5 mg/Kg. FIG. 4C includes a graph that illustrates sperm motility percent versus dose for oral gavage of SS-I-54 at day 3 of treatment.

Example 98

An in vitro fertilization assay was conducted. We tested the capacity of SS-I-54 to inhibit fertilization in vitro. We incubated spermatozoa from the cauda epididymis of mice in the presence and absence of SS-I-54 at a concentration of $10^{-8}$ M and in vitro fertility assays were performed. Compared to untreated controls, SS-I-54 reduced the formation of two cell embryos by approximately 70%. This shows the effectiveness of the cardenolide to interfere sperm fertility.

Figure 5:
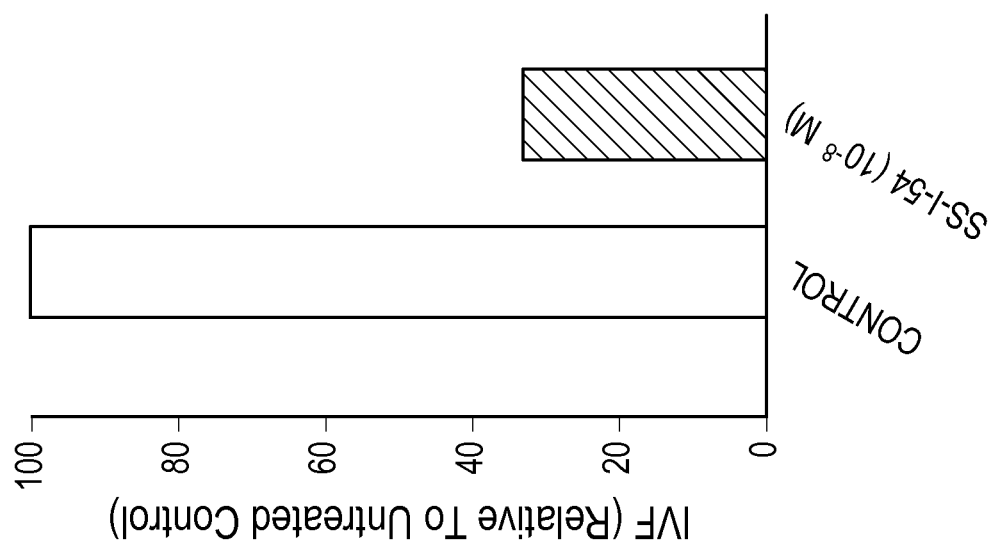
FIG. 5 includes a graph that illustrates percentage of in vitro fertilization with SSI-54 or without (control).

FIG. 5 includes a graph that illustrates percentage of in vitro fertilization with SSI-54 or without (control) showing these results.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula:

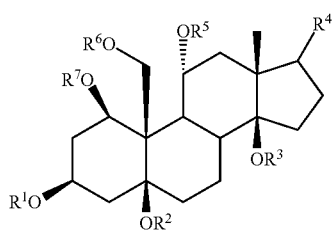

wherein:
- $R^1$ is H, $(C_1-C_6)$alkyl, or $R_c$, wherein the $(C_1-C_6)$alkyl is optionally substituted with one or more halo or $(C_1-C_6)$alkoxy;
- $R^2$ is H or $(C_1-C_6)$alkyl, wherein the $(C_1-C_6)$alkyl is optionally substituted with one or more halo or $(C_1-C_6)$alkoxy;
- $R^3$ is H or $(C_1-C_6)$alkyl, wherein the $(C_1-C_6)$alkyl is optionally substituted with one or more halo or $(C_1-C_6)$alkoxy;
- $R^4$ is $R_a$, cyano, formyl, carboxy, hydroximinomethyl, $(C_1-C_4)$alkyl, $(C_2-C_4)$alkenyl, $(C_2-C_4)$alkynyl, aryl, heteroaryl, or $(C_1-C_4)$alkanoyl, wherein the $(C_1-C_4)$alkyl, $(C_2-C_4)$alkenyl, $(C_2-C_4)$alkynyl, and $(C_1-C_4)$alkanoyl is optionally substituted with one or more groups selected from hydroxy, halo, aryl, and heteroaryl; wherein any aryl and heteroaryl of $R^4$ is optionally substituted with one or more $R_b$;
- $R^5$ is H or $(C_1-C_6)$alkyl, wherein the $(C_1-C_6)$alkyl is optionally substituted with one or more halo or $(C_1-C_6)$alkoxy;
- $R^6$ is H or $(C_1-C_6)$alkyl, wherein the $(C_1-C_6)$alkyl is optionally substituted with one or more halo or $(C_1-C_6)$alkoxy; and
- $R^7$ is H or $(C_1-C_6)$alkyl, wherein the $(C_1-C_6)$alkyl is optionally substituted with one or more halo or $(C_1-C_6)$alkoxy; or $R^6$ and $R^7$ taken together form a $(C_1-C_6)$alkylene;
- $R_a$, is a 4, 5, or 6 membered saturated or partially unsaturated heterocyclic ring comprising at least one carbon atom and at least one heteroatom selected from S, or NH in the ring, which ring is optionally substituted with one or more oxo (=O);
- $R_b$, is aryl or aryl($C_1-C_6$)alkyl, wherein the aryl or aryl $(C_1-C_6)$alkyl is optionally substituted with one or more $(C_1-C_6)$alkoxy or halo;
- $R_c$, is a C-linked amino acid, a C-linked dipeptide, —C(=O)CH$_2$CH$_2$COOH, —P(=O)(OH)$_2$, or:

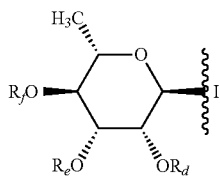

$R_d$ is H, $(C_1-C_6)$alkanoyl, or $(C_1-C_6)$alkyl, wherein the $(C_1-C_6)$alkanoyl and the $(C_1-C_6)$alkyl are each optionally substituted with one or more halo or $(C_1-C_6)$alkoxy; and $R_e$ is H, $(C_1-C_6)$alkanoyl, or $(C_1-C_6)$alkyl, wherein the $(C_1-C_6)$alkanoyl and the $(C_1-C_6)$alkyl are each optionally substituted with one or more halo or $(C_1-C_6)$alkoxy; or $R_d$ and $R_e$ taken together form a $(C_1-C_6)$alkylene; and $R_f$ is H, $(C_1-C_6)$alkanoyl, or $(C_1-C_6)$alkyl, wherein the $(C_1-C_6)$alkanoyl and the $(C_1-C_6)$alkyl are each optionally substituted with one or more halo or $(C_1-C_6)$alkoxy;

or a salt thereof,
when $R_c$, is

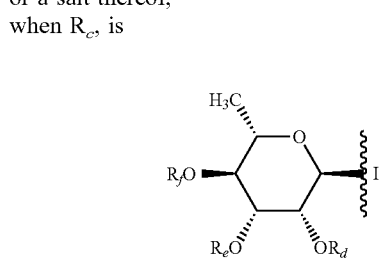

then $R^4$ is

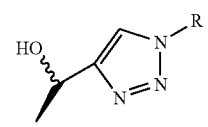

with R being 4-fluorobenzyl or benzyl,
when $R^4$ is carboxy, then $R^1$ is methoxymethyl, $R^2$ is H, $R^3$ is methoxymethyl, $R^5$ is methoxymethyl, and $R^6$ and $R^7$ taken together form —C(CH$_3$)$_2$—.

2. The compound of claim 1, wherein $R^1$ is H, methoxymethyl,

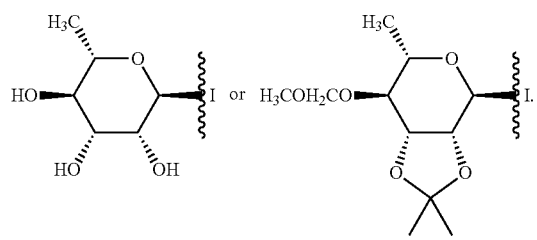

3. The compound of claim 1, wherein $R^2$ is H.

4. The compound of claim 1, wherein $R^3$ is H or methoxymethyl.

5. The compound of claim 1, wherein $R^4$ is 1,2-dihydroxyethyl, formyl, cyano, hydroxymethyl, ethynyl, carboxy, 2,2,2-trifluoro-1-hydroxyethyl, hydroximinomethyl,

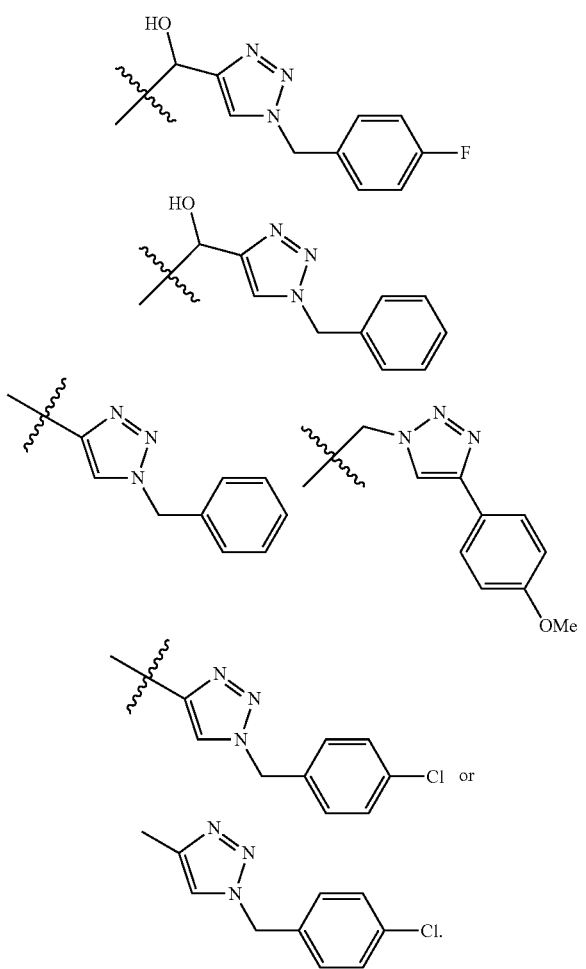

6. The compound of claim 1, wherein $R^5$ is H or methoxymethyl.

7. The compound of claim 1, wherein $R^6$ is H.

8. The compound of claim 1, wherein $R^7$ is H.

9. The compound of claim 1, wherein $R^6$ and $R^7$ taken together form $-C(CH_3)_2-$.

10. The compound of claim 1, wherein the compound is not one of the compounds:
   4-((3R,3aR,5R,5bR,9aR,11S,12aS,14bS)-5,12a,14b-trihydroxy-11-(((3aR,4R,6S,7S,7aR)-7-hydroxy-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxin-3-yl)furan-2(5H)-one (1);
   (2R,3R,4R,5S,6S)-2-(((1R,3S,5S,10R,11R,13R,14S,17R)-1,11-diacetoxy-10-(acetoxymethyl)-5,14-dihydroxy-13-methyl-17-(5-oxo-2,5-dihydrofuran-3-yl)hexadecahydro-1H-cyclopenta[a]phenanthren-3-yl)oxy)-6-methyltetrahydro-2H-pyran-3,4,5-triyl triacetate (1a); or
   4-((3R,3aR,5R,5bR,9aR,11S,12aS,14bS)-5,11,12a,14b-tetrahydroxy-3a,8,8-trimethylhexadecahydro-1H-cyclopenta[7,8]phenanthro[4,4a-d][1,3]dioxin-3-yl)furan-2(5H)-one (12).

11. A compound selected from the group consisting of:
   4-((3R,3aR,5R,5bR,9aR,11S,12aS,14bS)-12a,14b-dihydroxy-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxin-3-yl)furan-2(5H)-one (2);
   (3S,3aR,5R,5bR,9aR,11S,12aS,14bS)-3-(1,2-dihydroxyethyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (3);
   (3S,3aR,5R,5bR,9aR,11S,12aS,14bS)-12a,14b-dihydroxy-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-3-carbaldehyde (4);
   (3S,3aR,5R,5bR,9aR,11S,12aS,14bS)-3-(1-hydroxyprop-2-yn-1-yl)-5-(methoxymethoxy)-11-(((3aR,4R,6S,7S,7aR)-7-(methoxymethoxy)-2,22,6-trimethyltetrahydro-3a-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (5);
   (3S,3aR,5R,5bR,9aR,11S,12aS,14bS)-3-((1-(4-fluorobenzyl)-1H-1,2,3-triazol-4-yl)(hydroxy)methyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (6);
   (3S,3aR,5R,5bR,9aR,11S,12aS,14bS)-3-((1-benzyl-1H-1,2,3-triazol-4-yl)(hydroxy)methyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (7);
   (1R,3S,5S,10R,11R,13R,14S,17S)-17-((1-(4-fluorobenzyl)-1H-1,2,3-triazol-4-yl)(hydroxy)methyl)-10-(hydroxymethyl)-13-methyl-3-(((2R,3R,4R,5R,6S)-3,4,5-trihydroxy-6-methyltetrahydro-2H-pyran-2-yl)oxy)hexadecahydro-1H-cyclopenta[a]phenanthrene-1,5,11,14-tetraol (8);
   (1R,3S,5S,10R,11R,13R,14S,17S)-17-((1-benzyl-1H-1,2,3-triazol-4-yl)(hydroxy)methyl)-10-(hydroxymethyl)-13-methyl-3-(((2R,3R,4R,5R,6S)-3,4,5-trihydroxy-6-methyltetrahydro-2H-pyran-2-yl)oxy)hexadecahydro-1H-cyclopenta[a]phenanthrene-1,5,11,14-tetraol (9);
   (3S,3aR,5R,5bR,9aR,11S,12aS,14bS)-3-(hydroxymethyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (10);
   (3S,3aR,5R,5bR,9aR,11S,12aS,14bS)-12a,14b-dihydroxy-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-3-carbonitrile (11);
   4-((3R,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxin-3-yl)furan-2(5H)-one (13);
   2-hydroxy-1-((3S,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxin-3-yl)ethanone (14);

1-((3S,3aR,5R,5bR,9aR,11S,12aS,14bS)-12a-hydroxy-5, 11,14b-tris(methoxymethoxy)-3a,8,8-trimethylhexadecahydro-1H-cyclopenta[7,8]phenanthro[4,4a-d][1,3]dioxin-3-yl)ethane-1,2-diol (15);

(3S,3aR,5R,5bR,9aR,11S,12aS,14bS)-12a-hydroxy-5,11, 14b-tris(methoxymethoxy)-3a,8,8-trimethylhexadecahydro-1H-cyclopenta[7,8]phenanthro[4,4a-d][1,3]dioxine-3-carbaldehyde (16);

(3S,3aR,5R,5bR,9aR,11S,12aS,14bS)-3-(1-hydroxyprop-2-yn-1-yl)-5,11,12a-tris(methoxymethoxy)-3a,8,8-trimethylhexadecahydro-1H-cyclopenta[7,8]phenanthro[4,4a-d][1,3]dioxin-14b-ol (17);

(3S,3aR,5R,5bR,9aR,11S,12aS,14bS)-3-((1-benzyl-1H-1,2,3-triazol-4-yl)(hydroxy)methyl)-5,11,14b-tris(methoxymethoxy)-3a,8,8-trimethylhexadecahydro-1H-cyclopenta[7,8]phenanthro[4,4a-d][1,3]dioxin-12a-ol (18);

(3S,3aR,5R,5bR,9aR,11S,12aS,14bS)-3-((1-(4-fluorobenzyl)-1H-1,2,3-triazol-4-yl)(hydroxy)methyl)-5, 11,14b-tris(methoxymethoxy)-3a,8,8-trimethylhexadecahydro-1H-cyclopenta[7,8]phenanthro[4,4a-d][1,3]dioxin-12a-ol (19);

(1R,3S,5S,10R,11R,13R,14S,17S)-17-((1-benzyl-1H-1,2,3-triazol-4-yl)(hydroxy)methyl)-10-(hydroxymethyl)-13-methylhexadecahydro-1H-cyclopenta[a]phenanthrene-1,3,5,11,14-pentaol (20);

(1R,3S,5S,10R,11R,13R,14S,17S)-17-((1-(4-fluorobenzyl)-1H-1,2,3-triazol-4-yl)(hydroxy)methyl)-10-(hydroxymethyl)-13-methylhexadecahydro-1H-cyclopenta[a]phenanthrene-1,3,5,11,14-pentaol (21);

(3S,3aR,5R,5bR,9aR,11S,12aS,14bS)-3-(hydroxymethyl)-5,11,14b-tris(methoxymethoxy)-3a,8,8-trimethylhexadecahydro-1H-cyclopenta[7,8]phenanthro[4,4a-d][1,3]dioxin-12a-ol (22);

((3S,3aR,5R,5bR,9aR,11S,12aS,14bS)-12a-hydroxy-5, 11,14b-tris(methoxymethoxy)-3a,8,8-trimethylhexadecahydro-1H-cyclopenta[7,8]phenanthro[4,4a-d][1,3]dioxin-3-yl)methyl 4-methylbenzenesulfonate (23);

(3S,3aR,5R,5bR,9aR,11S,12aS,14bS)-3-(azidomethyl)-5, 11,14b-tris(methoxymethoxy)-3a,8,8-trimethylhexadecahydro-1H-cyclopenta[7,8]phenanthro[4,4a-d][1,3]dioxin-12a-ol (24);

(3S,3aR,5R,5bR,9aR,11S,12aS,14bS)-5,11,14b-tris(methoxymethoxy)-3-((4-(4-methoxyphenyl)-1H-1,2,3-triazol-1-yl)methyl)-3a,8,8-trimethylhexadecahydro-1H-cyclopenta[7,8]phenanthro[4,4a-d][1,3]dioxin-12a-ol (25);

(1R,3S,5S,10R,11R,13R,14S,17S)-10-(hydroxymethyl)-17-((4-(4-methoxyphenyl)-1H-1,2,3-triazol-1-yl)methyl)-13-methylhexadecahydro-1H-cyclopenta[a]phenanthrene-1,3,5,11,14-pentaol (26);

(3R,3aR,5R,5bR,9aR,11S,12aS,14bS)-3-ethynyl-5,11, 14b-tris(methoxymethoxy)-3a,8,8-trimethylhexadecahydro-1H-cyclopenta[7,8]phenanthro[4,4a-d][1,3]dioxin-12a-ol (28);

(3S,3aR,5R,5bR,9aR,11S,12aS,14bS)-3-(1-benzyl-1H-1,2,3-triazol-4-yl)-5,11,14b-tris(methoxymethoxy)-3a,8,8-trimethylhexadecahydro-1H-cyclopenta[7,8]phenanthro[4,4a-d][1,3]dioxin-12a-ol (29);

(3S,3aR,5R,5bR,9aR,11S,12aS,14bS)-3-(1-(4-chlorobenzyl)-1H-1,2,3-triazol-4-yl)-5,11,14b-tris(methoxymethoxy)-3a,8,8-trimethylhexadecahydro-1H-cyclopenta[7,8]phenanthro[4,4a-d][1,3]dioxin-12a-ol (30);

(3S,3aR,5R,5bR,9aR,11S,12aS,14bS)-3-(1-(4-fluorobenzyl)-1H-1,2,3-triazol-4-yl)-5,11,14b-tris(methoxymethoxy)-3a,8,8-trimethylhexadecahydro-1H-cyclopenta[7,8]phenanthro[4,4a-d][1,3]dioxin-12a-ol (31);

(1R,3S,5S,10R,11R,13R,14S,17S)-17-(1-benzyl-1H-1,2,3-triazol-4-yl)-10-(hydroxymethyl)-13-methylhexadecahydro-1H-cyclopenta[a]phenanthrene-1,3,5,11,14-pentaol (32);

(1R,3S,5S,10R,11R,13R,14S,17S)-17-(1-(4-chlorobenzyl)-1H-1,2,3-triazol-4-yl)-10-(hydroxymethyl)-13-methylhexadecahydro-1H-cyclopenta[a]phenanthrene-1,3,5,11,14-pentaol (33);

(1R,3S,5S,10R,11R,13R,14S,17S)-17-(1-(4-fluorobenzyl)-1H-1,2,3-triazol-4-yl)-10-(hydroxymethyl)-13-methylhexadecahydro-1H-cyclopenta[a]phenanthrene-1,3,5,11,14-pentaol (34);

12a-hydroxy-5,11,14b-tris(methoxymethoxy)-3a,8,8-trimethylhexadecahydro-1H-cyclopenta[7,8]phenanthro[4,4a-d][1,3]dioxine-3-carbaldehyde oxime (35);

(3S,3aR,5R,5bR,9aR,11S,12aS,14bS)-12a-hydroxy-5,11, 14b-tris(methoxymethoxy)-3a,8,8-trimethylhexadecahydro-1H-cyclopenta[7,8]phenanthro[4,4a-d][1,3]dioxine-3-carbonitrile (36);

(3S,3aR,5R,5bR,9aR,11S,12aS,14bS)-5,11,14b-tris(methoxymethoxy)-3a,8,8-trimethyl-3-(2,2,2-trifluoro-1-hydroxyethyl)hexadecahydro-1H-cyclopenta[7,8]phenanthro[4,4a-d][1,3]dioxin-12a-ol (37); and (3S,3aR,5R,5bR,9aR,11S,12aS,14bS)-12a-hydroxy-5,11, 14b-tris(methoxymethoxy)-3a,8,8-trimethylhexadecahydro-1H-cyclopenta[7,8]phenanthro[4,4a-d][1,3]dioxine-3-carboxylic acid (38).

12. The compound of claim 11, wherein the chemical structure is one of:

(3S,3aR,5R,5bR,9aR,11S,12aS,14bS)-3-(hydroxymethyl)-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-12a,14b-diol (10);

(3S,3aR,5R,5bR,9aR,11S,12aS,14bS)-3-(hydroxymethyl)-5,11,14b-tris(methoxymethoxy)-3a,8,8-trimethylhexadecahydro-1H-cyclopenta[7,8]phenanthro[4,4a-d][1,3]dioxin-12a-ol (22); or (1R,3S,5S,10R,11R,13R,14S,17S)-17-(1-benzyl-1H-1,2,3-triazol-4-yl)-10-(hydroxymethyl)-13-methylhexadecahydro-1H-cyclopenta[a]phenanthrene-1,3,5,11,14-pentaol (32).

13. The compound of claim 11, wherein the chemical structure is one of:

(3S,3aR,5R,5bR,9aR,11S,12aS,14bS)-12a,14b-dihydroxy-5-(methoxymethoxy)-11-(((3aR,4R,6S,7S,7aR)-7-(methoxymethoxy)-2,2,6-trimethyltetrahydro-3aH-[1,3]dioxolo[4,5-c]pyran-4-yl)oxy)-3a,8,8-trimethylhexadecahydro-1H-cyclopenta[7,8]phenanthro[4,4a-d][1,3]dioxine-3-carbaldehyde (4);

2-hydroxy-1-((3S,3aR,5R,5bR,9aR,11S,12aS,14bS)-12a-hydroxy-5,11,14b-tris(methoxymethoxy)-3a,8,8-trimethylhexadecahydro-1H-cyclopenta[7,8]phenanthro[4,4a-d][1,3]dioxin-3-yl)ethanone (14);

(3S,3aR,5R,5bR,9aR,11S,12aS,14bS)-12a-hydroxy-5,11, 14b-tris(methoxymethoxy)-3a,8,8-trimethylhexadecahydro-1H-cyclopenta[7,8]phenanthro[4,4a-d][1,3]dioxine-3-carbaldehyde (16);

((3S,3aR,5R,5bR,9aR,11S,12aS,14bS)-12a-hydroxy-5, 11,14b-tris(methoxymethoxy)-3a,8,8-trimethylhexadecahydro-1H-cyclopenta[7,8]phenanthro[4,4a-d][1,3]dioxin-3-yl)methyl 4-methylbenzenesulfonate (23); or (3S,3aR,5R,5bR,9aR,11S,12aS,14bS)-3-(azidomethyl)-5,
11,14b-tris(methoxymethoxy)-3a,8,8-trimethylhexa-
decahydro-1H-cyclopenta[7,8]phenanthro[4,4a-d][1,3]
dioxin-12a-ol (24).

14. The compound of claim 1, wherein
R¹ is H, methoxymethyl,

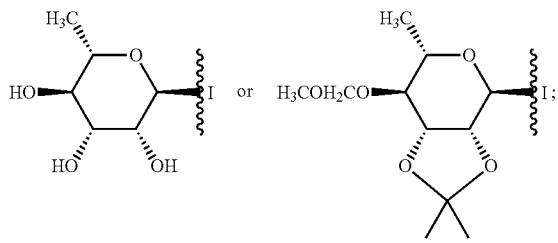

R² is H;
R³ is H or methoxymethyl;
R⁵ is H or methoxymethyl;
R⁶ and R⁷ are each H or R⁶ and R⁷ taken together form
—C(CH₃)₂⁻; and
R⁴ is 1,2-dihydroxyethyl, formyl, cyano, hydroxymethyl,
ethynyl, carboxy, 2,2,2-trifluoro-1-hydroxyethyl,
hydroximinomethyl,

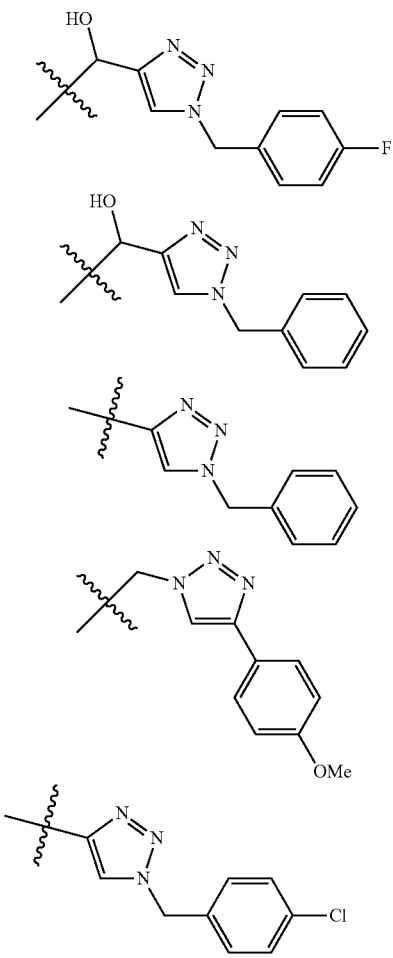

or

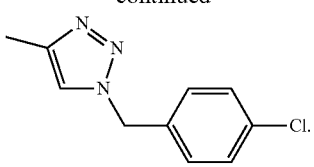

15. The compound of claim 14
R¹ is methoxymethyl,

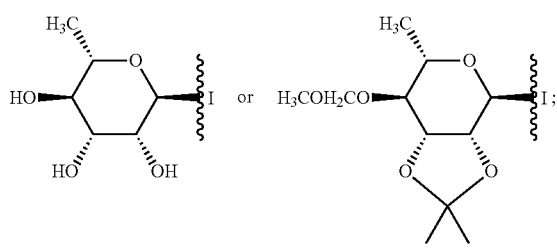

R² is H;
R³ is H or methoxymethyl;
R⁵ is H or methoxymethyl;
R⁶ and R⁷ are each H or R⁶ and R⁷ taken together form
—C(CH₃)₂⁻; and
R⁴ is 1,2-dihydroxyethyl, formyl, cyano, hydroxymethyl,
ethynyl, 2,2,2-trifluoro-1-hydroxyethyl, hydroximi-
nomethyl,

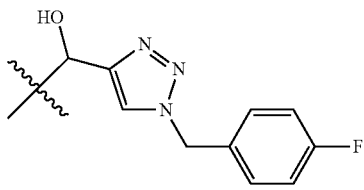

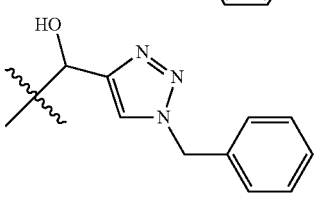

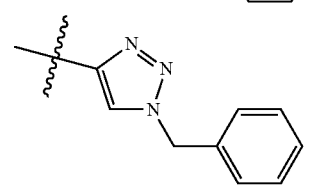

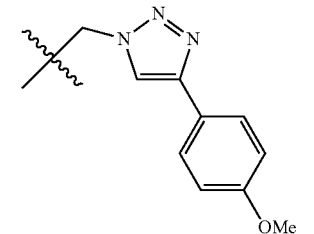

-continued

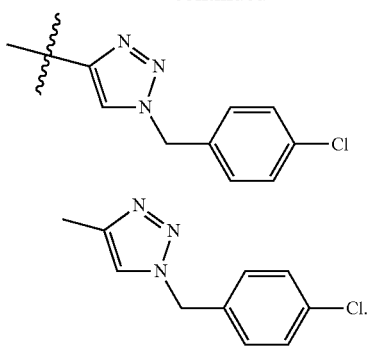

or

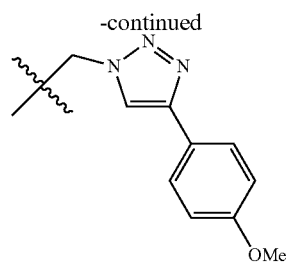

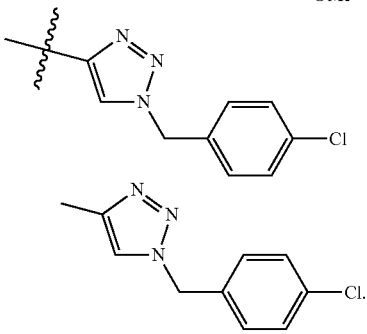

or

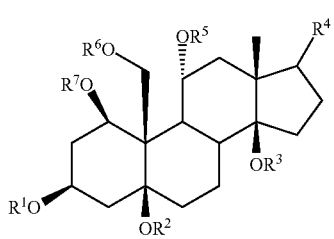

16. The compound of claim 14

R$^1$ is H, methoxymethyl,

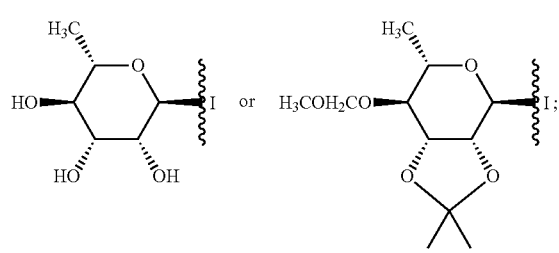

R$^2$ is H;
R$^3$ is H or methoxymethyl;
R$^5$ is H or methoxymethyl;
R$^6$ and R$^7$ are each H or R$^6$ and R$^7$ taken together form —C(CH$_3$)$_2$—; and
R$^4$ is 1,2-dihydroxyethyl, formyl, cyano, hydroxymethyl, ethynyl, 2,2,2-trifluoro-1-hydroxyethyl, hydroximinomethyl,

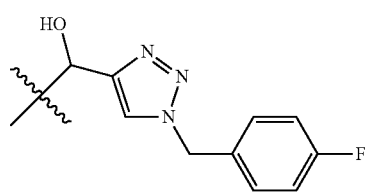

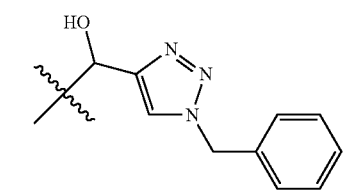

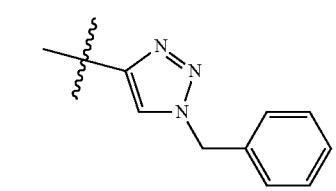

17. A compound of formula I:

(I)

wherein:
R$^1$ is H, (C$_1$-C$_6$)alkyl, or R$_c$, wherein the (C$_1$-C$_6$)alkyl is optionally substituted with one or more halo or (C$_1$-C$_6$)alkoxy;
R$^2$ is H or (C$_1$-C$_6$)alkyl, wherein the (C$_1$-C$_6$)alkyl is optionally substituted with one or more halo or (C$_1$-C$_6$)alkoxy;
R$^3$ is H or (C$_1$-C$_6$)alkyl, wherein the (C$_1$-C$_6$)alkyl is optionally substituted with one or more halo or (C$_1$-C$_6$)alkoxy;
R$^4$ is R$_a$, cyano, formyl, carboxy, hydroximinomethyl, (C$_1$-C$_4$)alkyl, (C$_2$-C$_4$)alkenyl, (C$_2$-C$_4$)alkynyl, aryl, heteroaryl, or (C$_1$-C$_4$)alkanoyl, wherein the (C$_1$-C$_4$) alkyl, (C$_2$-C$_4$)alkenyl, (C$_2$-C$_4$)alkynyl, and (C$_1$-C$_4$)alkanoyl is optionally substituted with one or more groups selected from hydroxy, halo, aryl, and heteroaryl; wherein any aryl and heteroaryl of R$^4$ is optionally substituted with one or more R$_b$;
R$^5$ is H or (C$_1$-C$_6$)alkyl, wherein the (C$_1$-C$_6$)alkyl is optionally substituted with one or more halo or (C$_1$-C$_6$)alkoxy;
R$^6$ is H or (C$_1$-C$_6$)alkyl, wherein the (C$_1$-C$_6$)alkyl is optionally substituted with one or more halo or (C$_1$-C$_6$)alkoxy; and
R$^7$ is H or (C$_1$-C$_6$)alkyl, wherein the (C$_1$-C$_6$)alkyl is optionally substituted with one or more halo or (C$_1$-C$_6$)alkoxy; or R$^6$ and R$^7$ taken together form a (C$_1$-C$_6$) alkylene;
R$_a$, is a 4, 5, or 6 membered saturated or partially unsaturated heterocyclic ring comprising at least one carbon atom and at least one heteroatom selected from O, S, or NH in the ring, which ring is optionally substituted with one or more oxo (=O);

$R_b$, is aryl or aryl($C_1$-$C_6$)alkyl, wherein the aryl or aryl ($C_1$-$C_6$)alkyl is optionally substituted with one or more ($C_1$-$C_6$)alkoxy or halo;

$R_c$, is a C-linked amino acid, a C-linked dipeptide, —C(=O)CH$_2$CH$_2$COOH, —P(=O)(OH)$_2$, or:

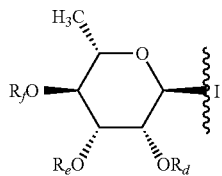

$R_d$ is H, ($C_1$-$C_6$)alkanoyl, or ($C_1$-$C_6$)alkyl, wherein the ($C_1$-$C_6$)alkanoyl and the ($C_1$-$C_6$)alkyl are each optionally substituted with one or more halo or ($C_1$-$C_6$) alkoxy; and $R_e$ is H, ($C_1$-$C_6$)alkanoyl, or ($C_1$-$C_6$)alkyl, wherein the ($C_1$-$C_6$)alkanoyl and the ($C_1$-$C_6$)alkyl are each optionally substituted with one or more halo or ($C_1$-$C_6$)alkoxy; or $R_d$ and $R_e$ taken together form a ($C_1$-$C_6$)alkylene; and $R_f$ is H, ($C_1$-$C_6$)alkanoyl, or ($C_1$-$C_6$)alkyl, wherein the ($C_1$-$C_6$)alkanoyl and the ($C_1$-$C_6$)alkyl are each optionally substituted with one or more halo or ($C_1$-$C_6$) alkoxy;

or a salt thereof, when $R_c$, is

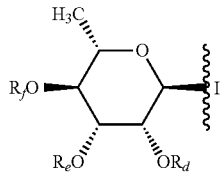

then $R^4$ is

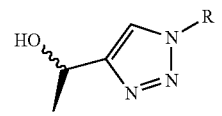

with R being 4-fluorobenzyl or benzyl, when R1 is H, then the compound is one of:

(1R,3S,5S,10R,11R,13R,14S,17S)-17-((1-benzyl-1H-1,2,3-triazol-4-yl)(hydroxy)methyl)-10-(hydroxymethyl)-13-methylhexadecahydro-1H-cyclopenta[a]phenanthrene-1,3,5,11,14-pentaol (20);

(1R,3S,5S,10R,11R,13R,14S,17S)-17-((1-(4-fluorobenzyl)-1H-1,2,3-triazol-4-yl)(hydroxy)methyl)-10-(hydroxymethyl)-13-methylhexadecahydro-1H-cyclopenta[a]phenanthrene-1,3,5,11,14-pentaol (21);

(1R,3S,5S,10R,11R,13R,14S,17S)-10-(hydroxymethyl)-17-((4-(4-methoxyphenyl)-1H-1,2,3-triazol-1-yl)methyl)-13-methylhexadecahydro-1H-cyclopenta[a]phenanthrene-1,3,5,11,14-pentaol (26);

(1R,3S,5S,10R,11R,13R,14S,17S)-17-(1-benzyl-1H-1,2,3-triazol-4-yl)-10-(hydroxymethyl)-13-methylhexadecahydro-1H-cyclopenta[a]phenanthrene-1,3,5,11,14-pentaol (32);

(1R,3S,5S,10R,11R,13R,14S,17S)-17-(1-(4-chlorobenzyl)-1H-1,2,3-triazol-4-yl)-10-(hydroxymethyl)-13-methylhexadecahydro-1H-cyclopenta[a]phenanthrene-1,3,5,11,14-pentaol (33); or (1R,3S,5S,10R,11R,13R,14S,17S)-17-(1-(4-fluorobenzyl)-1H-1,2,3-triazol-4-yl)-10-(hydroxymethyl)-13-methylhexadecahydro-1H-cyclopenta[a]phenanthrene-1,3,5,11,14-pentaol (34).

18. The compound of claim 17, wherein $R^1$ is methoxymethyl,

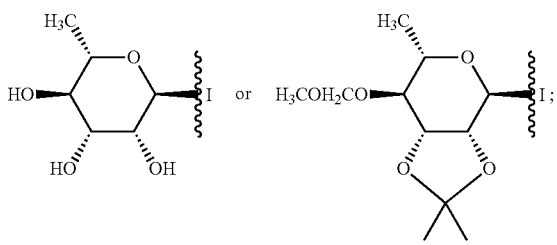

$R^2$ is H;

$R^3$ is H or methoxymethyl;

$R^5$ is H or methoxymethyl;

$R^6$ and $R^7$ are each H or $R^6$ and $R^7$ taken together form —C(CH$_3$)$_2$—; and $R^4$ is 1,2-dihydroxyethyl, formyl, cyano, hydroxymethyl, ethynyl, carboxy, 2,2,2-trifluoro-1-hydroxyethyl, hydroximinomethyl,

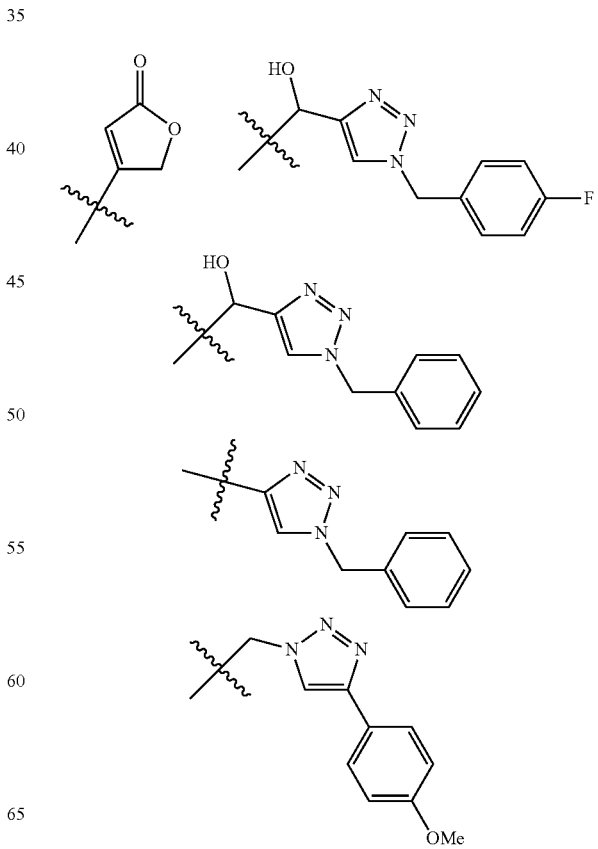

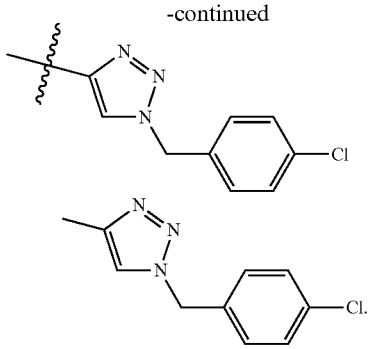
or
19. A pharmaceutical composition comprising:
a compound of claim 1, or a pharmaceutically acceptable salt thereof; and
a pharmaceutically acceptable diluent or carrier.
20. A method for decreasing sperm motility in a mammal comprising:
administering the compound of claim 1, or a pharmaceutically acceptable salt thereof to the mammal.
* * * * *

UNITED STATES PATENT AND TRADEMARK OFFICE
CERTIFICATE OF CORRECTION

PATENT NO. : 9,670,247 B2
APPLICATION NO. : 13/932778
DATED : June 6, 2017
INVENTOR(S) : Blanco et al.

It is certified that error appears in the above-identified patent and that said Letters Patent is hereby corrected as shown below:

On the Title Page

Item [57], Column 2, Line 8, delete "Na, K-ATPase" and insert -- Na,K-ATPase --, therefor.

In the Drawings

Fig. 2, Sheet 2 of 5, delete "(Oubain)" and insert -- (Ouabain) --, therefor.

Fig. 3, Sheet 3 of 5, delete " 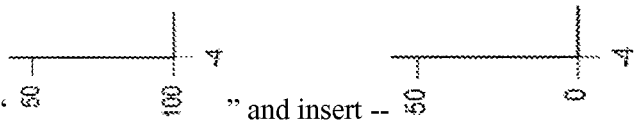 " and insert -- --, therefor.

In the Specification

Column 1, Line 14, delete "1U54-HD055763" and insert -- NIH 1U54-HD055763 --, therefor.

Column 1, Line 35, delete "an heterodimer" and insert -- a heterodimer --, therefor.

Column 1, Line 62, delete "includes" and insert -- include --, therefor.

Column 2, Line 14, delete "SSI-54" and insert -- SS-I-54 --, therefor.

Column 3, Line 22, delete "$R_k$," and insert -- $R_k$; --, therefor.

Column 3, Line 26, delete "$R_a$," and insert -- $R_a$ --, therefor.

Column 3, Line 31, delete "$R_b$," and insert -- $R_b$ --, therefor.

Column 3, Line 34, delete "$R_c$," and insert -- $R_c$ --, therefor.

Signed and Sealed this
Twenty-ninth Day of May, 2018

Andrei Iancu
*Director of the United States Patent and Trademark Office*

CERTIFICATE OF CORRECTION (continued)

U.S. Pat. No. 9,670,247 B2

Column 3, Line 35, delete "or:" and insert -- or --, therefor.

Column 3, Line 57, delete "$R_g$," and insert -- $R_g$ --, therefor.

Column 3, Line 60, delete "$R_h$," and insert -- $R_h$ --, therefor.

Column 3, Line 66, delete "$R_m$," and insert -- $R_m$ --, therefor.

Column 4, Line 4, delete "$R_n$," and insert -- $R_n$ --, therefor.

Column 4, Lines 29-30, delete "an mammal" and insert -- a mammal --, therefor.

Column 4, Line 61, delete "gamma-carboxyglutamate;" and insert -- gamma-carboxyglutamate, --, therefor.

Column 4, Line 64, delete "citruline," and insert -- citrulline, --, therefor.

Column 5, Line 24, delete "phase." and insert -- phase). --, therefor.

Column 5, Line 28, delete "substituents" and insert -- substituents. --, therefor.

Column 5, Lines 34-35, delete "1,-pentenyl," and insert -- 1-pentenyl, --, therefor.

Column 5, Line 38, delete "2-butyryl, 3-butyryl," and insert -- 2-butynyl, 3-butynyl, --, therefor.

Column 6, Line 4, delete "alkoxy" and insert -- alkoxy; --, therefor.

Column 6, Line 27, delete "$R_a$," and insert -- $R_a$ --, therefor.

Column 6, Line 32, delete "$R_b$," and insert -- $R_b$ --, therefor.

Column 6, Line 35, delete "$R_c$," and insert -- $R_c$ --, therefor.

Column 6, Line 36, delete "or:" and insert -- or --, therefor.

Column 7, Line 37, delete "$R_k$," and insert -- $R_k$; --, therefor.

Column 7, Line 44, delete "$R_m$," and insert -- $R_m$ --, therefor.

Column 7, Line 49, delete "$R_n$," and insert -- $R_n$ --, therefor.

Column 8, Line 67, delete "–$C(CH_3)_2$–." and insert -- –$C(CH_3)_2$-. --, therefor.

Column 11, Line 24, delete "3510-3513.)." and insert -- 3510-3513). --, therefor.

Column 11, Line 28, delete "Ozolalysis" and insert -- Ozonolysis --, therefor.

CERTIFICATE OF CORRECTION (continued)
U.S. Pat. No. 9,670,247 B2

Column 11, Line 61, delete "(Paquett e" and insert -- (Paquette --, therefor.

Column 19, Line 50, delete "$R^{10}$ = OH, marpholino" and insert -- $R^{10}$ = OH, morpholino --, therefor.

Columns 19 & 20, Lines 67 & 25, delete "tartarate," and insert -- tartrate, --, therefor.

Column 22, Line 60, delete "molibdate." and insert -- molybdate. --, therefor.

Column 39, Line 38, delete "rta" and insert -- rat --, therefor.

Column 39, Line 46, delete "μM" and insert -- μm --, therefor.

Column 39, Line 52, delete "20×" and insert -- 20X --, therefor.

Column 40, Line 62, delete "electrospray" and insert -- electrospray ionization --, therefor.

Column 43, Line 42, delete "753.4061." and insert -- 753.4061, --, therefor.

Column 44, Line 66, delete "731.4218." and insert -- 731.4218, --, therefor.

Column 45, Line 48, delete "filterate" and insert -- filtrate --, therefor.

Column 45, Line 67, delete "699.3956." and insert -- 699.3956, --, therefor.

Column 49, Line 5, delete "$CuSO_{4.5H_2}O$„ and insert -- $CuSO_4.5H_2O$ --, therefor.

Column 49, Line 7, delete ")4 mL)," and insert -- (4 mL), --, therefor.

Column 49, Line 12, delete "1H)" and insert -- 1H), --, therefor.

Column 50, Line 7, delete "876.4658." and insert -- 876.4658, --, therefor.

Column 54, Line 15, delete "701.4112." and insert -- 701.4112, --, therefor.

Column 55, Line 28, delete "$C_{36}H_{58}O_{12}(M+H)^+$ 696.3959." and
insert -- $C_{36}H_{58}O_{12}$ $(M+H)^+$ 696.3959, --, therefor.

Column 56, Line 58, delete "acetate 1:9)" and insert -- acetate, 1:9) --, therefor.

Column 56, Line 67, delete "633.3251." and insert -- 633.3251, --, therefor.

Column 57, Line 64, delete "58%," and insert -- 58% --, therefor.

Column 58, Line 56, delete "acetate 1:9)" and insert -- acetate, 1:9) --, therefor.

Column 58, Line 67, delete "589.3588." and insert -- 589.3588, --, therefor.

CERTIFICATE OF CORRECTION (continued)

U.S. Pat. No. 9,670,247 B2

Column 59, Line 66, delete "579.3145." and insert -- 579.3145, --, therefor.

Column 60, Line 67, delete "605.3302." and insert -- 605.3302, --, therefor.

Column 62, Line 5, delete "11'" and insert -- 1H --, therefor.

Column 62, Line 47, delete "CD$_3$OD):" and insert -- CD$_3$OD) --, therefor.

Column 62, Line 50, delete "544.3023." and insert -- 544.3023, --, therefor.

Column 62, Line 67, delete "562.2929." and insert -- 562.2929, --, therefor.

Column 63, Line 55, delete "(c" and insert -- (c= --, therefor.

Column 63, Line 66, delete "581.3302." and insert -- 581.3302, --, therefor.

Column 65, Line 44, delete "Cu$_2$SO$_4$, 5H$_2$O" and insert -- Cu$_2$SO$_4$. 5H$_2$O --, therefor.

Column 67, Line 26, delete "544.3023." and insert -- 544.3023, --, therefor.

Column 67, Line 67, delete "aceone/" and insert -- acetone/ --, therefor.

Column 68, Lines 24-25, delete "C$_{30}$H$_{49}$O$_9$(M+H)$^+$ 553.3377." and insert -- C$_{30}$H$_{49}$O$_9$ (M+H)$^+$ 553.3377, --, therefor.

Column 68, Line 40, delete "Cu$_2$SO$_4$, 5H$_2$O" and insert -- Cu$_2$SO$_4$. 5H$_2$O --, therefor.

Column 69, Line 22, delete "686.4017." and insert -- 686.4017, --, therefor.

Column 69, Line 48, delete "720.3627." and insert -- 720.3627, --, therefor.

Column 70, Line 17, delete "r.t." and insert -- r.t, --, therefor.

Column 70, Line 45, delete "the 32" and insert -- 32 --, therefor.

Column 70, Line 53, delete "514.2917." and insert -- 514.2917, --, therefor.

Column 70, Line 64, delete "51%):" and insert -- 51%). --, therefor.

Column 71, Line 10, delete "53%):" and insert -- 53%). --, therefor.

Column 71, Line 15, delete "532.2823." and insert -- 532.2823, --, therefor.

Column 72, Line 6, delete "572.3435." and insert -- 572.3435, --, therefor.

Column 72, Line 55, delete "(c" and insert -- (c= --, therefor.

CERTIFICATE OF CORRECTION (continued)

U.S. Pat. No. 9,670,247 B2

Column 72, Line 66, delete "554.3329." and insert -- 554.3329, --, therefor.

Column 73, Line 45, delete "627.3356." and insert -- 627.3356, --, therefor.

Column 74, Line 22, delete "(c" and insert -- (c= --, therefor.

Column 74, Line 33, delete "573.3275." and insert -- 573.3275, --, therefor.

Column 74, Line 35, delete "Example" and insert -- Examples --, therefor.

Column 74, Line 37, delete "spiro [[1,3]" and insert -- spiro[[1,3] --, therefor.

Column 75, Line 67, delete "305.2202." and insert -- 305.2202, --, therefor.

Column 76, Line 4, delete "4-a-methyl-4,4-a," and insert -- 4a-methyl-4,4a, --, therefor.

Column 76, Line 53, delete "4-a-methyl" and insert -- 4a-methyl --, therefor.

Column 76, Line 60, delete "Bn-$N_3$" and insert -- Bn–$N_3$ --, therefor.

Column 77, Line 32, delete "322.1919." and insert -- 322.1919, --, therefor.

Column 77, Line 36, delete "4-a-methyl" and insert -- 4a-methyl --, therefor.

Column 78, Line 10, delete "378.2406." and insert -- 378.2406, --, therefor.

Column 78, Line 34, delete "hexane" and insert -- hexane, --, therefor.

Column 79, Line 67, delete "308.1763." and insert -- 308.1763, --, therefor.

Column 80, Line 1, delete "Example" and insert -- Examples --, therefor.

Column 81, Line 37, delete "$CH_3OH$," and insert -- $CH_3OH$ --, therefor.

Column 81, Line 67, delete "175.1123." and insert -- 175.1123, --, therefor.

Column 82, Line 38, delete "(c" and insert -- (c= --, therefor.

Column 82, Line 45, delete "308.1763." and insert -- 308.1763, --, therefor.

Column 84, Line 34, delete "(c" and insert -- (c= --, therefor.

Column 84, Line 39, delete "218.1293." and insert -- 218.1293, --, therefor.

Column 85, Line 47, delete "$BF_3$, $OEt_2$" and insert -- $BF_3$. $OEt_2$ --, therefor.

CERTIFICATE OF CORRECTION (continued)
U.S. Pat. No. 9,670,247 B2

Column 88, Line 22, delete "Na-ascrobate" and insert -- Na-ascorbate --, therefor.

Column 88, Line 67, delete "670.4193." and insert -- 670.4193, --, therefor.

Column 89, Line 19, delete "652.3934." and insert -- 652.3934, --, therefor.

Column 89, Line 33, delete "Na-ascrobate" and insert -- Na-ascorbate --, therefor.

Column 90, Line 15, delete "580.3723." and insert -- 580.3723, --, therefor.

Column 90, Line 60, delete "(c" and insert -- (c= --, therefor.

Column 91, Line 3, delete "432.3015." and insert -- 432.3015, --, therefor.

Column 91, Line 13, delete "(c" and insert -- (c= --, therefor.

Column 91, Line 22, delete "414.2757." and insert -- 414.2757, --, therefor.

Column 91, Line 32, delete "mp." and insert -- mp --, therefor.

Column 91, Line 36, delete "342.2545." and insert -- 342.2545, --, therefor.

Column 92, Line 64, delete "hexane" and insert -- hexane, --, therefor.

Column 92, Line 65, delete "solid:" and insert -- solid. --, therefor.

Column 93, Line 60, delete "Na-ascrobate" and insert -- Na-ascorbate --, therefor.

Column 94, Line 42, delete "656.4036." and insert -- 656.4036, --, therefor.

Column 95, Line 20, delete "(c" and insert -- (c= --, therefor.

Column 95, Line 30, delete "418.2858." and insert -- 418.2858, --, therefor.

Column 96, Line 19, delete "443.2923." and insert -- 443.2923, --, therefor.

Column 96, Line 66, delete "$CHCl_3$/" and insert -- $CHCl_3$: --, therefor.

Column 97, Line 1, delete "(c" and insert -- (c= --, therefor.

Column 97, Line 10, delete "487.3437." and insert -- 487.3437, --, therefor.

Column 97, Line 60, delete "hexanex" and insert -- hexanes, --, therefor.

Column 102, Line 56, delete "(c" and insert -- (c= --, therefor.

Column 103, Line 5, delete "3-yl-2,6" and insert -- 3-yl 2,6 --, therefor.

Column 103, Line 32, delete "L-lycine" and insert -- L-lysine --, therefor.

Column 105, Line 23, delete "(c" and insert -- (c= --, therefor.

Column 107, Line 13, delete "Na-ascrobate" and insert -- Na-ascorbate --, therefor.

Column 108, Line 38, delete "EtOAc" and insert -- EtOAc, --, therefor.

Column 109, Line 22, delete "EtOAc 1:1) to give the" and insert -- EtOAc, 1:1) to give --, therefor.

Column 110, Line 4, delete "(c" and insert -- (c= --, therefor.

Column 110, Line 5, delete "OD)" and insert -- OD) δ --, therefor.

Column 111, Line 38, delete "ether-a-go-go" and insert -- ether-à-go-go --, therefor.

Column 113, Line 2, delete "SSI-54" and insert -- SS-I-54 --, therefor.

In the Claims

Column 113, Line 57, Claim 1, delete "$R_a$," and insert -- $R_a$ --, therefor.

Column 113, Line 62, Claim 1, delete "$R_b$," and insert -- $R_b$ --, therefor.

Column 113, Line 66, Claim 1, delete "$R_c$," and insert -- $R_c$ --, therefor.

Column 113, Line 67, Claim 1, delete "or:" and insert -- or --, therefor.

Column 114, Line 24, Claim 1, delete "$R_c$," and insert -- $R_c$ --, therefor.

Column 116, Line 19, Claim 11, delete "2,22,6" and insert -- 2,2,6 --, therefor.

Column 116, Line 20, Claim 11, delete "3a-[1,3]" and insert -- 3aH-[1,3] --, therefor.

Column 120, Line 10, Claim 15, delete "claim 14" and insert -- claim 14, wherein --, therefor.

Column 121, Line 18, Claim 16, delete "claim 14" and insert -- claim 14, wherein --, therefor.

Column 121, Line 37, Claim 16, delete "–C(CH$_3$)$_2$–;" and insert -- –C(CH$_3$)$_2^-$; --, therefor.

Column 122, Line 66, Claim 17, delete "$R_a$," and insert -- $R_a$ --, therefor.

Column 123, Line 4, Claim 17, delete "$R_b$," and insert -- $R_b$ --, therefor.

Column 123, Line 7, Claim 17, delete "$R_c$," and insert -- $R_c$ --, therefor.

Column 123, Line 8, Claim 17, delete "or:" and insert -- or --, therefor.

Column 123, Line 31, Claim 17, delete "$R_c$," and insert -- $R_c$ --, therefor.

Column 123, Line 51, Claim 17, delete "R1" and insert -- $R^1$ --, therefor.